(12) United States Patent
Yang et al.

(10) Patent No.: US 10,472,411 B2
(45) Date of Patent: Nov. 12, 2019

(54) RECOMBINANT ANTIBODY AND USES THEREOF

(71) Applicant: Academia Sinica, Taipei (TW)

(72) Inventors: An-Suei Yang, Emeryville, CA (US); Hong-Sen Chen, Taipei (TW); Ing-Chien Chen, Taipei (TW); Chao-Ping Tung, Taipei (TW); Shin-Chen Hou, Taipei (TW); Chung-Ming Yu, Taipei (TW); Chi-Kai Yang, Taipei (TW); Yi-Kai Chiu, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/409,994

(22) Filed: May 13, 2019

(65) Prior Publication Data

US 2019/0263893 A1    Aug. 29, 2019

Related U.S. Application Data

(62) Division of application No. 15/547,523, filed on Jul. 31, 2017, now Pat. No. 10,336,816.

(51) Int. Cl.

| C07K 16/00 | (2006.01) |
| C12N 15/10 | (2006.01) |
| C07K 16/28 | (2006.01) |
| C07K 16/18 | (2006.01) |
| C07K 16/22 | (2006.01) |
| C07K 16/24 | (2006.01) |
| C07K 16/32 | (2006.01) |
| C07K 16/10 | (2006.01) |

(52) U.S. Cl.
CPC ........ *C07K 16/005* (2013.01); *C07K 16/1018* (2013.01); *C07K 16/18* (2013.01); *C07K 16/22* (2013.01); *C07K 16/245* (2013.01); *C07K 16/2803* (2013.01); *C07K 16/2827* (2013.01); *C07K 16/2863* (2013.01); *C07K 16/2887* (2013.01); *C07K 16/32* (2013.01); *C12N 15/1037* (2013.01); *C07K 2317/34* (2013.01); *C07K 2317/622* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

2013/0323787 A1* 12/2013 Yang .................... C07K 16/005
435/69.6

OTHER PUBLICATIONS

Thesis, Cobaugh, Christian Wessel. "Single scaffold antibody libraries created with high rates of mutagenesis or diversity focused for peptide recognition." (2007) (Year: 2007).*
Vargas-Madrazo et al.( Journal of molecular biology 254.3 (1995): 497-504) (Year: 1995).*
Hsu et al. ( Structure 22.1 (2014): 22-34). (Year: 2014).*
Hsu et al. supplementtary materials (Year: 2014).*

* cited by examiner

*Primary Examiner* — Tracy Vivlemore
*Assistant Examiner* — Sahana S Kaup

(57) ABSTRACT

Disclosed herein is a phage-displayed single-chain variable fragment (scFv) library, that comprised a plurality of phage-displayed scFvs characterized with (1) a specific CS combination; (2) a specific distribution of aromatic residues in each CDR; and (3) a specific sequence in each CDR. The present scFv library could be used to efficiently produce different antibodies with binding affinity to different antigens. Accordingly, the present disclosure provides a potential means to generate different antigen-specific antibodies promptly in accordance with the need in experimental researches and/or clinical applications.

16 Claims, 5 Drawing Sheets

Specification includes a Sequence Listing.

RECOMBINANT ANTIBODY AND USES THEREOF

CROSS-REFERENCE TO RELATED APPLICATION

This application is a divisional application of U.S. application Ser. No. 15/547,523, filed Jul. 31, 2017, which is a U.S. National Stage Filing under 35 U.S.C. 371 from International Patent Application Serial No. PCT/US2016/019128, filed Feb. 23, 2016, and published on Sep. 1, 2016, which claims the benefit of U.S. Provisional Application No. 62/120,352, filed Feb. 24, 2015, the contents of said application are incorporated herein by reference in its entirety.

BACKGROUND OF THE INVENTION

1. Field of the Invention

The present disclosure in general relates to the field of antibody fragment library. More particularly, the present disclosure relates to a phage-displayed single-chain variable fragment (scFv) library and the uses thereof.

2. Description of Related Art

An antibody, also known as an immunoglobulin, is a large Y-shape protein produced by plasma cells that is used by the immune system to identify and neutralize foreign objects, such as bacteria and viruses. The antibody recognizes a unique part of the foreign target, called an antigen. Each tip of the "Y" of an antibody contains a paratope that is specific for one particular epitope on an antigen, allowing these two structures to bind together with precision. Using this binding mechanism, an antibody can tag a microbe or an infected cell, and accordingly, facilitating the subsequent attack by other parts of the immune system, or can neutralize its target directly (for example, by blocking a part of a microbe that is essential for its invasion and survival). The production of antibodies is the main function of the humoral immune system.

Antibodies are typically made of basic structural units—each with two large heavy chains and two small light chains. There are five types of heavy chains denoted as alpha ($\alpha$), delta ($\delta$), epsilon ($\epsilon$), gamma ($\gamma$), and mu ($\mu$). The type of heavy chain present defines the isotypes of antibody; these chains are found in immunoglobulin A (IgA), immunoglobulin D (IgD), immunoglobulin E (IgE), immunoglobulin G (IgG), and immunoglobulin M (IgM) antibodies, respectively. Each heavy chain has two regions: the constant region (CH) and the variable region (VH). The constant region is identical in all antibodies of the same isotype, but differs in antibodies of different isotypes. The variable region of the heavy chain differs in antibodies produced by different B cells, but is the same for all antibodies produced by a single B cell or B cell clone that is stimulated and activated by a specific antigen. As to the light chain, it is known that there are two types of light chain, which are denoted as lambda ($\lambda$) and kappa ($\kappa$). With the similar structure of the heavy chain, each light chain has two regions: one constant region (CL) and one variable region (VL), in which the constant region is unchangeable in antibodies of the same isotype, while the variable region is different depending on the stimulated antigen.

Though the general structure of all antibodies is very similar, a small region at the tip of antibody is extremely variable, allowing millions of antibodies with slightly different tip structures (i.e., antigen-binding sites, or paratopes) to exist. This region is known as the hypervariable region or complementarity determining region (CDR). Each of these variants can bind to a different antigen, and thus, the enormous diversity of antibodies allows the immune system to recognize an equally wide variety of antigens. The large and diverse population of antibodies is generated by random combinations of a set of gene segments (i.e., variable segment, diversity segment, and joining segment) that encode different paratopes, followed by random mutations (also known as somatic hypermutations, SHMs) in this area of the antibody gene, which create further diversity.

For the preparation of antibodies, generally a native or recombinant protein or fragment thereof is used to immunize an animal, so that an antibody that can specifically recognize and bind the protein/fragment is produced in the animal. Then various technical means can be used based on corresponding requirements to obtain antibody from the animal, such as monoclonal antibody or polyclonal antibody. The production of monoclonal antibody typically relies on hybridoma techniques. In such techniques, after immunizing the animal, the cells of the animal would be taken and fused to generate an antibody-producing hybridoma, which is then cloned to construct a strain for producing antibody, and subsequently the antibody is purified and identified. Although these methods currently are widely used in the preparations of antibodies, they also have many disadvantages, such as long preparation periods that involve complicated techniques, incomplete recognition of epitopes, and high manufacturing cost etc. Further, such methods cannot be applied to all the proteins/fragments, particularly to antigens with low solubility, low immunogenicity, or antigens with toxicity, such methods would be inappropriate.

In view of the forging, there exists in the related art a need for a system and/or method for producing an antibody with binding affinity and specificity to a specific antigen in a more cost-efficient manner.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the present disclosure is directed to a phage-displayed single-chain variable fragment (scFv) library that comprises a plurality of phage-displayed scFvs. In the present library, each of the plurality of phage-displayed scFv comprises a first heavy chain complementarity determining region (CDR-H1), a second heavy chain CDR (CDR-H2), a third heavy chain CDR (CDR-H3), a first light chain CDR (CDR-L1), a second light chain CDR (CDR-L2), and a third light chain CDR (CDR-L3); in which each of the CDR-H1, CDR-L2 and CDR-L3 has a type 1 canonical structure (CS), whereas each of the CDR-H2 and CDR-L1 has a type 2 CS; and each of the CDR-H1, CDR-H2, CDR-H3, CDR-L1, CDR-L2, and CDR-L3 has a distribution of aromatic residues that is similar to the distribution of aromatic residues in the corresponding CDR-H1, CDR-H2, CDR-H3, CDR-L1, CDR-L2, and CDR-L3 of a natural antibody.

According to the embodiments of the present disclosure, the CDR-L1 is encoded by a first coding sequence comprising the nucleic acid sequence of any of SEQ ID NOs: 2-10, the CDR-L2 is encoded by a second coding sequence comprising the nucleic acid sequence of any of SEQ ID NOs: 11-14, the CDR-L3 is encoded by a third coding sequence comprising the nucleic acid sequence of any of SEQ ID NOs: 15-22, the CDR-H1 is encoded by a fourth coding sequence comprising the nucleic acid sequence of any of SEQ ID NOs: 23-26, the CDR-H2 is encoded by a fifth coding sequence comprising the nucleic acid sequence of any of SEQ ID NOs: 27-28, and the CDR-H3 is encoded by a sixth coding sequence comprising the nucleic acid sequence of any of SEQ ID NOs: 29-106.

According to one embodiment of the present disclosure, the phage is a M13 phage or a T7 phage. Preferably, the phage is the M13 phage.

In the embodiments of the present disclosure, at least one of the plurality of phage-displayed scFvs is specific for a protein antigen selected from the group consisting of human epidermal growth factor receptor 2 (HER2, also known as EGFR2), maltose-binding protein (MBP), bovine serum albumin (BSA), human serum albumin (HSA), lysozyme, interleukin-1 beta (IL-1β), hemagglutinin of influenza virus (HA), nucleoprotein of influenza virus (NP), vascular endothelial growth factor (VEGF), epidermal growth factor receptor 1 (EGFR1), epidermal growth factor receptor 3 (EGFR3), glucagon receptor, human DNase I, programmed death-ligand 1 (PD-L1), sialic acid binding Ig-like lectin 3 (SIGLEC 3), immunoglobulin G (IgG)/Fragment crystallizable region (Fc region), and rituximab.

The second aspect of the present disclosure pertains to a method for generating the present phage-displayed scFv library. The method comprises the steps of:

(1) synthesizing a first nucleic acid sequence that comprises a first, a second, a third, a fourth, a fifth and a sixth coding sequences respectively encoding the CDR-L1, CDR-L2, CDR-L3, CDR-H1, CDR-H2, and CDR-H3 of an immunoglobulin gene;

(2) inserting the first nucleic acid sequence into a first phagemid vector;

(3) respectively modifying the first, second, and third coding sequences by site-directed mutagenesis to produce a variable light chain (VL) library that comprises a first group of phage-displayed scFvs with the modified CDR-L1, CDR-L2, and CDR-L3; and respectively modifying the fourth, fifth, and sixth coding sequences by site-directed mutagenesis to produce a variable heavy chain (VH) library that comprises a second group of phage-displayed scFvs with the modified CDR-H1, CDR-H2, and CDR-H3;

(4) screening the VL library with a protein L, and selecting a third group of phage-displayed scFvs therefrom; and screening the VH library with a protein A, and selecting a fourth group of phage-displayed scFvs therefrom;

(5) respectively amplifying a plurality of second nucleic acid sequences encoding the modified CDR-L1, CDR-L2, and CDR-L3 from the corresponding phages, and a plurality of third nucleic acid sequences encoding the modified CDR-H1, CDR-H2, and CDR-H3 from the corresponding phages; and (6) inserting the plurality of second and third nucleic acid sequences into a second phagemid vector so as to produce the present phage-displayed scFv library.

According to the embodiments of the present disclosure, the first, second, and third coding sequences are respectively modified by the nucleic acid sequences of SEQ ID NOs: 107-115, 116-119, and 120-127, and the fourth, fifth, and sixth coding sequences are respectively modified by the nucleic acid sequences of SEQ ID NOs: 128-131, 132-133, and 134-211 in step (3).

According to some embodiments of the present disclosure, the method further comprises the step of, comparing the distribution of aromatic residues of the CDR-H1, CDR-H2, CDR-H3, CDR-L1, CDR-L2, and CDR-L3 of the immunoglobulin gene with that of the corresponding CDR-H1, CDR-H2, CDR-H3, CDR-L1, CDR-L2, and CDR-L3 of a natural antibody prior to the step (3).

According to certain embodiments of the present disclosure, the immunoglobulin gene of the step (1) is derived from a mammalian, for example, a mouse, a rat, a hamster, a rabbit, a monkey, a goat, or a sheep. In one working example, the immunoglobulin gene is derived from the mouse. According to one preferred embodiment, the immunoglobulin gene encodes an antibody specific for VEGF.

According to the embodiment of the present disclosure, the first and second phagemid vectors can be the same or different. Optionally, both the first and second phagemid vectors are derived from the M13 phage.

The third aspect of the present disclosure is directed to a method of producing a recombinant antibody from the present phage-displayed scFv library, in which the recombinant antibody exhibits binding affinity and specificity to a protein antigen. The method comprises the steps of:

(a) screening the present phage-displayed scFv library with the protein antigen;

(b) selecting the phages that display scFvs with binding affinity and specificity to the protein antigen;

(c) respectively enabling the selected phages of the step (b) to express the scFvs, which are in soluble forms;

(d) selecting one soluble scFv from the scFvs of the step (c) that exhibits high binding affinity and specificity to the protein antigen;

(e) extracting a phagemid DNA from the phage that expresses the selected soluble scFv of the step (d);

(f) respectively amplifying a first nucleic acid sequence that encodes the CDR-H1, CDR-H2, and CDR-H3, and a second nucleic acid sequence that encodes the CDR-L1, CDR-L2, and CDR-L3 by polymerase chain reaction (PCR) using the phagemid DNA of the step (e) as a template; and (g) inserting the first and second nucleic acid sequences into an expression vector that comprises a third and a fourth nucleic acid sequences, wherein the third nucleic acid sequence encodes the constant region of the heavy chain of an immunoglobulin, and the fourth nucleic acid sequence encodes the constant region of the light chain of the immunoglobulin; and (h) transfecting a host cell with the expression vector of the step (g) that comprises the first, second, third, and fourth nucleic acid sequences so as to produce the present recombinant antibody.

In the embodiment of the present disclosure, the first nucleic acid sequence is disposed at the upstream of the third nucleic acid sequence, and the second nucleic acid sequence is disposed at the upstream of the fourth nucleic acid sequence.

According to one embodiment of the present disclosure, the immunoglobulin of the step (g) is selected from the group consisting of IgG, IgA, IgD, IgE, and IgM; preferably, it is IgG.

In one embodiment of the present disclosure, the host cell of the step (h) is a mammalian cell.

According to another embodiment of the present disclosure, the protein antigen is any of HER2, MBP, BSA, HSA, lysozyme, IL-1β, human DNase I, HA, NP, VEGF, EGFR1, EGFR3, PD-L1, SIGLEC 3, the Fc region of IgG, glucagon receptor, or rituximab.

The fourth aspect of the present disclosure pertains to a recombinant antibody prepared from the present phage-displayed scFv library. According to the embodiments of the present disclosure, the recombinant antibody comprises, (1) a CDR-L1 that has a type 2 CS and is encoded by a first coding sequence comprising the nucleic acid sequence of any of SEQ ID NOs: 2-10; (2) a CDR-L2 that has a type 1 CS and is encoded by a second coding sequence comprising the nucleic acid sequence of any of SEQ ID NOs: 11-14; (3) a CDR-L3 that has a type 1 CS and is encoded by a third coding sequence comprising the nucleic acid sequence of any of SEQ ID NOs: 15-22; (4) a CDR-H1 that has a type 1 CS and is encoded by a fourth coding sequence comprising the nucleic acid sequence of any of SEQ ID NOs: 23-26; (5) a CDR-H2 that has a type 2 CS and is encoded by a fifth coding sequence comprising the nucleic acid sequence of SEQ ID NOs: 27 or 28; and (6) a CDR-H3 that is encoded by a sixth coding sequence comprising the nucleic acid sequence of any of SEQ ID NOs: 29-106. According to the embodiments of the present disclosure, each of the CDR-H1, CDR-H2, CDR-H3, CDR-L1, CDR-L2, and CDR-L3 has a distribution of aromatic residues that is similar to the distribution of aromatic residues in the corresponding CDR-H1, CDR-H2, CDR-H3, CDR-L1, CDR-L2, and CDR-L3 of a natural antibody.

According to some embodiments of the present disclosure, the produced recombinant antibody has a dissociation constant ($K_D$) ranging from about $10^{-7}$ to about $10^{-11}$ M.

According to certain embodiments of the present disclosure, the produced recombinant antibody comprises the amino acid sequence at least 90% identical to any of SEQ ID NOs: 241-330.

Alternatively, the present disclosure also provides a recombinant antibody that is produced and purified from the HER2 immunized mouse. According to one embodiment, the recombinant antibody comprises the amino acid sequence at least 90% identical to any of SEQ ID NOs: 233, 237, or 331-334. Further, the mouse-derived recombinant antibody can be humanized and thus comprises the amino acid sequence at least 90% identical to SEQ ID NO: 235.

According to the embodiments, the present recombinant antibody (i.e., the recombinant antibody prepared from the present phage-displayed scFv library, the recombinant antibody produced from the HER2 immunized mouse, and the humanized recombinant antibody) is capable of specifically binding to an epitope of HER2. According to one embodiment, the present recombinant antibody induces the internalization of HER2 receptor. According to another embodiment, the present recombinant antibody inhibits the function of HER2 receptor.

Accordingly, the present invention also provides a method for treating a subject having or suspected of having a HER2-related disease; the method comprises administering to the subject a therapeutically effective amount of the present recombinant antibody so as to alleviate or ameliorate the symptom of the HER2-related disease. According to one embodiment of the present disclosure, the HER2-related disease is a tumor, and the treatment of the present recombinant antibody efficiently inhibits the tumor growth. Preferably, the subject is a human.

According to the preferred embodiments of the present disclosure, the recombinant antibody useful in treating the HER2-related disease comprises the amino acid sequence at least 90% identical to any of SEQ ID NOs: 233, 235, 237, or 241-330.

Another aspect of the present disclosure is directed to a composition for treating a HER2-related disease. According to the embodiments of the present disclosure, the composition comprises a first recombinant antibody and a second recombinant antibody, wherein both the first and second recombinant antibodies are prepared from the present phage-displayed scFv library. Preferably, the first recombinant antibody binds to a first epitope of HER2 and the second recombinant antibody binds to a second epitope of HER2. According to one specific embodiment of the present disclosure, the first recombinant antibody comprises the amino acid sequence of SEQ ID NO: 253, and the second recombinant antibody comprises the amino acid sequence of SEQ ID NOs: 274 or 301.

The present disclosure further provides a method for treating a subject having or suspected of having a HER2-related disease; the method comprises administering to the subject a therapeutically effective amount of the present composition so as to alleviate or ameliorate the symptom of the HER2-related disease. According to one embodiment of the present disclosure, the HER2-related disease is a tumor, and the treatment of the present composition efficiently inhibits the tumor growth. Preferably, the subject is a human.

According to the preferred embodiments of the present disclosure, the first recombinant antibody of the present composition comprises the amino acid sequence of SEQ ID NO: 253, and the second recombinant antibody of the present composition comprises the amino acid sequence of SEQ ID NOs: 274 or 301.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1A:
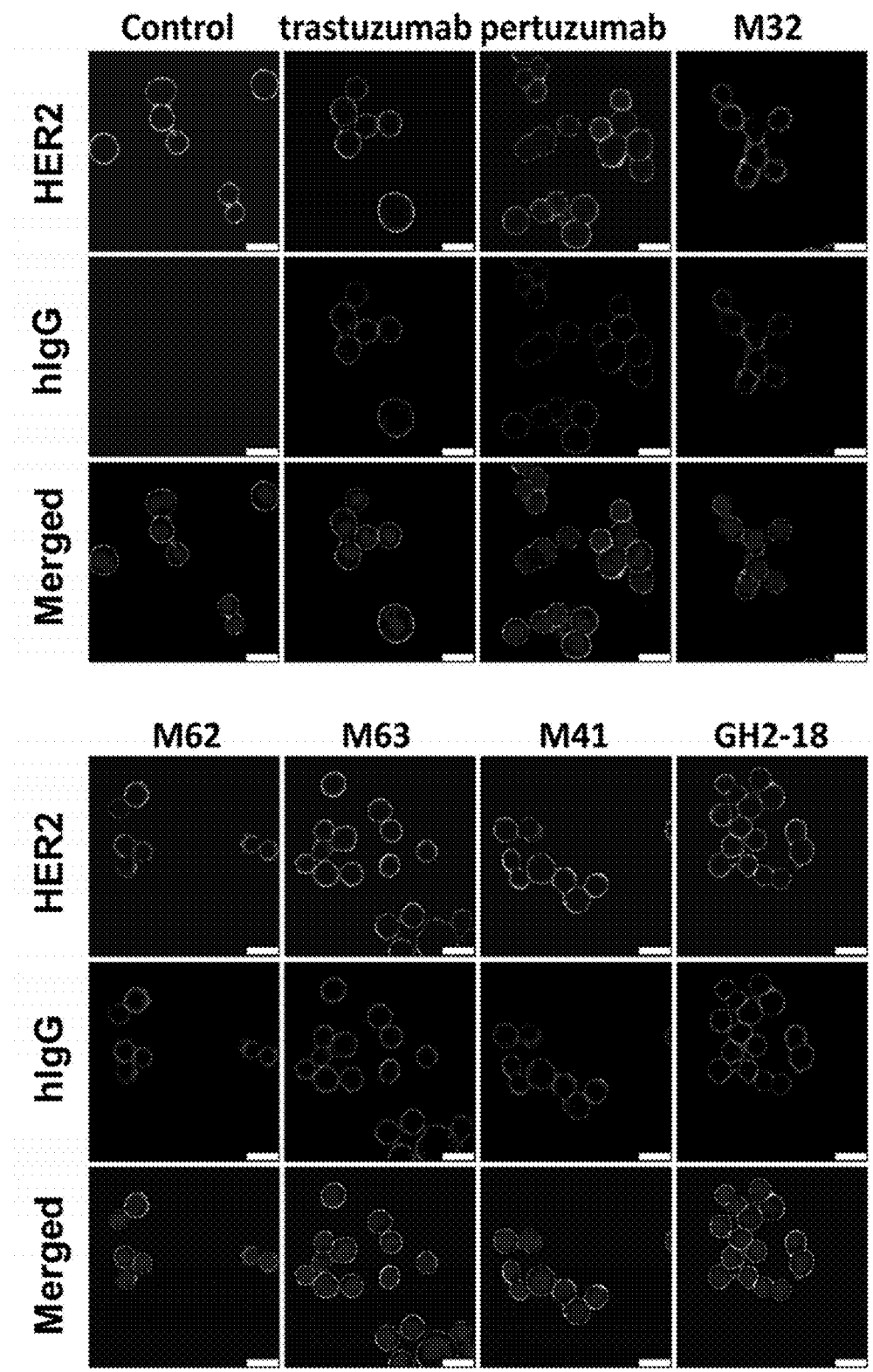
FIG. 1A are photographs of immunofluorescent staining that depict the SKBR3 cells respectively treated with specified antibodies according to example 3 of the present disclosure; the scale bar represents 25 μm.

In accordance with common practice, the various described features/elements are not drawn to scale but instead are drawn to best illustrate specific features/elements relevant to the present invention.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleic acid sequence or a partial nucleic acid sequence encoding a protein that elicits an immune response, therefore encodes an "antigen" as that term is used herein. Furthermore, one skilled in the art will understand that an antigen needs not be encoded solely by a full length nucleic acid sequence of a gene; it can also be encoded by partial nucleic acid sequences of more than one gene and that these nucleic acid sequences are arranged in various combinations to elicit the desired immune response. Moreover, a skilled artisan will understand that an antigen needs not be encoded by a "gene" at all; it is readily apparent that an antigen can be synthesized or can be derived from a biological sample. Such a biological sample can include, but is not limited to, a tissue sample, a tumor sample, a cell or a biological fluid.

The term "immunization" as used herein refers to a process known in the art for inducing an immune response in an animal by introducing an antigenic agent or substance into the animal (e.g., by injection, by mucosal challenge, etc.), which preferably results in a specific immune response to the antigenic agent or substance. The antigenic agent or substance can be introduced to the animal, with or without the use of adjuvants.

The term "antibody" is used in the broadest sense and specifically covers monoclonal antibodies (including full length monoclonal antibodies), polyclonal antibodies, multi-specific antibodies (e.g., bi-specific antibodies), and antibody fragments so long as they exhibit the desired biological activity. "Antibody fragments" comprise a portion of a full length antibody, generally the antigen binding or variable region thereof. Examples of antibody fragments include Fab, Fab', F(ab')2, and Fv fragments; diabodies; linear antibodies; single-chain antibody molecules; and multi-specific antibodies formed from antibody fragments.

The term "antibody library" refers to a collection of antibodies and/or antibody fragments displayed for screening and/or combination into full antibodies. The antibodies and/or antibody fragments may be displayed on a ribosome; on a phage; or on a cell surface, in particular a yeast cell surface.

As used herein, the term "single-chain variable fragment" or "scFv" is a fusion protein comprising the variable regions of the heavy (VH) and light chains (VL) of an immunoglobulin, in which the VH and VL are covalently linked to form a VH::VL heterodimer. The VH and VL are either joined directly or joined by a peptide-encoding linker, which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences.

The term "complementarity determining region" (CDR) used herein refers to the hypervariable region of an antibody molecule that forms a surface complementary to the 3-dimensional surface of a bound antigen. Proceeding from N-terminus to C-terminus, each of the antibody heavy and light chains comprises three CDRs (CDR 1, CDR 2, and CDR3). A HLA-DR antigen-binding site, therefore, includes a total of six CDRs that comprise three CDRs from the variable region of a heavy chain and three CDRs from the variable region of a light chain. The amino acid residues of CDRs are in close contact with bound antigen, wherein the closest antigen contact is usually associated with the heavy chain CDR3.

The term "canonical structure" (CS) as understood by those of ordinary skill in the art, refers to the main chain conformation that is adopted by the antigen binding (i.e., CDR) loops. From comparative structural studies, it has been found that five of the six antigen binding loops have only a limited repertoire of available conformations. Each canonical structure can be characterized by the torsion angles of the polypeptide backbone.

The term "$EC_{50}$," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, the term "association rate constant ($k_{on}$)" refers to a value representing the intensity (degree) of association of the antibody with the target antigen thereof, which is determined based on the kinetics of the antigen-antibody reaction. The term "dissociation rate constant ($k_{off}$)" refers to a value representing the intensity (degree) of dissociation of the antibody from the target antigen thereof, which is determined based on the kinetics of the antigen-antibody reaction. The term "dissociation constant ($K_d$)" is calculated by dividing the "dissociation rate constant ($k_{off}$)" with the "association rate constant ($k_{on}$)." These constants are used as indexes representing the affinity of an antibody for its antigen and its activity neutralizing the antigen.

The term "phagemid" refers to a vector, which combines attributes of a bacteriophage and a plasmid. A bacteriophage is defined as any one of a number of viruses that infect bacteria.

The terms "nucleic acid sequence", "nucleotide sequence", "polynucleotide" or "nucleic acid" can be used interchangeably and are understood to mean, according to the present disclosure, either a double-stranded DNA, a single-stranded DNA or a product of transcription of said DNA (e.g., RNA molecule). It should also be understood that the present disclosure does not relate to genomic polynucleic acid sequences in their natural environment or natural state. The nucleic acid, polynucleotide, or nucleic acid sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

All degenerate nucleotide sequences are included within the scope of the invention as long as the peptide/polypeptide/protein (e.g., the present CDR) encoded by the nucleotide sequence maintains the desired activity or function. The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The terms "coding sequence" and "coding region" as used herein are interchangeable and refer to nucleotide sequences and nucleic acid sequences, including both RNA and DNA, that encode genetic information for the synthesis of an RNA, a protein, or any portion of an RNA or protein. Nucleotide sequences that are not naturally part of a particular organism's genome are referred to as "foreign nucleotide sequences", "heterologous nucleotide sequences", or "exogenous nucleotide sequences". "Heterologous proteins" are proteins encoded by foreign, heterologous or exogenous nucleotide sequences and therefore are often not naturally expressed in the cell. A nucleotide sequence that has been isolated and then reintroduced into the same type (e.g., same species) of organism is not considered to be a naturally occurring part of a particular organism's genome and is therefore considered exogenous or heterologous.

The term "similar" or "similarity" as used herein describes the relationship between different nucleic acid or amino acid sequences in which the sequences are related by partial sequence identity or sequence similarity at one or more blocks or regions within the sequence. Such similar amino acid residues may be either identical between different amino acid sequences, or represent conservative amino acid substitutions between different sequences.

The object of the present disclosure aims at providing a phage-displayed scFv library that is capable of recognizing and binding to various antigen proteins, such as human epidermal growth factor receptor 2 (HER2). The scFv library comprises a plurality of phage-displayed scFvs, all of which are characterized in having: (1) a specific CS combination; (2) a specific distribution of aromatic residues in each CDR; and (3) a specific sequence in each CDR. Accordingly, an antibody exhibiting binding affinity and specificity to a specific antigen can be easily generated from the present library by antigen screening without the need of repeating the routine steps, such as immunizing a host animal and/or producing a hybridoma, thus may substantially shorten the time and efforts generally required for the production of an antibody via a conventional manner. Accordingly, the present method provides a means for generating various antigen-specific antibodies in accordance with the need of an experimental research and/or clinical applications.

To generate the present phage-displayed scFv library, the canonical structure (CS) combination of each scFv is first determined based on a mouse antibody repertoire. In one embodiment of the present disclosure, the method of establishing the mouse antibody repertoire comprises:

(A) immunizing a host animal with a protein antigen;

(B) isolating the splenocytes of the immunized mouse and extracting messenger ribonucleic acid (mRNA) from the isolated solenocytes;

(C) synthesizing the complementary deoxyribonucleic acid (cDNA) from the extracted mRNA;

(D) respectively amplifying a plurality of first nucleic acid sequences encoding the CDR-H1, CDR-H2, and CDR-H3 of the immunoglobulin genes, and a plurality of second nucleic acid sequences encoding the CDR-L1, CDR-L2, and CDR-L3 of the immunoglobulin genes, by PCR using the cDNA of the step (C) as templates;

(E) respectively inserting the plurality of first and second nucleic acid sequences into a phagemid vector to produce a phage library; and (F) sequencing the phage library of the step (E).

In step (A), a host animal such as a mouse, a rat, or a rabbit, is immunized with a protein antigen (e.g., a nature protein or a synthetic polypeptide) at suitable dose so as to induce the host animal to generate the antigen-specific antibody. According to one specific embodiment of the present disclosure, the host animal is first primed with a fusion protein of SEQ ID NO: 224, which comprises a maltose-binding protein (MBP) and a polypeptide comprising amino acid residues 203-262 of the extracellular domain (ECD) of HER2. Generally, adjuvant and the antigen are mixed together when immunizing the host animal. Examples of adjuvants useful for this invention include Freund's complete adjuvant (FCA), Freund's incomplete adjuvant (FIA), TiterMax, and aluminum hydroxide adjuvant.

According to one embodiment of the present disclosure, the fusion protein of SEQ ID NO: 224 is mixed with TiterMax. Immunization is generally carried out mainly by intravenous, intra-lymph node, subcutaneous, intra-peritoneal or intra-muscular injection of the antigen. According to another embodiment of the present disclosure, the mixture of the fusion protein of SEQ ID NO: 224 and the adjuvant TiterMax is injected into the inguinal lymph node. The immunization interval is not particularly limited. Immunization may be carried out at intervals of several days to several weeks, preferably 4 weeks, for 2 times. According to one specific example, the re-immunization was carried out by injecting the host with a polypeptide of SEQ ID NO: 225, which comprises the ECD of HER2 (i.e., HER2/ECD).

In step (B), total mRNA is extracted from the removed splenocytes of the immunized host animal of the step (A), which is subsequently converted to cDNA with the aid of reverse transcriptase in step (C). In the general extraction protocol familiar by one skilled artisan, the spleen isolated from the immunized host animal is first lysed in a chemical solution with high corrosiveness (e.g., phenol, trichloroacetic acid/acetone, and Trizol) followed by neutralization with chloroform. After centrifugation, the aqueous phase that contains the RNA sample is precipitated by an organic solution, such as ethanol and isopropanol. The RNA sample is then washed with ethanol to remove the contaminated protein followed by drying (e.g., air dry and vacuum dry) to obtain the RNA pellet.

In step (C), the RNA pellet obtained from the step (B) is dissolved in diethylpyrocarbonate-treated $H_2O$ (DEPC $H_2O$), and converted into the corresponding cDNA by reverse transcription (RT). In general, RT is performed by mixing the RNA with primer Oligo(dT)$_{20}$, deoxy-ribonucleoside triphosphate (dNTP, which comprises dATP, dGTP, dTTP, and dCTP), reverse transcriptase, reaction buffer, and optionally, the co-factor of reverse transcriptase (e.g., $MgCl_2$). Preferably, the reaction mixture further comprises dithiothreitol (DTT), a redox reagent used to stabilize the reverse transcriptase, and RNase inhibitor preventing the degradation of RNA during RT.

In step (D), the cDNA generated in step (C) is used as a template to amplify a target gene via PCR with a pair of target-specific primers. In one embodiment, the target gene is the first nucleic acid sequence, which encodes the CDR-H1, CDR-H2, and CDR-H3 of an immunoglobulin gene; while in another embodiment, the target gene is the second nucleic acid sequence, which encodes the CDR-L1, CDR-L2, and CDR-L3 of the same immunoglobulin gene. According to the embodiments of the present disclosure, the immunoglobulin is any of IgG, IgA, IgD, IgE, or IgM; preferably, the immunoglobulin is IgG. The first and second nucleic acids are respectively amplified by use of the primer mixes described by Barbas et al. (G. J. Phage Display A Laboratory Manual, Cold Spring Harbor Press, Cold Spring Harbor, N.Y.; 2001). Any skilled artisan will be able to select suitable primers for amplifying the desired first or second nucleic acid from an immunoglobulin gene without undue experimentation.

In step (E), the amplified first and second nucleic acid sequences are respectively inserted into a phagemid vector so as to produce a phage library that comprises a plurality of phages respectively displaying various scFvs. According to the method published by Barbas et al. (G. J. Phage Display A Laboratory Manual, Cold Spring Harbor Press, Cold Spring Harbor, N.Y.; 2001), the first and second nucleic acids are first assembled before being inserted into the phagemid; and the assembly is performed by overlap extension polymerase chain reaction (OE-PCR); also known as splicing by overlap extension PCR or splicing by overhang extension (both are abbreviated as SOE-PCR). In general, four primers are needed to exert OE-PCR, in which the first and second primers respectively serve as the forward and reverse primers for the first nucleic acid, and the third and fourth primers respectively act as the forward and reverse primers for the second nucleic acid. In comparison with other PCR reactions, the primers used in OE-PCR is specifically designed so that the second primer comprises a 3'-end overhang sequence (complementary sequence 1) that is complementary to the 5'-end overhang sequence (complementary sequence 2) of the third primer. In the first round of PCR, the first nucleic acid is amplified by the first and second primers, and the second nucleic acid is amplified by the third and fourth primer; accordingly, the complementary sequence 1 would be inserted into the 3'-end of the first nucleic acid, and the complementary sequence 2 would be inserted into the 5'-end of the second nucleic acid. In the second round of PCR, the two amplified nucleic acids are mixed and the PCR is performed by the first and fourth primers only. Since the complementary sequences 1 and 2 are complementary to each other, the 3'-end of the first nucleic acid and the 5'-end of the second nucleic acid would overlap, and thus, forming an intermediate template for PCR amplification exerted by the first and fourth primers. Based on this concept, the first nucleic acids amplified from the step (D) comprises the complementary sequences 1 (i.e., GGAAGATCTAGAGGAACCACC; SEQ ID NO: 335) at the 3' end, and the second nucleic acid comprises the complementary sequence 2 (i.e., GGTGGTTCCTCTAGATCTTCC; SEQ ID NO: 336) at the 5'-end, in which the two complementary sequences form an overlapping region so as to perform the assembly of the first and second nucleic acid sequences by the primers of SEQ ID NOs: 226 and 227. According to the embodiments of the present disclosure, the nucleic acid sequences of SEQ ID NOs: 226 and 227 respectively comprise a first and a second restriction enzyme sites that will facilitate the insertion of the assembled product into the multiple cloning sites of the phagemid vector to produce a recombinant phagemid. In one embodiment, the first restriction enzyme site is SfiI, and the second restriction enzyme site is NotI. The phagemid vector can be derived from a M13 phage or a T7 phage; preferably, it is derived from the M13 phage.

The recombinant phagemid is then introduced into a host cell. In general, the phagemid can be introduced into the host cell by transformation or electroporation; preferably, it is performed by electroporation. The host cell generally is a bacterial; for example, an *Escherichia coli* (*E. coli*) cell. Each transformed host cell that comprises one recombinant phagemid would form one colony on the culture plate; and according to the embodiments of the present disclosure, a total of about $10^9$ independent colonies are obtained from the step (E), all of which were scraped off the plates and storage in a storage buffer as a stock of the phage library.

In step (F), each scFv displayed by the phage library of the step (E) is analyzed by a sequencing assay. First, the recombinant phagemid is extracted from the phage library by any conventional DNA extraction technique; for example, the phenol/chloroform assay, and detergent (e.g., sodiumdodecyl sulfate, Tween-20, NP-40, and Triton X-100)/acetic acid assay. Then, the recombinant phagemid is sequenced by any of shotgun sequencing, single-molecule real-time sequencing, or next generation sequencing (NGS). According to one preferred example, the VL sequence of the phage library is determined by NGS using primers of SEQ ID NOs: 228 and 229, while the VH sequence of the phage library is determined by primers of SEQ ID NOs: 230 and 231.

According to the sequencing data that the predominant CS types of CDR-H1 and CDR-H2 are respectively type 1 and type 2, and the predominant CS types of CDR-L1, CDR-L2, and CDR-L3 are respectively type 2, type 1, and type 1, the antibodies of the present phage-displayed scFv library is thus constructed based on an antibody framework that possesses the CS combination of 1-2-2-1-1 for CDR-H1, CDR-H2, CDR-L1, CDR-L2, and CDR-L3 in sequence. Accordingly, one aspect of the present disclosure is directed to a method of establishing the phage-displayed scFv library of an antigen. The method comprises the steps of:

(1) synthesizing a first nucleic acid sequence that comprises a first, a second, a third, a fourth, a fifth and a sixth coding sequences respectively encoding the CDR-L1, CDR-L2, CDR-L3, CDR-H1, CDR-H2, and CDR-H3 of an immunoglobulin gene;

(2) inserting the first nucleic acid sequence into a first phagemid vector;

(3) respectively modifying the first, second, and third coding sequences by site-directed mutagenesis to produce a variable light chain (VL) library that comprises a first group of phage-displayed scFvs with the modified CDR-L1, CDR-L2, and CDR-L3; and respectively modifying the fourth, fifth, and sixth coding sequences by site-directed mutagenesis to produce a variable heavy chain (VH) library that comprises a second group of phage-displayed scFvs with the modified CDR-H1, CDR-H2, and CDR-H3;

(4) screening the VL library with a protein L, and selecting a third group of phage-displayed scFvs therefrom that exhibit binding affinity to the protein L; and screening the VH library with a protein A, and selecting a fourth group of phage-displayed scFvs therefrom that exhibit binding affinity to the protein A;

(5) respectively amplifying a plurality of second nucleic acid sequences encoding the modified CDR-L1, CDR-L2, and CDR-L3 from the corresponding phages, and a plurality of third nucleic acid sequences encoding the modified CDR-H1, CDR-H2, and CDR-H3 from the corresponding phages; and (6) inserting the plurality of second and third nucleic acid sequences into a second phagemid vector so as to produce the present phage-displayed scFv library.

In step (1), a first nucleic acid sequence, which serves as the backbone of the scFv of the present scFv library is first synthesized. As known by the skilled artisan, the synthesis step is performed in vitro without the need for initial template DNA samples. According to the embodiments of the present disclosure, the first nucleic acid sequence is least 90% identical to SEQ ID NO: 1 that encodes CDR-L1, CDR-L2, CDR-L3, CDR-H1, CDR-H2, and CDR-H3 of human anti-VEGF antibody. According to the embodiments of the present disclosure, the first nucleic acid sequence comprises a first and a second restriction enzyme sites that facilitate the insertion of the synthetic first nucleic acid sequence into the first phagemid vector as described in step (2). In one embodiment, the first restriction enzyme site is SfiI, and the second restriction enzyme site is NotI.

In step (2), the synthetic first nucleic acid sequence is inserted into the first phagemid vector via the first and second restriction enzyme sites. According to one embodiment of the present disclosure, the first phagemid vector can be derived from a M13 phage or a T7 phage; preferably, it is derived from the M13 phage.

To diversify the scFvs displayed by the phages, the first to sixth coding sequences respectively encoding the CDR-L1, CDR-L2, CDR-L3, CDR-H1, CDR-H2, and CDR-H3 are modified in step (3), in which the modification is performed by site-directed mutagenesis, a molecular biology method widely used by one of ordinary skill in the art to make specific and intentional changes to the genetic (i.e., DNA and RNA) sequence. Generally, the site-directed mutagenesis is exerted by a primer, which contains a desired mutation and the sequences complementary to the template DNA around the mutation site so that the primer can hybridize with the gene of interest; the mutation can be a single base change (a point mutation), multiple base changes, deletion, or insertion. In one embodiment of the present disclosure, the first to third coding sequences are respectively modified by the DNA segments having the nucleotide sequences of SEQ ID NOs: 107-115, 116-119, and 120-127; preferably, the first to third coding sequences are modified simultaneously. After the modification, the first coding sequence comprises any of the nucleotide sequences of SEQ ID NOs: 2-10; the second coding sequence comprises any of the nucleotide sequences of SEQ ID NOs: 11-14; and the third coding sequence comprises any of the nucleotide sequences of SEQ ID NOs: 15-22. The phage-displayed scFvs with the modified CDR-L1, CDR-L2, and CDR-L3 constitute the VL (variable light chain) library.

In another embodiment of the present disclosure, the fourth to sixth coding sequences are respectively modified by the DNA segments having the nucleotide sequences of SEQ ID NOs: 128-131, 132-133, and 134-211; preferably, the fourth to sixth coding sequences are modified simultaneously. After the modification, the fourth coding sequence comprises any of the nucleotide sequences of SEQ ID NOs: 23-26; the fifth coding sequence comprises the nucleotide sequence of SEQ ID NOs: 27 or 28; and the sixth coding sequence comprises any of the nucleotide sequences of SEQ ID NOs: 29-106. The phage-displayed scFvs with the modified CDR-H1, CDR-H2, and CDR-H3 constitute the VH (variable heavy chain) library.

The nucleotide sequences of SEQ ID NOs: 2-211 are represented by TUB (international unit of biochemistry) code, widely used by one of ordinary skill in the art, in which A represents adenine; C represents cytosine; G represents guanine; T represents thymine; B represents any nucleotide of C, G or T; D represents any nucleotide of A, T, or G; H represents any nucleotide of A, C, or T; K represents nucleotide G or T; M represents A or C; N represents any nucleotide of A, T, C, or G; R represents nucleotide A or G; S represents nucleotide G or C; V represents any nucleotide of A, C, or G; W represents nucleotide A or T; and Y represents nucleotide C or T.

Since the sequence mutation might affect the folding of scFv, the VL and VH libraries are respectively screened with protein L and protein A as described in step (4). As known by the skilled artisan, protein L is isolated from bacterial species *Peptostreptococcus magnus* and exhibits binding affinity to the light chain of an immunoglobulin; and protein A is isolated from the cell wall of bacterium *Staphylococcus aureus* and possesses binding affinity to the heavy chain of an immunoglobulin. In practice, the protein L and the protein A are respectively immobilized on a matrix (such as an agarose resin, and polyacrylamide) followed by respectively mixing with the phage-displayed scFvs of VL and VH library. The well-folded scFv would bind to the immobilized proteins, and can be collected by elution buffer, which generally is an acidic solution (such as glycine solution, pH 2.2) so as to disrupt the binding between immobilized protein and phage-display s. Accordingly, a third group of phage-displayed scFvs that possess well-folded light chains and binding affinity towards protein L can be selected from the VL library; and a fourth group of phage-displayed scFvs that possess well-folded heavy chains and binding affinity towards protein A can be selected from the VH library.

In step (5), the nucleic acid sequences of the third and fourth groups of phages are amplified by OE-PCR using primers of SEQ ID NOs: 212-215. Specifically, a plurality of second nucleic acid sequences that encode the modified CDR-L1, CDR-L2, and CDR-L3 are first amplified from the corresponding phages by primers of SEQ ID NOs: 212-213; and a plurality of third nucleic acid sequences that encode the modified CDR-H1, CDR-H2, and CDR-H3 are amplified from the corresponding phages by primers of SEQ ID NOs: 214-215. It is noted that two complementary sequences (i.e., GGAAGATCTAGAGGAACCACC and GGTGGTTC-CTCTAGATCTTCC; SEQ ID NOs: 335 and 336, respectively) are respectively comprised in the nucleic acid sequences of SEQ ID NOs: 213 and 214, which then would be respectively inserted into the 3'-end of the second nucleic acid sequences and the 5'-end of the third nucleic acid sequences. Based on the overlapping region mediated by the two complementary sequences, the second and third nucleic acid sequences form an intermediate template, and accordingly, these two nucleic acid sequences can be assembled by PCR using primers of SEQ ID NOs: 216 and 217.

According to one embodiment of the present disclosure, the nucleic acid sequences of SEQ ID NOs: 216 and 217 respectively comprise the first and second restriction enzyme sites (i.e., SfiI and NotI), and thus, in step (6), the assembled product could be inserted into the multiple cloning sites of a second phagemid vector via the two aforedescribed restriction enzymes so as to produce a recombinant phagemid. The second phagemid vector can be derived from a M13 phage or a T7 phage; preferably, it is derived from the M13 phage. The recombinant phagemid is then introduced into a host cell. In general, the phagemid can be introduced into the host cell by transformation or electroporation; preferably, it is performed by electroporation. After the recombinant phagemid is introduced into the host cell, each transformed host cell comprising one recombinant phagemid would form one colony on the culture plate. According to the embodiments, the host cell is a bacterial; for example, an *E. coli* cell; and a total of about $10^9$ independent colonies are obtained from the step (6), all of which were scraped off the plates and storage in a storage buffer as a stock of the phage-displayed scFv library of the present disclosure.

It should be noted that the first and second phagemid vector are not necessary to be the same. According to one embodiment of the present disclosure, both the first and second phagemid vectors are derived from M13 phage.

Accordingly, the generated phage-displayed scFv library comprises a plurality of phage-displayed scFvs, in which each of the plurality of phage-displayed scFvs comprises a CDR-H1, a CDR-H2, a CDR-H3, a CDR-L1, a CDR-L2, and a CDR-L3, wherein each of the CDR-H1, CDR-L2 and CDR-L3 has a type 1 CS, whereas each of the CDR-H2 and CDR-L1 has a type 2 CS; and each of the CDR-H1, CDR-H2, CDR-H3, CDR-L1, CDR-L2, and CDR-L3 has a distribution of aromatic residues that is similar to the distribution of aromatic residues in the corresponding CDR-H1, CDR-H2, CDR-H3, CDR-L1, CDR-L2, and CDR-L3 of a natural antibody.

According to the embodiments of the present disclosure, the CDR-L1 is encoded by a first coding sequence comprising the nucleic acid sequence of any of SEQ ID NOs: 2-10, the CDR-L2 is encoded by a second coding sequence comprising the nucleic acid sequence of any of SEQ ID NOs: 11-14, the CDR-L3 is encoded by a third coding sequence comprising the nucleic acid sequence of any of SEQ ID NOs: 15-22, the CDR-H1 is encoded by a fourth coding sequence comprising the nucleic acid sequence of any of SEQ ID NOs: 23-26, the CDR-H2 is encoded by a fifth coding sequence comprising the nucleic acid sequence of any of SEQ ID NOs: 27 or 28, and the CDR-H3 is encoded by a sixth coding sequence comprising the nucleic acid sequence of any of SEQ ID NOs: 29-106.

According to the embodiment, each phage of the present phage-displayed scFv library harbors one single phagemid.

In one embodiment of the present disclosure, at least one of the plurality of phage-displayed scFvs exhibits binding affinity and specificity to a protein antigen selected from the group consisting of HER2, MBP, BSA, HSA, lysozyme, IL-1β, HA, NP, VEGF, EGFR1, EGFR3, glucagon receptor, human DNase I, PD-L1, SIGLEC 3, IgG, and rituximab. According to some embodiments of the present disclosure, the protein antigen HA is derived from H1N1, H3N2 or H5N1. According to other embodiments of the present disclosure, the protein antigen NP is derived from H3N2 or H1N1. According to one working example of the present disclosure, at least one of the plurality of the phage-displayed scFvs exhibits binding affinity and specificity to the HER2; preferably, the HER2 is derived from human. In certain embodiments of the present disclosure, at least one of the plurality of phage-displayed scFvs is capable of binding to the extracellular domain (ECD) of HER2, EGFR1, EGFR3, PD-L1, SIGLEC 3, and/or glucagon receptor. In other embodiments of the present disclosure, at least one of the plurality of phage-displayed scFvs is capable of binding to the fragment crystallizable (Fc) region of IgG.

According to one embodiment, the scFvs displayed by the present phage-displayed scFv library are well-folded; particularly, they can be expressed on phage surfaces, or secreted as soluble form.

The established phage-displayed scFv library could be used to efficiently produce a recombinant antibody with binding affinity and specificity to a protein antigen. Specifically, the method of using the present phage-displayed scFv library to produce the recombinant antibody comprises the steps of:

(a) screening the present phage-displayed scFv library with the protein antigen;

(b) selecting phages that display scFvs with binding affinity and specificity to the protein antigen;

(c) respectively enabling the selected phages of the step (b) to express the scFvs, which are in soluble forms;

(d) selecting one soluble scFv from the scFvs of the step (c) that exhibits high binding affinity and specificity to the protein antigen;

(e) extracting a phagemid DNA from the phage that expresses the selected soluble scFv of the step (d);

(f) respectively amplifying a first nucleic acid sequence that encodes the CDR-H1, CDR-H2, and CDR-H3, and a second nucleic acid sequence that encodes the CDR-L1, CDR-L2, and CDR-L3 by PCR using the phagemid DNA of the step (e) as a template (g) inserting the first and second nucleic acid sequences into an expression vector that comprises a third and a fourth nucleic acid sequences, wherein the third nucleic acid sequence encodes the constant region of the heavy chain of an immunoglobulin, and the fourth nucleic acid sequence encodes the constant region of the light chain of the immunoglobulin; and (h) transfecting a host cell with the expression vector of the step (g) that comprises the first, second, third, and fourth nucleic acid sequences so as to produce the present recombinant antibody.

In step (a), the present phage-displayed scFv library is first screened with the protein antigen. With the similar screening method performed in afore-mentioned step (4), the protein antigen is first immobilized on a matrix (such as an agarose resin, and polyacrylamide) and mixed with the present phage-displayed scFv library. According to the embodiments of the present disclosure, the protein antigen can be any of HER2, MBP, BSA, HSA, lysozyme, IL-1β, HA, VEGF, EGFR1, EGFR3, glucagon receptor, or rituximab. In one specific embodiment, the protein antigen is HER2.

In step (b), the phage-displayed scFv that exhibit binding affinity and specificity to the protein antigen could be obtained by an elution buffer, which generally is an acidic solution (such as glycine solution, pH 2.2) so as to disrupt the binding between immobilized protein and phage-display antibody.

In step (c), to exclude the possibility that the binding of protein antigen is mediated by the phage, rather than the antibody, the phage-displayed scFv selected from the step (b) are respectively expressed as their secreted soluble forms. According to the embodiment of the present disclosure, the second and third nucleic acids constructed in the second phagemid as described in the step (6) are driven by a lactose operon (lac operon); as known by one skilled artisan, the lac operon would be induced by an isopropyl-thio-β-D-galactoside (IPTG) that then drives the expression of the down-stream genes (i.e., the second and third nucleic acid sequences). The produced scFv are then secreted into the supernatant of culture medium and could be collected thereof.

In step (d), the scFvs produced in step (c) are screened by the protein antigen. With the similar screening method performed in step (a), the protein antigen is first immobilized on a matrix (such as an agarose resin, and polyacrylamide) and then mixed with the scFvs. The scFv exhibiting high binding affinity and specificity to the protein antigen is selected. In the specific embodiment, the protein antigen is HER2.

In step (e), the phage that expresses the soluble scFv selected in step (d) was lysed and the phagemid DNA is extracted thereof. The lysis and extraction could be performed via any conventional DNA extraction technique; for example, the phenol/chloroform assay, and detergent (e.g., sodiumdodecyl sulfate, Tween-20, NP-40, and Triton X-100)/acetic acid assay.

In step (f), the phagemid DNA extracted in step (e) serves as a template to respectively amplifying the first nucleic acid sequence that encodes the CDR-H1, CDR-H2, and CDR-H3 by PCR using the primers of SEQ ID NOs: 220 and 221, and amplifying the second nucleic acid sequence that encodes the CDR-L1, CDR-L2, and CDR-L3 by PCR using the primer of SEQ ID NOs: 218 and 219.

In step (g), the amplified first and second nucleic acid sequences are inserted into an expression vector, which comprises a third nucleic acid sequence encoding the constant regions of the heavy chain of an immunoglobulin, and a fourth nucleic acid sequence encoding the constant regions of the light chain of the immunoglobulin. As could be appreciated, the immunoglobulin can be any of IgG, IgA, IgD, IgE, and IgM. In one preferred embodiment of the present disclosure, the immunoglobulin is IgG. Specifically, the first and second nucleic acid sequences are first linked by a linker, which is amplified from pIgG vector by PCR using primers of SEQ ID NOs: 222 and 223. According to the embodiment of the present disclosure, the linker comprises in sequence: a constant domain of light chain (CL), a bovine growth hormone (BGH) polyadenylation (polyA) signal, a human CMV promoter, and a signal peptide of IgG heavy chain. For the presences of the complementary sequences between the 3'-end of second nucleic acid sequence and the 5'-end of linker (i.e., TGCAGCCACCGTACGTTT-GATTTCCACCTT and AAGGTGGAAATCAAACG-TACGGTGGCTGCA; SEQ ID NOs: 337 and 338, respectively) and the complementray sequences between the 3'-end of the linker and the 5'-end of the first nucleic acid sequence (i.e., CTGCACTTCAGATGCGACACG and CGTGTCG-CATCTGAAGTGCAG; SEQ ID NOs: 339 and 340, respectively), the second nucleic acid sequence, the linker, and the first nucleic acid sequence can be assembled in sequence via OE-PCR using the primers of SEQ ID NOs: 218 and 221, which respectively comprise restriction enzyme sites, KpnI and NheI. The assembled product is then inserted into the expression vector pIgG by use of the restriction enzymes. Structurally, the constructed expression vector comprises in sequence: a first human cytomegalovirus (CMV) promoter, a signal peptide of IgG light chain, the second nucleic acid sequence, CL, a first BGH-polyA signal, a second human CMV promoter, a signal peptide of IgG heavy chain, the first nucleic acid sequence, CH, and a second BGH-polyA signal, in which the second nucleic acid sequence and CL are driven by the first human CMV promoter so as to express the light chain of the recombinant antibody, and the first nucleic acid sequence and CH are driven by the second human CMV promoter to express the heavy chain of the recombinant antibody.

In step (h), the expression vector constructed in step (g) is transfected into a host cell so as to produce the present recombinant antibody. The commonly used host cell is a mammalian cell such as a HEK293 Freestyle cell. The transfection can be performed by any method familiar by one skilled artisan, including chemical-based method (e.g., calcium phosphate, liposome, and cationic polymer), non-chemical method (e.g., electroporation, cell squeezing, sonoporation, optical transfection, protoplast fusion, and hydrodynamic delivery), particle-based method (e.g. gene gun, magnetofection, and impalefection), and viral method (e.g., adenoviral vector, sindbis viral vector, and lentiviral vector). The thus produced recombinant antibody is secreted into the supernatant of the culture medium, and can be purified therefrom by any purification method familiar by any skilled person; for example, the purification can be achieved by affinity binding with protein A or protein G.

According to some embodiments of the present disclosure, the present recombinant protein may exhibit binding affinity and specificity to the protein antigen selected from the group consisting of HER2, MBP, BSA, HSA, lysozyme, IL-1β, HA, NP, VEGF, EGFR1, EGFR3, glucagon receptor, human DNase I, PD-L1, SIGLEC 3, IgG/Fc region, and rituximab. According to some embodiments of the present disclosure, the protein antigen HA is derived from H1N1, H3N2 or H5N1. According to other embodiments of the present disclosure, the protein antigen NP is derived from H3N2 or H1N1. In certain embodiments of the present disclosure, at least one of the plurality of phage-displayed scFvs is capable of binding to the ECD of HER2, EGFR1, EGFR3, PD-L1, SIGLEC 3, and/or glucagon receptor. In other embodiments of the present disclosure, at least one of the plurality of phage-displayed scFvs is capable of binding to the fragment crystallizable (Fc) region of IgG.

Based on the method, a recombinant exhibiting binding affinity and specificity to the protein antigen can be produced. According to the embodiments of the present disclosure, the produced recombinant antibody comprises, (1) a CDR-L1 that has a type 2 CS and is encoded by a first coding sequence comprising the nucleic acid sequence of any of SEQ ID NOs: 2-10; (2) a CDR-L2 that has a type 1 CS and is encoded by a second coding sequence comprising the nucleic acid sequence of any of SEQ ID NOs: 11-14; (3) a CDR-L3 that has a type 1 CS and is encoded by a third coding sequence comprising the nucleic acid sequence of any of SEQ ID NOs: 15-22; (4) a CDR-H1 that has a type 1 CS and is encoded by a fourth coding sequence comprising the nucleic acid sequence of any of SEQ ID NOs: 23-26; (5) a CDR-H2 that has a type 2 CS and is encoded by a fifth coding sequence comprising the nucleic acid sequence of SEQ ID NOs: 27 or 28; and (6) a CDR-H3 that is encoded by a sixth coding sequence comprising the nucleic acid sequence of any of SEQ ID NOs: 29-106. According to the embodiments of the present disclosure, each of the CDR-H1, CDR-H2, CDR-H3, CDR-L1, CDR-L2, and CDR-L3 has a distribution of aromatic residues that is similar to the distribution of aromatic residues in the corresponding CDR-H1, CDR-H2, CDR-H3, CDR-L1, CDR-L2, and CDR-L3 of a natural antibody. In the embodiments, the present recombinant antibody has a dissociation constant ($K_D$) ranging from about $10^{-7}$ to about $10^{-11}$ M.

According to one embodiment of the present disclosure, the produced recombinant antibody comprises the amino acid sequence at least 90% identical to any of SEQ ID NOs: 241-330; that is, the recombinant antibody comprises the amino acid sequence that is 90%, 91%, 92%, 93%, 94%, 95%, 96%, 97%, 98%, 99%, or 100% identical to the sequence of SEQ ID NOs: 241-330. In one preferred example, the present recombinant antibody comprises the amino acid sequence 100% identical to the sequence of SEQ ID NOs: 241-330.

Alternatively, the present disclosure also provides a recombinant antibody that is produced and purified from the HER2 immunized mouse. According to one embodiment, the recombinant antibody comprises the amino acid sequence at least 90% identical to any of SEQ ID NOs: 233, 237, or 331-334; that is, the present recombinant antibody comprises the amino acid sequence that is 90%, 91%, 92%, 93%, 94%, 95%, 96%, 97%, 98%, 99%, or 100% identical to the sequence of SEQ ID NOs: 233, 237, or 331-334. In one preferred example, the present recombinant antibody comprises the amino acid sequence 100% identical to the sequence of SEQ ID NOs: 233, 237, or 331-334.

Further, the mouse-derived recombinant antibody can be humanized and thus comprises the amino acid sequence at least 90% identical to SEQ ID NO: 235; that is, the present recombinant antibody comprises the amino acid sequence that is 90%, 91%, 92%, 93%, 94%, 95%, 96%, 97%, 98%, 99%, or 100% identical to the sequence of SEQ ID NO: 235. In one preferred example, the present recombinant antibody comprises the amino acid sequence 100% identical to the sequence of SEQ ID NO: 235.

In the embodiments of the present disclosure, the present recombinant antibody is capable of specifically binding to an epitope of HER2. According to one embodiment, the recombinant antibody would cause the internalization and depletion of HER2, and thus, inhibit the HER2-associated signal transduction pathway.

For the inhibitory effect of the present recombinant antibody on HER expression, the present invention also provides a method for treating a subject having or suspected of having a HER2-related disease; the method comprises administering to the subject a therapeutically effective amount of the present recombinant antibody so as to alleviate or ameliorate the symptom of the HER2-related disease.

HER2 is a member of the human epidermal growth factor receptor (HER/EGFR/ERBB) family. Amplification or overexpression of this oncogene has been shown to play an important role in the development and progression of certain aggressive types of tumor; for example, the breast tumor. As the present recombinant antibody is capable of inhibiting the HER2 receptor function, it may provide a potential means to treat the disease caused by HER2 overexpression; such as the tumors. According to one embodiment of the present disclosure, the present recombinant antibody exhibits an inhibitory effect on the growth of HER-overexpressing tumor. According to another embodiment of the present disclosure, the subject is a mammalian; preferably, a human.

According to the embodiments of the present disclosure, the recombinant antibody useful in treating the HER2-related disease comprises the amino acid sequence at least 90% identical to any of SEQ ID NOs: 233, 235, 237, or 241-334.

Another aspect of the present disclosure is directed to a composition for the inhibition of HER2 expression. According to one embodiment of the present disclosure, the composition comprises a first recombinant antibody and a second recombinant antibody, wherein both the first and second recombinant antibodies are produced by the method of the present disclosure; and both the first and second recombinant antibodies are IgG antibodies. According to another embodiment of the present disclosure, the first recombinant antibody binds to a first epitope of HER2, and the second recombinant antibody binds to a second epitope of HER2, in which the first and second epitopes are not the same.

According to one embodiment of the present disclosure, the first recombinant antibody comprises the amino acid sequence of SEQ ID NO: 253, and the second recombinant antibody comprises the amino acid sequence of SEQ ID NO: 274. According to another embodiment of the present disclosure, the first recombinant antibody comprises the amino acid sequence of SEQ ID NO: 253, and the second recombinant antibody comprises the amino acid sequence of SEQ ID NO: 301.

According to some embodiments of the present disclosure, the composition induces the internalization of HER2 receptor. According to other embodiments of the present disclosure, the composition inhibits the function of HER2 receptor.

In certain embodiments of the present disclosure, the first and second antibodies exhibit an additive effect on the inhibition of HER2-associated signal transduction pathway; that means, the effect of the present composition is equal to the sum of the effect of the individual antibody (i.e., the first antibody and the second antibody). In other embodiments of the present disclosure, the first and second antibodies exhibit a synergistic effect on the inhibition of HER2-associated signal transduction pathway; that means, the effect of the present composition is greater than the sum of the effect of the individual antibody (i.e., the first antibody and the second antibody).

Based on the inhibitory efficacy of the present composition, the present disclosure further provides a method for treating a subject having or suspected of having a HER2- related disease; the method comprises administering to the subject a therapeutically effective amount of the present composition so as to alleviate or ameliorate the symptom of the HER2-related disease. In one specific embodiment of the present disclosure, the disease is tumor. According to one embodiment of the present disclosure, the subject is a mammalian; preferably, a human. In one preferred example, the present composition comprises two recombinant antibodies, in which one of the recombinant antibodies comprises the amino acid sequence of SEQ ID NO: 253, and the other of the recombinant antibodies comprises the amino acid sequence of SEQ ID NOs: 274 or 301.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Cell Line and Reagents

SKBR3 cells were obtained from the American Type Culture Collection (ATCC) and grown in RPMI 1640 (Gibco) with 10% fetal bovine serum and antibiotics/antimycotics. Heregulin (HRG) was purchased from R&D systems. Antibodies against phosphorylated ERK, ERK, phosphorylated AKT and AKT used in western blot analysis were obtained from Cell Signaling Technology; rabbit anti-HER2 and anti-tubulin antibodies were purchased from Sigma.

Mouse Immunization 8-12 weeks old female BalbC/j mice were bred and kept under approved SPF conditions. The mice were divided into 4 groups according to their immunization procedures: (1) group m0, which did not expose to any immunogen and thus, served as a control group; the mice of m0 group were sacrificed at the age of 16 weeks and their spleens were harvested and used in subsequent assays; (2) group m3, in which mice were first primed with a fusion protein MBP-#3 of SEQ ID NO: 224, which comprises a MBP and a polypeptide derived from amino acid residues 203-262 of ECD of human HER2 protein; and boosted with a polypeptide HER2/ECD of SEQ ID NO: 225; the mice of m3 group were sacrificed 5 weeks after the boost and their spleens were then harvested and used in subsequent assays; (3) group m4, in which mice were first primed with the fusion protein MBP-#3 followed by a boost with the polypeptide HER2/ECD; the mice of m4 group were sacrificed 12 weeks after the boost immunization, their spleens were harvested and used in subsequent assays; and (4) group m6, in which were immunized with the polypeptide HER2/ECD only, and were sacrificed 14 weeks after the immunization.

Establishment of Mouse Antibody Repertoire

Immunized mouse was sacrificed and its spleen was harvested and mixed with 2 mL TRI reagent (Invitrogen). Immediately, the sample was homogenized and dispensed into 1.5 mL microtubes (0.5 mL/tube) to be stored at −80° C. RNA extracted from thawed sample using QIAGEN RNeasy Plus Mini Kit was carried out to obtain 60-80 μg of total RNA from ¼ spleen. Reverse transcription (RT) of the extracted RNA was performed with SuperScript III First-Strand Synthesis System (Invitrogen) by following the manufacturer's protocol. The reaction was carried out as follows: 10 μg of total RNA, 1 μL of 10 μM primer Oligo(dT)$_{20}$, and 1 μL of 10 mM dNTP mix were added to each 0.2 mL tube and the total volume was adjusted to 10 μL with 0.1% diethylpyrocarbonate-treated H$_2$O (DEPC H$_2$O). The mixture was incubated at 65° C. for 5 min and immediately chilled on ice. 10 μL of cDNA synthesis mix (2 μL of 10× RT buffer, 4 μL of 20 mM MgCl$_2$, 2 μL of 0.1 M dithiothreitol (DTT), 1 μL of RNaseOut (40 U/μL) and 1 μL of SuperScript III RT (200 U/μL) was added to each tube. The mixture was incubated at 50° C. for 50 min to allow the synthesis of first strand of cDNA. The reactions was terminated by incubating at 85° C. for 5 min and then kept the tubes at 4° C. 1 μL of RNase H was added to the sample and incubated for 20 min at 37° C. to remove residual RNA. After quantitating the concentration at OD$_{260}$, the samples were stored at 20° C. until used for PCR.

In order to establish the mouse antibody repertoire, two rounds of PCR were performed. In the first round, the variable domains of light chain κ and λ (i.e., Vκ, Vλ), and the variable domain of heavy chain (i.e., VH) were respectively amplified from cDNA using the primer mixes according to the protocol published by Barbas (G. J. Phage Display A Laboratory Manual, Cold Spring Harbor Press, Cold Spring Harbor, N.Y.; 2001). PCR reactions were carried out in a volume of 50 μL containing MyTaq Hot Start polymerase (Bioline), 0.5 μg cDNA template, and 0.3 μM of each primer mix, and reactions were carried out for 25 cycles (30 sec 95° C., 30 sec 65° C., 1 min 72° C.) followed by a 10 min final synthesis step. The PCR products were checked and then purified by agarose gel electrophoresis.

In the second round of PCR, Vκ and Vλ were respectively assembled with VH by using the overlapping primers of SEQ ID NOs: 226 and 227. Briefly 100 ng of the recovered Vκ, Vλ and VH PCR fragments from the first round of PCR products were added to total volume of 50 μL containing MyTaq Hot Start polymerase (Bioline) and 0.3 μM of each primer, and 30 PCR cycles (30 sec 95° C., 30 sec 65° C., 1 min 30 sec 72° C.) followed by a 10 min final synthesis step were conducted. The assembled Vκ-VH or Vλ-VH fragment was doubly digested with SfiI and NotI (New England BioLabs) and cloned into phagemid vector pCANTAB5E. 10-5 μg ligation products were electroporated into Escherichia coli ER2738 at 3,000 V with an electroporator. The obtained mouse antibody repertoire comprises at least 10$^9$ scFv.

Analysis of CS Combination of Mouse Antibody Repertoire by Next Generation Sequencing (NGS)

To analyze the VL and VH sequences of each scFv-expressed antibody, DNA samples for NGS were prepared by PCR amplifications using the primers of SEQ ID NOs: 228 and 229 that flank the VL sequence and the primers of SEQ ID NOs: 230 and 231 that flank the VH sequence. The purified DNA fragments were sequenced with Roche 454 GS junior sequencer according to the titanium sequencing protocol.

The raw reads for the VH and VL sequences from control and immunized mice were respectively collected from NGS. These reads were first processed by Antibodyomics 1.0 package for sequence length filtering, and amino acid translation. For each antibody sequence, CDRs were defined by aligning the query sequence to the established heavy chain-specific or light chain-specific hidden Markov models (HMM) derived from 357 antibody structures. The phylogenetic analysis of VH and VL sequences was performed respectively with the MEGA program for phylogenetic tree building with the neighbor-joining method. The assignments of canonical structure of CDRs were performed by the abysis web site. The sequence LOGOs for each CDRs were created by WebLogo using the default background probabilities and parameters.

Establishment of the Present Phage-Displayed scFv Library (GH2)

Template Av1 Preparation

The nucleic acid sequence of SEQ ID NO: 1 that encoded the G6 anti-VEGF Fab was first synthesized in vitro, and cloned into the phagemid vector pCANTAB5E so as to generate a template Av1. Next, TAA stop codon was introduced into each CDR so as to ensure that only the antibodies carrying the modified genes would be expressed on the phage surface. The nucleic acid sequence of CDR-L1, CDR-L2, and CDR-L3 in the template Av1 were modified with 21 DNA segments respectively having nucleic acid sequences of SEQ ID NOs: 107-127 to produce a VL library, the nucleic acid sequence of CDR-H1, CDR-H2, and CDR-H3 in the template Av1 were modified with 27 DNA segments respectively having nucleic acid sequences of SEQ ID NOs: 128-154 to produce a VH2 library; the nucleic acid sequence of CDR-H1, CDR-H2, and CDR-H3 in the template Av1 were modified with 7 DNA segments respectively having nucleic acid sequences of SEQ ID NOs: 128-133, and 155 to produce a VH3 library; the nucleic acid sequence of CDR-H1, CDR-H2, and CDR-H3 in the template Av1 were modified with 8 DNA segments respectively having nucleic acid sequences of SEQ ID NOs: 128-133, and 156-157 to produce a VH4 library; the nucleic acid sequence of CDR-H1, CDR-H2, and CDR-H3 in the template Av1 were modified with 9 DNA segments respectively having nucleic acid sequences of SEQ ID NOs: 128-133, and 158-160 to produce a VH5 library; the nucleic acid sequence of CDR-H1, CDR-H2, and CDR-H3 in the template Av1 were modified with 10 DNA segments respectively having nucleic acid sequences of SEQ ID NOs: 128-133, and 161-164 to produce a VH6 library; the nucleic acid sequence of CDR-H1, CDR-H2, and CDR-H3 in the template Av1 were modified with 11 DNA segments respectively having nucleic acid sequences of SEQ ID NOs: 128-133, and 165-169 to produce a VH7 library; the nucleic acid sequence of CDR-H1, CDR-H2, and CDR-H3 in the template Av1 were modified with 12 DNA segments respectively having nucleic acid sequences of SEQ ID NOs: 128-133, and 170-175 to produce a VH8 library; the nucleic acid sequence of CDR-H1, CDR-H2, and CDR-H3 in the template Av1 were modified with 13 DNA segments respectively having nucleic acid sequences of SEQ ID NOs: 128-133, and 176-182 to produce a VH9 library; the nucleic acid sequence of CDR-H1, CDR-H2, and CDR-H3 in the template Av1 were modified with 16 DNA segments respectively having nucleic acid sequences of SEQ ID NOs: 128-133, and 183-192 to produce a VH11 library; the nucleic acid sequence of CDR-H1, CDR-H2, and CDR-H3 in the template Av1 were modified with 12 DNA segments respectively having nucleic acid sequences of SEQ ID NOs: 128-133, and 193-198 to produce a VH12 library; the nucleic acid sequence of CDR-H1, CDR-H2, and CDR-H3 in the template Av1 were modified with 9 DNA segments respectively having nucleic acid sequences of SEQ ID NOs: 128-133, and 199-201 to produce a VH13 library; nucleic acid sequence of CDR-H1, CDR-H2, and CDR-H3 in the template Av1 were modified with 9 DNA segments respectively having nucleic acid sequences of SEQ ID NOs: 128-133, and 202-204 to produce a VH14 library; the nucleic acid sequence of CDR-H1, CDR-H2, and CDR-H3 in the template Av1 were modified with 9 DNA segments respectively having nucleic acid sequences of SEQ ID NOs: 128-133, and 205-207 to produce a VH15 library; the nucleic acid sequence of CDR-H1, CDR-H2, and CDR-H3 in the template Av1 were modified with 8 DNA segments respectively having nucleic acid sequences of SEQ ID NOs: 128-133, and 208-209 to produce a VH16 library; and the nucleic acid sequence of CDR-H1, CDR-H2, and CDR-H3 in the template Av1 were modified with 8 DNA segments respectively having nucleic acid sequences of SEQ ID NOs: 128-133, and 210-211 to produce a VH17 library. To perform the modification, DNA segments corresponding to each CDR were first mixed and phosphorylated by T4 polynucleotide kinase (New England BioLabs) in 70 mM Tris-HCl (pH 7.6), 10 mM $MgCl_2$, 1 mM ATP and 5 mM dithiothreitol (DTT) at 37° C. for 1 h. The phosphorylated DNA segments were then annealed to uracilated single-stranded DNA template, at a molar ratio of 3:1 (oligonucleotide:ssDNA), by heating the mixture at 90° C. for 2 min, followed by a reduction in temperature at the rate of 1° C./min until it reached 20° C. in a thermal cycler. Subsequently, the template-primer annealing mixture was incubated with 0.32 mM ATP, 0.8 mM dNTPs, 5 mM DTT, 600 units of T4 DNA ligase, and 75 units of T7 DNA polymerase (New England BioLabs) to prime in vitro DNA synthesis. After overnight incubation at 20° C., the synthesized dsDNA was desalted and concentrated by a centrifugal filter (Amicon® Ultra 0.5 mL 30K device), then electroporated into *Escherichia coli* ER2738 at 3,000 V with an electroporator. Typically, 1 μg of dU-ssDNA produced about $10^7$-$10^8$ recombinant variants (scFv variants), and 75-90% of the scFv variants carried modifications at three CDR regions simultaneously.

Protein A and Protein L Selection of Functional scFv Variants

The VL library (i.e., scFv variants with modification in CDR-L1, CDR-L2, and CDR-L3) was screening by protein L, and the VH2-VH9 libraries and the VH11-VH17 libraries (i.e., scFv variants with modification in CDR-H1, CDR-H2, and CDR-H3) were screening by protein A. To exert the selection, respective scFv variants of VL, VH2-VH9, and VH11-VH17 libraries were precipitated with 20% PEG/NaCl and resuspended in phosphate-buffered saline (PBS); meanwhile, a 96-well Maxisorb immunoplate was coated at 4° C. overnight with protein A or protein L (1 μg/100 μL PBS per well) followed by blocking with 5% skim milk in PBS-T (0.05% Tween-20 in PBS) for 1 h. Then, 100 μL of the resuspended scFv variants ($10^{13}$ cfu/mL) were added to each well for 1 h with gentle shaking. The plate was washed 12 times with 200 μL PBST and 2 times with 200 μL PBS. The bound variants were eluted with 100 μL of 0.1 M HCl/glycine (pH 2.2) per well, followed by neutralization with 8 μL of 2 M Tris-base buffer (pH 9.1). The eluted scFv variants were mixed with 1 mL of *E. coli* strand ER2738 ($A_{600\ nm}$=0.6) for 15 min at 37° C. The *E. coli* was titrated, and amplified with 50 mL of 2× Yeast extract and Tryptone medium (YT medium) containing 100 μg/mL ampicillin at 37° C. overnight. After centrifugation, the bacterial pellet was resuspended and its phagemid DNA was extracted for the following assays.

Combination of Functional scFv Variants into the GH2 Library

The phagemid DNA extracted from the variants of VL library was used as a template to amplify the nucleic acid sequences of VL by using the forward primer having nucleic acid sequence of SEQ ID NO: 212 and the reverse primer having nucleic acid sequence of SEQ ID NO: 213; while those from the variants of VH library (i.e., VH2-VH9, and VH11-VH17) were used to amplify the nucleic acid sequences of VH via using the forward primer having nucleic acid sequence of SEQ ID NO: 214, and the reverse primer having nucleic acid sequence of SEQ ID NO: 215. PCR reactions were performed in a volume of 50 µL containing KOD Hot Start polymerase (Novagen), 100 ng DNA template, and 0.3 µM of each primers, and 25 PCR cycles (30 sec 95° C., 30 sec 65° C., 1 min 72° C.) followed by a 10 min final synthesis step were conducted. The PCR products were digested with EcoRI and then purified by agarose gel electrophoresis.

Another PCR was then performed to assemble the nucleic acid sequences of VL and VH by two primers respectively having nucleic acid sequences of SEQ ID NOs: 216 and 217. In the second round PCR, 100 ng of the purified VL and VH PCR products of the first round PCR were added to a total volume of 50 µL containing MyTaq Hot Start polymerase (Bioline) and 0.3 µM of each primers, and 30 PCR cycles (30 sec 95° C., 30 sec 65° C., 1 min 30 sec 72° C.) followed by a 10 min final synthesis step were conducted. The assembled VL-VH fragments were doubly digested with SfiI and NotI (New England BioLabs) and cloned into the phagemid vector pCANTAB5E. The resulting ligation product was electroporated into Escherichia coli ER2738 at 3,000 V with an electroporator.

The obtained phage-express scFv libraries were named GH2 (generic human, version 2)-GH9, and GH11-GH17, which respectively comprise the phages expressing specified VL and VH sequence as listed in Table 1.

TABLE 1

The CDR sequences of specified libraries

| Library | SEQ ID NO |  |  |  |  |  |
|---|---|---|---|---|---|---|
|  | CDR-L1 | CDR-L2 | CDR-L3 | CDR-H1 | CDR-H2 | CDR-H3 |
| GH2 | 2-10 | 11-14 | 15-22 | 23-26 | 27-28 | 29-49 |
| GH3 | 2-10 | 11-14 | 15-22 | 23-26 | 27-28 | 50 |
| GH4 | 2-10 | 11-14 | 15-22 | 23-26 | 27-28 | 51-52 |
| GH5 | 2-10 | 11-14 | 15-22 | 23-26 | 27-28 | 53-55 |
| GH6 | 2-10 | 11-14 | 15-22 | 23-26 | 27-28 | 56-59 |
| GH7 | 2-10 | 11-14 | 15-22 | 23-26 | 27-28 | 60-64 |
| GH8 | 2-10 | 11-14 | 15-22 | 23-26 | 27-28 | 65-70 |
| GH9 | 2-10 | 11-14 | 15-22 | 23-26 | 27-28 | 71-77 |
| GH11 | 2-10 | 11-14 | 15-22 | 23-26 | 27-28 | 78-87 |
| GH12 | 2-10 | 11-14 | 15-22 | 23-26 | 27-28 | 88-93 |
| GH13 | 2-10 | 11-14 | 15-22 | 23-26 | 27-28 | 94-96 |
| GH14 | 2-10 | 11-14 | 15-22 | 23-26 | 27-28 | 97-99 |
| GH15 | 2-10 | 11-14 | 15-22 | 23-26 | 27-28 | 100-102 |
| GH16 | 2-10 | 11-14 | 15-22 | 23-26 | 27-28 | 103-104 |
| GH17 | 2-10 | 11-14 | 15-22 | 23-26 | 27-28 | 105-106 |

Production of Recombinant Antibody from GH2-GH9 and GH11GH17 Libraries

For IgG expression, the nucleic acid sequences encoding VH and VL were amplified from the phagemid, which was extracted from the GH2-GH9, and GH11-GH17 libraries, by PCR, and then cloned into mammalian expression vector pIgG. The VL sequence was amplified by PCR with proof-reading DNA polymerase (KOD Hot Start DNA polymerase, Novagen) using primers of SEQ ID NOs: 218 and 219; as to the amplification of the VH sequence, primers of SEQ ID NOs: 220 and 221 were used. PCR reactions were performed in a volume of 50 µL with 100 ng DNA template and 1 µL of 10 µM of each primer for 30 cycles (30 sec for 95° C., 30 sec for 56° C., 30 sec for 72° C.) followed a 10 min final synthesis step at 72° C. The VL and VH sequences were linked by a linker, which was amplified from pIgG vector by PCR using primers of SEQ ID NOs: 222 and 223. The linker comprised in sequence: a constant domain of light chain (CL), a bovine growth hormone (BGH) polyadenylation (polyA) signal, a human CMV promoter, and a signal peptide of IgG heavy chain. To assemble the VL sequence, linker, and VH sequence, PCR was conducted with a pair of primers of SEQ ID NOs: 218 and 221 for 30 cycles (30 sec for 95° C., 30 sec for 58° C., 90 sec for 72° C.). The PCR products were cloned into pIgG vector. Briefly, 2 µL (20 ng) of linearized pIgG vector (digested by KpnI and NheI previously) and 2 µL (20 ng) DNA to be inserted were mixed with 4 µL Gibson Assembly Master Mix (New England BioLabs Inc. Ipswich, Mass., USA) and incubated at 50° C. for 1 hour. Then, half the volume of the ligation mixture was used to transform Escherichia coli JM109 competent cells. The DNA insertion in the plasmid was confirmed by restriction enzyme digestion and DNA sequencing. The obtained construct contained both light chain and heavy chain of IgG, respectively controlled by human CMV promoter.

The construct was then transfected into HEK293 Freestyle (293-F, Life Technologies, USA) cells, which were grown in serum free Freestyle 293 expression media (Life Technologies) at 37° C. with gentle shaking (110 rpm) in a 7% CO$_2$ incubator (Thermo Scientific). To transfect 500 mL cell culture, the density of 293-F cells suspended in 2-L Erlenmeyer flasks were adjusted to be $1.0 \times 10^6$ cells/mL. The plasmid DNA (500 µg), diluted in 25 mL serum free medium and sterile with 0.2 µm syringe filter, was mixed vigorously with 25 mL medium containing 1 mg of polyethylenimine (PEI, Polysciences). After 20 min incubation at room temperature, the mixture was added to the cells with slight shaking, and then the cells were left to culture at 37° C. Tryptone N1 (ST Bio, Inc, Taipei, Taiwan) was added to the culture at a final concentration of 0.5% after 24 hr post-transfection. After being cultured for 5 days, the supernatant was collected by centrifugation at 8000×g for 30 min and filtered with 0.8 µm membrane filter (Pall Corporation, Michigan). The supernatant was loaded onto HiTrap Protein A affinity column (GE Healthcare, Uppsala, Sweden), and eluted with 0.2 N glycine-HCl at pH 2.5 into 1/10 volume of 1 M Tris-HCl buffer at pH 9.1. The IgG proteins were further purified with Superdex 200 gel filtration column (10/300 GL, GE Healthcare, Uppsala, Sweden) to remove high molecular weight aggregates.

Competition Assay

The NUNC 96-well Maxisorb immunoplates were coated with HER2/ECD peptides (0.2 µg per well) in PBS buffer (pH7.4) by incubating overnight at 4° C., the plates were then blocked with 5% skim milk in PBST for 1 h. After blocking, 1-3 µg purified scFv or IgG antibody were added to each well for 30 min under gentle shaking and then 50 µL test phages were added while the incubation continued for another hour. Each plate was washed 6 times with 300 µL PBST [0.05% (v/v) Tween 20] and incubated 30 min with horse-radish peroxidase/anti-M13 antibody conjugate (1:2000 dilution) and horse-radish peroxidase/anti-E-tag antibody conjugate (1:3000 dilution). The plates were washed 6 times with PBST buffer and twice with PBS, developed for 5 min with 3,3',5,5'-tetramethyl-benzidine peroxidase substrate (Kirkegaard & Perry Laboratories), quenched with 1.0 M HCl and read spectrophotometrically at 450 nm. Competition values were calculated by comparing each control sample without adding scFvs antibody or IgG antibody. For competition analysis, the gplots package of R software was used for generating the heat map with a dendrogram for the competition data where the competition values were normalized from 0 to 100.

BIAcore Assay

BIAcore T200 (GE Healthcare) instrument was used to determine the binding affinities and kinetic parameters for interactions between antibody and antigen HER2/ECD. HER2/ECD in 10 mM acetate buffer (pH 5.0) was immobilized on a CM5 sensor chip to a response unit (RU) of 1000 with an amine coupling kit. Association ($k_{on}$) and dissociation ($k_{off}$) constants of the interactions between IgGs and HER2/ECD were measured in PBST running buffer (0.05% Tween 20) with a flow rate of 30 µL/min. The sensor surface was regenerated with 10 mM Glycine, pH 1.5, prior to a new IgG injection and the signals obtained were subtracted by that obtained from the reference channel that had not been coated with ligands. Binding kinetics was determined by global fitting to 1:1 binding model using the Biaevaluation software (GE Healthcare).

Epitope Mapping

For HDX-MS (hydrogen-deuterium exchange measured with LC-tandem mass spectroscopy) epitope mapping, deuterated antigen-antibody complex, deuterated antigen and non-deuterated antigen were prepared. In deuterated antigen-antibody complex preparation, antigen-antibody complex in 1:2 molar ratio was prepared by mixing 1.1 mg/mL of HER2/ECD with 6 mg/mL of antibody and incubation at room temperature for 1 hr. The proteins was deglycaned by incubating the samples with 2 µg deglycan enzyme-PNGase (P0704S, NEB) at 37° C. for 2 hr so as to increase the sequence coverage determined by mass spectrometry. Deuteration of the sample was carried out by mixing 5 µL of antigen or antigen-antibody complex with 20 µL of deuteration buffer (100% $D_2O$, 10 mM TRIS, 140 mM NaCl, pH 7.2) followed by a 10 min exchange incubation at room temperature. The exchange reaction was quenched by the addition of 75 µL of iced pre-chilling quench solution (0.15% formic acid, 8 M urea, 1 M TCEP, pH 2.5) and reduced the sample volume to 20 µL using centrifugal concentrator (Vivaspin 500, 10 kDa, GE Healthcare) at a speed of 7,500 rpm at 0° C. Denatured sample was diluted by the addition of 40 µL pre-chilling acid solution (0.15% formic acid, 100 mM TCEP, pH 2.5) to reduce urea concentration, and then double digested by incubating the sample with 3 µL of pepsin (5 mg/mL) and 3 µL of protease type XIII (50 mg/mL) on ice for 30 min. Digested sample was immediately frozen by liquid nitrogen and stored at 80° C. Non-deuterated antigen was prepared without the deuteration step.

To determine the peptide mass, the samples were thawed and then immediately injected 10 µL of the thawed samples into a tandem liquid chromatographic system (Accela pump, Thermo Scientific) coupled with ESI mass spectrometry (Velos Pro LTQ, Thermo Scientific) for separation and analyses. The separation was carried out using a $C_{18}$ column (XBridge $C_{18}$, 3.5 µm, 1.0×150 mm, Waters) with a linear gradient from 10% to 60% solvent B (solvent A: water, 0.15% formic acid; solvent B: acetonitrile, 0.1% formic acid) for 30 min at a flow rate of 50 µL/min. The $C_{18}$ column, injector and tube were submerged in an ice bath for reducing back-exchange. Mass spectra were collected in resolution mode (m/z 300-2,000) from a mass spectrometer equipped with a standard electrospray ionization source. The centroid value of each peptide isotopic envelope was measured using HX-Express 2[9]. The deuteration level of each peptide fragment from the antigen was determined by Equation (1):

$$\text{Deuteration Level (\%)} = 100 - 100 \times [m(P) - m(N)] / [m(F) - m(N)] \quad (1);$$

wherein m(P), m(N), and m(F) are the centroid values for a given deuterated antigen-antibody complex, non-deuterated antigen, and deuterated antigen, respectively. Only changes in deuteration level greater than 10% are considered to be the binding site.

$EC_{50}$ for Antibody-Antigen Interactions

The $EC_{50}$ of antibody was determined by titrating the antibody on immobilized HER2/ECD with ELISA. Briefly, NUNC 96-well Maxisorb immunoplates were coated with HER2/ECD peptides (0.2 µg per well) in PBS buffer (pH 7.4) via overnight incubation at 4° C., the plates were then blocked with 5% skim milk in PBST [0.05% (v/v) Tween 20] for 1 h. In the meantime, twofold serial dilutions of the antibody in PBST with 5% milk were performed and 11 different concentrations of the antibody were generated. After blocking, 100 µL diluted antibody samples were added to each well, and incubated for 1 h under gentle shaking. The plate was washed 6 times with 300 µL PBST and then added with 100 µL 1:2000-diluted horse-radish peroxidase/anti-human IgG antibody conjugate in PBST with 5% milk for 1 h incubation. The plates were washed 6 times with PBST buffer and twice with PBS, developed for 3 min with 3,3',5,5'-tetramethyl-benzidine peroxidase substrate (Kirkegaard & Perry Laboratories), quenched with 1.0 M HCl and read spectrophotometrically at 450 nm. The $EC_{50}$ (ng/mL) was calculated according to Stewart and Watson method.

Immunofluorescent Staining

SKBR3 cells seeded in Lab-Tek II chamber slides (Nunc) were allowed to grow overnight, then treated with antibodies for the indicated time at 37° C. before fixation by methanol. Fixed cells were permeabilized by TBS-Tx (TBS with 0.1% triton X-100) and blocked in blocking buffer (2% BSA in TBS-Tx) for 10 minutes at room temperature. Next, cells were incubated with primary antibody in blocking buffer at 4° C. overnight, washed, incubated with secondary antibodies (Alexa-488-conjugated goat anti-rabbit; Invitrogen and Alexa-647-conjugated goat anti-human) in blocking buffer for 60 minutes at room temperature, washed, and mounted with mounting medium with DAPI (Life Technologies). Slides were examined using a TCS-SP5-MP-SMD confocal microscope (Leica) equipped with 40× and 100× apochromat objectives. Alexa fluorophores were excited at 488 nm and 647 nm by Argon and NeHe laser respectively. Images were processed using the LAS AF Software software (Leica).

Western Blot Analysis

Cell lysates from antibody-treated cell and mock cell were respectively subjected to SDS-PAGE, transferred to PVDF membranes. These blots were blocked with 5% nonfat milk powder in TBS-0.1% Tween-20 for 30 minutes, followed by incubation with primary antibodies at 4° C. overnight and then horseradish peroxidase-conjugated secondary antibodies (Amersham Biosciences, Piscataway). Imaging of bands was performed using Pierce ECL Western Blotting Substrate (Thermo Fisher Scientific) and ImageQuant LAS-4000 (GE Healthcare).

Pseudovirus Neutralization Assay

The H1N1 pseudovirus was produced by co-transfection lentiviral core plasmid encoding luciferase and plasmids encoding HA, NA and TMPRSS2 proteins (A/California/04/2009). Prepare 293T cells at a final concentration of $2 \times 10^5$ cell/ml. Seed 50 µl 293T cells per well of 96 well plate. Thus, each well contains 10,000 cells. Incubate cells for 18 hours at 37° C. $CO_2$ incubator. Prepare sterile scFv by going through 0.45 µm 96 well Filter plate (PALL corp.). Prepare serial dilution of scFv in 0.3% BSA MEM medium (Gibco). Neutralization assays were performed by incubating 80 μl H1N1 pseudovirus with 80 μl diluted scFv at 37° C. $CO_2$ incubator for 45 minutes. After removing culture medium of 293T cells plated 18 hours before test, the mixture was then added into cells and incubated for 10-12 hours at 37° C. $CO_2$ incubator. After incubation, pseudovirus/scFv mixture was replaced with fresh DMEM (Gibco) containing 10% FBS (Gibco). Cells were cultured for additional 48 hours. To develop luciferase assay, culture medium was removed from cells. Cells were lysed by 20 μl lysis buffer (Promega)/well and mixed by shaking in a shaker for 15 minutes. Add 50 μl luciferase reagent (Promega) to each well of white 96 well microplate (Griener Bio-one). Transfer cell lysate to corresponding well of white 96 well microplate. Analyze luciferase activity of the plate in Victor3 (Perkin Elmer).

Example 1 Analysis of Mouse Antibody Repertoire

To analyze the mouse antibody repertoire, the mRNAs respectively extracted from the mice of groups m0, m3, m4, and m6 (as described in "Materials and Methods" section) were converted into their corresponding cDNAs and served as templates to amplify the VH and VL sequences, in which the VH sequence comprised the $V_H$-$D_H$-$J_H$ DNA segment, the Vκ sequence comprised the Vκ-Jκ DNA segment, and the Vλ sequence comprised the Vλ-Jλ DNA segment. The amplified VH and VL sequences were respectively inserted into a phagemid vector pCANTAB5E, which was then used to transform E. coli ER2738 strain to amplify the phage expressing the scFv. 316 phages that expressed scFv exhibiting binding affinity to peptide HER2/ECD were selected and designated as S316.

The CS type of each CDR was analyzed by NGS, and the analysis data indicated that the CS types of VH, Vκ, and Vλ were all similar among the 4 groups of mice and S316, in which the predominant CS types of CDR-H1 and CDR-H2 respectively belonged to type 1 and type 2, the predominant CS types of CDR-Lκ1 and CDR-Lκ2 respectively belonged to type 2 and type 1, and only one CS combination was observed in the CDR-Vλ (data not shown). The data also implied that neither the differences of the immunization protocol nor the antibody selection procedure would affect the distribution of an antibody repertoire. It is known that Vκ dominated the VL in mouse antibody repertoire, and that the CDR-L3 distributions of Vκ were predominantly centered at the length of 9 residues, in which the CDR-L3 predominantly belonged to type 1 CS (data not shown). Thus, all the antibody repertoires exhibited a predominant CS combination: type 1 CS for CDR-H1, type 2 CS for CDR-H2, type 2 CS for CDR-L1, type 1 CS for CDR-L2, and type 1 CS for CDR-L3. As to CDR-H3, although the CS was not characterized by a specific type, its length distribution centered at 11 residues.

The data indicated that the mouse antibody repertoire comprises at least $10^9$ scFv, in which the predominant CS types of CDR-H1 and CDR-H2 are respectively type 1 and type 2, and the predominant CS types of CDR-L1, CDR-L2, and CDR-L3 are respectively type 2, type 1, and type 1.

Example 2 Establishment of the Present Antibody Libraries GH2-GH9 and GH11-GH17

2.1 Construction and Modification

Based on the analysis result of Example 1 that the mouse antibody repertoire possessed a CS combination of 1-2-2-1-1 respectively for CDR-H1, CDR-H2, CDR-L1, CDR-L2, and CDR-L3, the nucleic acid sequence of SEQ ID NO: 1 that encoded G6 anti-VEGF Fab was synthesized and cloned into the phagemid vector pCANTAB5E to generate the recombinant phagemid Av1. The distributions of aromatic residues of CDR-H1, CDR-H2, CDR-H3, CDR-L1, CDR-L2, and CDR-L3 of the recombinant phagemid Av1 were similar to those of the antibody repertoires respectively derived from 4 groups of mice (i.e., m0, m3, m4, and m6), S316, and 584 antibodies published on Protein Data Bank (i.e., S584) (data not shown).

As the short-chain hydrophilic residues in CDRs mediate the antigen-recognition specificity through short range electrostatic interaction and direct hydrogen bonding across antibody-antigen interfaces, the nucleic acid sequences of CDR-L1, CDR-L2, and CDR-L3 of the antibody library recombinant phagemid Av1 were modified with 21 DNA segments respectively having nucleic acid sequences of SEQ ID NOs: 107-127 to produce a VL library, while the nucleic acid sequences of CDR-H1, CDR-H2, and CDR-H3 in the antibody library recombinant phagemid Av1 were modified with 84 DNA segments respectively having nucleic acid sequences of SEQ ID NOs: 128-211 to produce a VH library (i.e., VH2, VH3, VH4, VH5, VH6, VH7, VH8, VH9, VH11, VH12, VH13, VH14, VH15, VH16, or VH17 library). The VL and VH libraries were then respectively selected with protein L and protein A; and the phagemid DNA extracted from the scFv variant(s) that exhibited binding affinity to either protein L or protein A was used as a template to respectively amplify the nucleic acid sequences of VL and VH. Those amplified nucleic acid sequences were then inserted into the phagemid vector pCANTAB5E, which was used to transform E. coli ER2738 strain so as to amplify the phage expressing the scFv. The obtained phage-displayed scFv library was named antibody library GH2, GH3, GH4, GH5, GH6, GH7, GH8, GH9, GH11, GH12, GH13, GH14, GH15, GH16, or GH17.

The above data indicated that the present libraries (i.e., GH2, GH3, GH4, GH5, GH6, GH7, GH8, GH9, GH11, GH12, GH13, GH14, GH15, GH16, and GH17) comprised a plurality of phage-displayed scFv having the following characteristics: (1) a specific CS combination, in which each of the CDR-H1, CDR-L2 and CDR-L3 had a type 1 CS, and each of the CDR-H2 and CDR-L1 had a type 2 CS; (2) a specific distribution of aromatic residues that are similar with those of a natural antibody; and a specific nucleic acid sequence in each CDR, in which the CDR-L1 is encoded by a sequence comprising any of SEQ ID NOs: 2-10, CDR-L2 is encoded by a sequence comprising any of SEQ ID NOs: 11-14, CDR-L3 is encoded by a sequence comprising any of SEQ ID NOs: 15-22, CDR-H1 is encoded by a sequence comprising any of SEQ ID NOs: 23-26, CDR-H2 is encoded by a sequence comprising any of SEQ ID NOs: 27-28, and CDR-H3 is encoded by a sequence comprising any of SEQ ID NOs: 29-106.

2.2 Verification of Antibody Libraries GH2-GH9 and GH11-GH17

The antibody libraries GH2-GH9 and GH11-GH17 established in Example 2.1 was verified by the following assays:

(1) competition assay, which was used to determine the epitope of an antigen; (2) $EC_{50}$ and BIAcore assay, methods to evaluate the antigen-antibody binding affinity; and (3) epitope mapping, which was used to analyze the epitope(s) on the antigen molecule recognized by the antibody.

90 anti-HER2/ECD scFv were randomly selected from the GH2 library (designated as S90 antibodies), in which 3 paratopes were dominantly expressed: paratope M32-M62, paratope M63-M64, and paratope M41-M61 (data not shown). The binding affinities of the antibodies S316 and 6 mouse antibodies (i.e., M32, M41, M61, M62, M63, and M64; all of which were directly selected from immunized mice and possessed different gene segments) to the peptide HER2/ECD were evaluated by the competition assay, in which four commercial antibodies (i.e., A21, Fab37, pertuzumab, and trastuzumab), previously known as HER2-specific antibodies, served as control. In the structure data, it is known that the peptide HER2/ECD could be divided into 4 domains (i.e., domain I, II, III, and IV), in which the epitopes recognized by A21, Fab37, pertuzumab and trastuzumab were respectively located in domains I, III, II, and IV; while the epitopes recognized by paratopes M32-M62, M63-M64, and M41-M61 were respectively located in domains I, III, and IV (data not shown). As to the competition result, a portion of paratope M32-M62 was overlapped with the paratope of A21; the paratope M63-M64 was overlapped with the paratope of Fab37; and the paratope M41-M61 was not overlapped with any paratope of the previously known antibodies (data not shown). The epitope mapping results indicated that the epitope E1 recognized by the paratope M32-M62 was near to, but not overlapped with, the epitope recognized by A21; and the epitope E3 recognized by paratope M41-M61 was on a surface patch distal from the epitope recognized by trastuzumab.

Thus, these data suggested that the GH2 library comprised diverse scFv capable of recognizing different epitopes of an antigen (i.e., peptide HER2/ECD); and the epitopes recognized by GH2 library might be different from those recognized by the previously known antibodies.

Example 3 Production of Recombinant Antibody from Antibody Libraries GH2-GH9 and GH11-GH17

3.1 Production and Characterization of Recombinant Antibody Produced from Antibody Library GH2

To generate a recombinant antibody exhibiting the binding affinity to a specific antigen HER2, the scFv variants bound to peptide HER2/ECD were selected in 2 to 3 selection/amplification cycles from the antibody library GH2. The selected scFv variants were then expressed as their correspondingly soluble forms (i.e., soluble scFv) and screened by the same peptide HER2/ECD. To generate the recombinant antibody as an immunoglobulin form, the HER2/ECD-binding scFv was converted into an IgG antibody in accordance with the steps described in Materials and Methods. The recombinant antibody was then evaluated by ELISA and BIAcore to respectively determine the $EC_{50}$ and antigen-binding affinity to peptide HER2/ECD.

29 scFv (i.e., GH2-3, GH2-7, GH2-8, GH2-13, GH2-14, GH2-16, GH2-18, GH2-21, GH2-23, GH2-36, GH2-40, GH2-42, GH2-54, GH2-59, GH2-60, GH2-61, GH2-65, GH2-66, GH2-72, GH2-75, GH2-78, GH2-81, GH2-87, GH2-91, GH2-95, GH2-96, GH2-98, GH2-102, and GH2-104) randomly selected from S90 antibodies of Example 2.2 were expressed in IgG format, and hereinafter designated as S29 IgG. 6 antibodies (i.e., M32, M41, M61, M62, M63, and M64) and one commercial antibody trastuzumab, served as the control antibodies. As the data presented in Table 2, the lower limit of $EC_{50}$ of the S29 IgG was comparable with that of the affinity-matured antibodies (i.e., M32, M41, M61, M62, M63, M64, and trastuzumab). It is worth noting that 12 of the S29 IgG had $EC_{50}$ lower than that of trastuzumab. As to the binding affinity, the data analyzed from BIAcore measurements indicated that the lower limit of the $K_D$ of the S29 IgG approached $10^{-11}$ M, similar to that of the affinity-matured antibodies (i.e., M32, M41, M61, M62, M63, M64, and trastuzumab).

TABLE 2

Characterizations of S29 IgG, 6 mouse affinity-matured antibodies, one humanized antibody, and one commercial antibody

| SEQ ID NO | Antibody | Epitope | Yield (mg/L) | $EC_{50}$ (ng/mL) | BIAcore assay $k_{on}$ ($M^{-1}S^{-1}$) | $k_{off}$ ($S^{-1}$) | $K_D(M)$ |
|---|---|---|---|---|---|---|---|
| 241 | GH2-3 | M63-M64 | 8.0 | 7.0 | $2.425 \times 10^5$ | $5.024 \times 10^{-4}$ | $2.071 \times 10^{-9}$ |
| 244 | GH2-7 | M32-M62 | 11.0 | 3.3 | $6.179 \times 10^6$ | $6.082 \times 10^{-2}$ | $9.842 \times 10^{-9}$ |
| 245 | GH2-8 | M32-M62 | 9.3 | 5.1 | $5.988 \times 10^5$ | $1.551 \times 10^{-4}$ | $2.590 \times 10^{-10}$ |
| 249 | GH2-13 | M32-M62 | 7.7 | 3.0 | $3.103 \times 10^6$ | $8.179 \times 10^{-3}$ | $2.636 \times 10^{-9}$ |
| 250 | GH2-14 | M32-M62 | 41.1 | 9.2 | $3.365 \times 10^5$ | $5.735 \times 10^{-3}$ | $1.704 \times 10^{-8}$ |
| 251 | GH2-16 | Ungroup | 18.8 | 4.2 | $8.571 \times 10^4$ | $1.025 \times 10^{-4}$ | $1.196 \times 10^{-9}$ |
| 253 | GH2-18 | Ungroup | 13.8 | 3.3 | $1.563 \times 10^5$ | $1.086 \times 10^{-5}$ | $6.948 \times 10^{-11}$ |
| 256 | GH2-21 | M41-M61 | 15.8 | 4.1 | $4.435 \times 10^5$ | $6.228 \times 10^{-4}$ | $1.404 \times 10^{-9}$ |
| 257 | GH2-23 | M41-M61 | 11.0 | 4.5 | $2.174 \times 10^5$ | $1.797 \times 10^{-4}$ | $8.266 \times 10^{-10}$ |
| 268 | GH2-36 | M32-M62 | 10.1 | 3.9 | $8.681 \times 10^8$ | 7.7 | $8.852 \times 10^{-9}$ |
| 272 | GH2-40 | M32-M62 | 8.7 | 4.0 | $7.118 \times 10^4$ | $2.165 \times 10^{-4}$ | $3.042 \times 10^{-9}$ |
| 274 | GH2-42 | M32-M62 | 19.3 | 2.7 | $1.393 \times 10^6$ | $2.354 \times 10^{-4}$ | $1.690 \times 10^{-10}$ |
| 284 | GH2-54 | M32-M62 | 27.0 | 8.0 | $3.387 \times 10^5$ | $1.282 \times 10^{-2}$ | $3.785 \times 10^{-8}$ |
| 288 | GH2-59 | M32-M62 | 5.8 | 31.2 | $4.778 \times 10^4$ | $2.877 \times 10^{-4}$ | $6.022 \times 10^{-9}$ |
| 289 | GH2-60 | M32-M62 | 15.8 | 3.4 | $3.636 \times 10^6$ | $5.557 \times 10^{-3}$ | $1.529 \times 10^{-9}$ |
| 290 | GH2-61 | M32-M62 | 10.0 | 3.5 | $3.866 \times 10^5$ | $1.044 \times 10^{-4}$ | $2.700 \times 10^{-10}$ |
| 294 | GH2-65 | M32-M62 | 6.8 | 7.6 | $3.497 \times 10^5$ | $1.110 \times 10^{-2}$ | $3.175 \times 10^{-8}$ |
| 295 | GH2-66 | M32-M62 | 12.3 | 7.9 | $6.026 \times 10^6$ | $3.284 \times 10^{-1}$ | $5.453 \times 10^{-8}$ |
| 299 | GH2-72 | M32-M62 | 12.6 | 13.7 | $9.152 \times 10^8$ | 10.89 | $1.189 \times 10^{-8}$ |
| 301 | GH2-75 | M32-M62 | 18.3 | 2.2 | $8.399 \times 10^5$ | $1.486 \times 10^{-4}$ | $1.769 \times 10^{-10}$ |
| 304 | GH2-78 | M32-M62 | 12.1 | 24.4 | $3.302 \times 10^4$ | $1.632 \times 10^{-3}$ | $4.942 \times 10^{-8}$ |
| 307 | GH2-81 | M32-M62 | 28.1 | 5.0 | $9.750 \times 10^5$ | $1.309 \times 10^{-2}$ | $1.343 \times 10^{-8}$ |
| 312 | GH2-87 | M63-M64 | 40.2 | 14.7 | $3.948 \times 10^5$ | $5.248 \times 10^{-3}$ | $1.329 \times 10^{-8}$ |

TABLE 2-continued

Characterizations of S29 IgG, 6 mouse affinity-matured antibodies, one humanized antibody, and one commercial antibody

| SEQ ID NO | Antibody | Epitope | Yield (mg/L) | EC$_{50}$ (ng/mL) | BIAcore assay $k_{on}$ (M$^{-1}$S$^{-1}$) | $k_{off}$ (S$^{-1}$) | $K_D$(M) |
|---|---|---|---|---|---|---|---|
| 315 | GH2-91 | M32-M62 | 14.2 | 4.2 | $2.747 \times 10^6$ | $6.790 \times 10^{-3}$ | $2.472 \times 10^{-9}$ |
| 319 | GH2-95 | M32-M62 | 29.8 | 3.2 | $5.466 \times 10^4$ | $2.441 \times 10^{-4}$ | $4.466 \times 10^{-9}$ |
| 320 | GH2-96 | M32-M62 | 20.1 | 3.4 | $2.537 \times 10^5$ | $1.375 \times 10^{-3}$ | $5.422 \times 10^{-9}$ |
| 322 | GH2-98 | M32-M62 | 29.7 | 82.3 | $2.536 \times 10^5$ | $2.243 \times 10^{-4}$ | $8.847 \times 10^{-8}$ |
| 325 | GH2-102 | M32-M62 | 8.1 | 23.1 | $1.371 \times 10^6$ | $3.902 \times 10^{-3}$ | $2.845 \times 10^{-8}$ |
| 327 | GH2-104 | M32-M62 | 41.7 | 2.8 | $8.515 \times 10^5$ | $8.841 \times 10^{-4}$ | $1.035 \times 10^{-9}$ |
| 233 | M32 | M32-M62 | 6.8 | 3.1 | $2.941 \times 10^5$ | $7.147 \times 10^{-5}$ | $2.430 \times 10^{-10}$ |
| 331 | M41 | M41-M61 | 13.8 | 3.4 | $6.708 \times 10^5$ | $3.481 \times 10^{-5}$ | $5.189 \times 10^{-11}$ |
| 332 | M61 | M41-M61 | 21.3 | 3.5 | $4.060 \times 10^6$ | $2.401 \times 10^{-3}$ | $5.912 \times 10^{-10}$ |
| 237 | M62 | M32-M62 | 5.4 | 2.0 | $7.883 \times 10^5$ | $1.799 \times 10^{-5}$ | $2.282 \times 10^{-11}$ |
| 333 | M63 | M63-M64 | 10.2 | 2.4 | $6.155 \times 10^5$ | $7.339 \times 10^{-5}$ | $1.192 \times 10^{-11}$ |
| 334 | M64 | M63-M64 | 12.8 | 3.1 | $1.735 \times 10^6$ | $3.374 \times 10^{-4}$ | $1.945 \times 10^{-10}$ |
| 235 | H32 | M32-M62 | 17.6 | 3.2 | $1.592 \times 10^5$ | $3.850 \times 10^{-5}$ | $2.418 \times 10^{-10}$ |
| | Trastuzumab | Ungroup | — | 4.5 | $2.543 \times 10^6$ | $2.157 \times 10^{-5}$ | $8.482 \times 10^{-12}$ |

Further, the CDR sequences of S29 IgG, 6 mouse affinity-matured antibodies, one humanized antibody, and one commercial antibody were analyzed and referenced as SEQ ID NOs: 233, 235, 237, or 241-334, in which the antibody M32 was encoded by a nucleic acid sequence of SEQ ID NO: 232; the antibody M62 was encoded by a nucleic acid sequence of SEQ ID NO: 236; and the antibody H32, a humanized antibody with the CDR sequence of antibody, was encoded by a nucleic acid sequence of SEQ ID NO: 234.

In addition to the peptide HER2/ECD, the GH2 library could also be used to generate recombinant antibodies with binding affinity to other antigens. With the similar production procedure described in the first paragraph of Example 3.1, the GH2 library was applied to produce antibodies against 22 different protein antigens, in which 20 out of the 22 proteins could be recognized by the GH2-produced antibodies (Table 3).

TABLE 3

Binding specificity of GH2 library to specified protein antigen

| Antigens | Analyzed clones[a] | Unique clones[b] |
|---|---|---|
| Maltose-binding protein | 274/638 | 23/78 |
| Bovine serum albumin | 427/630 | 54/116 |
| Human serum albumin | 51/72 | 2/8 |
| Lysozyme | 143/525 | 16/46 |
| RNase A | 0/424 | 0 |
| Interleukin-1 beta | 2/288 | 1/2 |
| Human DNase I | 0/412 | 0 |
| Hemagglutinin of A/California/7/2009(H1N1) | 1342/2893 | 187/691 |
| Hemagglutinin of A/Brisbane/10/2007(H3N2) | 239/360 | 57/152 |
| Hemagglutinin of A/Wisconsin/67/2005(H3N2) | 35/133 | 14/30 |
| Hemagglutinin of A/Vietnam/1194/2004(H5N1) | 30/42 | 9/14 |
| Nucleoprotein of A/Taiwan/1/72(H3N2) | 365/480 | 64/89 |
| Nucleoprotein of A/WSN/33(H1N1) | 273/479 | 39/61 |
| Vascular endothelial growth factor | 414/1088 | 32/114 |
| Epidermal growth factor receptor 1/ECD | 85/96 | 11/72 |
| Epidermal growth factor receptor 2/ECD | 363/719 | 103/363 |
| Epidermal growth factor receptor 3/ECD | 70/96 | 24/70 |
| Programmed death-ligand 1/ECD | 56/96 | 8/32 |
| Sialic acid binding Ig-like lectin 3/ECD | 9/16 | 3/9 |
| Glucagon receptor/ECD | 522/860 | 153/378 |

TABLE 3-continued

Binding specificity of GH2 library to specified protein antigen

| Antigens | Analyzed clones[a] | Unique clones[b] |
|---|---|---|
| Rituximab | 39/72 | 23/37 |
| Immunoglobulin G/Fragment crystallizable region (Fc region) | 25/48 | 14/25 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

In conclusion, the data indicated that the GH2 library can be used to produce different recombinant antibodies with high binding-affinity (about $10^{-7}$ to $10^{-11}$ M) to different antigens, and the antigen-binding affinities of those recombinant antibodies were comparable to those of affinity-matured or commercial antibodies.

3.2 Characterization of Recombinant Antibodies Produced from Antibody Libraries GH3-GH9 and GH11-GH17

The recombinant antibodies produced from antibody libraries GH3-GH9 and GH11-GH17 were examined in this example.

Tables 4-17 depicted the binding specificity of the recombinant antibodies respectively from the libraries GH3-GH9 and GH11-GH17 to specified protein antigens.

TABLE 4

Binding specificity of GH3 library to specified protein antigen

| Antigens | Analyzed clones[a] | Unique clones[b] |
|---|---|---|
| Interleukin-1 beta | 14/208 | 4/19 |
| Human DNase I | 6/178 | 5/6 |
| Hemagglutinin of A/California/7/2009(H1N1) | 92/193 | 11/26 |
| Epidermal growth factor receptor 2/ECD[c] | 105/161 | 15/25 |
| Sialic acid binding Ig-like lectin 3/ECD | 7/16 | 3/7 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 5

Binding specificity of GH4 library to specified protein antigen

| Antigens | Analyzed clones[a] | Unique clones[b] |
|---|---|---|
| Interleukin-1 beta | 113/192 | 6/49 |
| Human DNase I | 14/222 | 2/7 |
| Hemagglutinin of A/California/7/2009(H1N1) | 212/352 | 35/82 |
| Epidermal growth factor receptor 2/ECD[c] | 178/224 | 37/92 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 6

Binding specificity of GH5 library to specified protein antigen

| Antigens | Analyzed clones[a] | Unique clones[b] |
|---|---|---|
| Hemagglutinin of A/California/7/2009(H1N1) | 165/288 | 28/98 |
| Epidermal growth factor receptor 1/ECD[c] | 47/96 | 2/24 |
| Epidermal growth factor receptor 2/ECD | 123/144 | 5/60 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 7

Binding specificity of GH6 library to specified protein antigen

| Antigens | Analyzed clones[a] | Unique clones[b] |
|---|---|---|
| Hemagglutinin of A/California/7/2009(H1N1) | 80/176 | 14/36 |
| Epidermal growth factor receptor 2/ECD[c] | 76/122 | 5/18 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 8

Binding specificity of GH7 library to specified protein antigen

| Antigens | Analyzed clones[a] | Unique clones[b] |
|---|---|---|
| Hemagglutinin of A/California/7/2009(H1N1) | 44/128 | 9/22 |
| Epidermal growth factor receptor 2/ECD[c] | 6/32 | 3/6 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 9

Binding specificity of GH8 library to specified protein antigen

| Antigens | Analyzed clones[a] | Unique clones[b] |
|---|---|---|
| Human DNase I | 11/123 | 1/5 |
| Hemagglutinin of A/California/7/2009(H1N1) | 116/363 | 11/30 |
| Epidermal growth factor receptor 2/ECD[c] | 25/48 | 2/6 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 10

Binding specificity of GH9 library to specified protein antigen

| Antigens | Analyzed clones[a] | Unique clones[b] |
|---|---|---|
| Hemagglutinin of A/California/7/2009(H1N1) | 74/128 | 5/22 |
| Epidermal growth factor receptor 2/ECD[c] | 6/32 | 2/3 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 11

Binding specificity of GH11 library to specified protein antigen

| Antigens | Analyzed clones[a] | Unique clones[b] |
|---|---|---|
| Hemagglutinin of A/Brisbane/59/2007(H1N1) | 85/192 | 7/16 |
| Hemagglutinin of A/California/7/2009(H1N1) | 205/288 | 14/40 |
| Hemagglutinin of A/Wisconsin/67/2005(H3N2) | 168/192 | 2/24 |
| Nucleoprotein of A/Taiwan/1/72(H3N2) | 165/192 | 30/32 |
| Nucleoprotein of A/WSN/33(H1N1) | 172/192 | 24/32 |
| Epidermal growth factor receptor 1/ECD[c] | 44/96 | 5/8 |
| Epidermal growth factor receptor 2/ECD | 76/96 | 9/16 |
| Programmed death-ligand 1/ECD | 89/96 | 4/8 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 12

Binding specificity of GH12 library to specified protein antigen

| Antigens | Analyzed clones[a] | Unique clones[b] |
|---|---|---|
| Hemagglutinin of A/Brisbane/59/2007(H1N1) | 25/96 | 5/8 |
| Hemagglutinin of A/California/7/2009(H1N1) | 172/192 | 11/32 |
| Hemagglutinin of A/Wisconsin/67/2005(H3N2) | 60/96 | 4/8 |
| Nucleoprotein of A/Taiwan/1/72(H3N2) | 85/144 | 36/47 |
| Nucleoprotein of A/WSN/33(H1N1) | 92/144 | 40/51 |
| Epidermal growth factor receptor 1/ECD[c] | 55/96 | 8/16 |
| Epidermal growth factor receptor 2/ECD | 52/96 | 18/25 |
| Epidermal growth factor receptor 3/ECD | 68/96 | 21/29 |
| Programmed death-ligand 1/ECD | 38/96 | 1/8 |
| Sialic acid binding Ig-like lectin 3/ECD | 3/16 | 3/3 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 13

Binding specificity of GH13 library to specified protein antigen

| Antigens | Analyzed clones[a] | Unique clones[b] |
|---|---|---|
| Hemagglutinin of A/Brisbane/59/2007(H1N1) | 79/96 | 10/16 |
| Hemagglutinin of A/California/7/2009(H1N1) | 143/193 | 7/24 |
| Hemagglutinin of A/Wisconsin/67/2005(H3N2) | 57/96 | 8/13 |
| Nucleoprotein of A/Taiwan/1/72(H3N2) | 99/144 | 39/51 |
| Nucleoprotein of A/WSN/33(H1N1) | 103/192 | 37/41 |
| Epidermal growth factor receptor 1/ECD[c] | 39/144 | 8/12 |
| Epidermal growth factor receptor 2/ECD | 82/96 | 15/22 |
| Epidermal growth factor receptor 3/ECD | 39/96 | 19/23 |
| Programmed death-ligand 1/ECD | 73/96 | 5/14 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 14

Binding specificity of GH14 library to specified protein antigen

| Antigens | Analyzed clones[a] | Unique clones[b] |
|---|---|---|
| Hemagglutinin of A/Brisbane/59/2007(H1N1) | 67/192 | 17/22 |
| Hemagglutinin of A/California/7/2009(H1N1) | 159/192 | 12/20 |
| Hemagglutinin of A/Wisconsin/67/2005(H3N2) | 99/192 | 12/18 |
| Nucleoprotein of A/Taiwan/1/72(H3N2) | 63/192 | 14/35 |
| Nucleoprotein of A/WSN/33(H1N1) | 84/192 | 14/28 |
| Epidermal growth factor receptor 1/ECD[c] | 26/96 | 2/6 |
| Epidermal growth factor receptor 2/ECD | 33/192 | 8/19 |
| Epidermal growth factor receptor 3/ECD | 118/192 | 36/41 |
| Programmed death-ligand 1/ECD | 24/96 | 2/8 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 15

Binding specificity of GH15 library to specified protein antigen

| Antigens | Analyzed clones[a] | Unique clones[b] |
|---|---|---|
| Hemagglutinin of A/California/7/2009(H1N1) | 83/240 | 17/24 |
| Nucleoprotein of A/Taiwan/1/72(H3N2) | 90/96 | 1/16 |

[a]The ratio indicates the positive clones over the total analyzed single colonies for the corresponding antigen.
[b]The ratio indicates the sequence-wise unique clones over the total sequenced positive clones.

TABLE 16

Binding specificity of GH16 library to specified protein antigen

| Antigens | Analyzed clones[a] | Unique clones[b] |
|---|---|---|
| Hemagglutinin of A/California/7/2009(H1N1) | 10/99 | 5/10 |
| Nucleoprotein of A/Taiwan/1/72(H3N2) | 3/48 | 3/3 |
| Nucleoprotein of A/WSN/33(H1N1) | 1/48 | 1/1 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

TABLE 17

Binding specificity of GH17 library to specified protein antigen

| Antigens | Analyzed clones[a] | Unique clones[b] |
|---|---|---|
| Hemagglutinin of A/California/7/2009(H1N1) | 31/96 | 5/16 |
| Hemagglutinin of A/Wisconsin/67/2005(H3N2) | 12/48 | 3/10 |
| Nucleoprotein of A/Taiwan/1/72(H3N2) | 57/96 | 2/24 |
| Nucleoprotein of A/WSN/33(H1N1) | 81/96 | 1/8 |
| Epidermal growth factor receptor 3/ECD[c] | 77/96 | 2/6 |

[a]The ratio indicates the positive clones over the total analyzed single colonies for the corresponding antigen.
[b]The ratio indicates the sequence-wise unique clones over the total sequenced positive clones.
[c]ECD, the receptor's extracellular domain.

These data indicated that the recombinant antibodies respectively produced from GH3-GH9 and GH11-GH17 exhibited binding specificity to different protein antigens, including protein antigen selected from the group consisting of IL-1β, HA, NP, EGFR1, EGFR 2, EGFR3, human DNase I, PD-L1, and SIGLEC 3.

3.3 Verification of the Biological Function of Recombinant Antibodies

Figure 2:
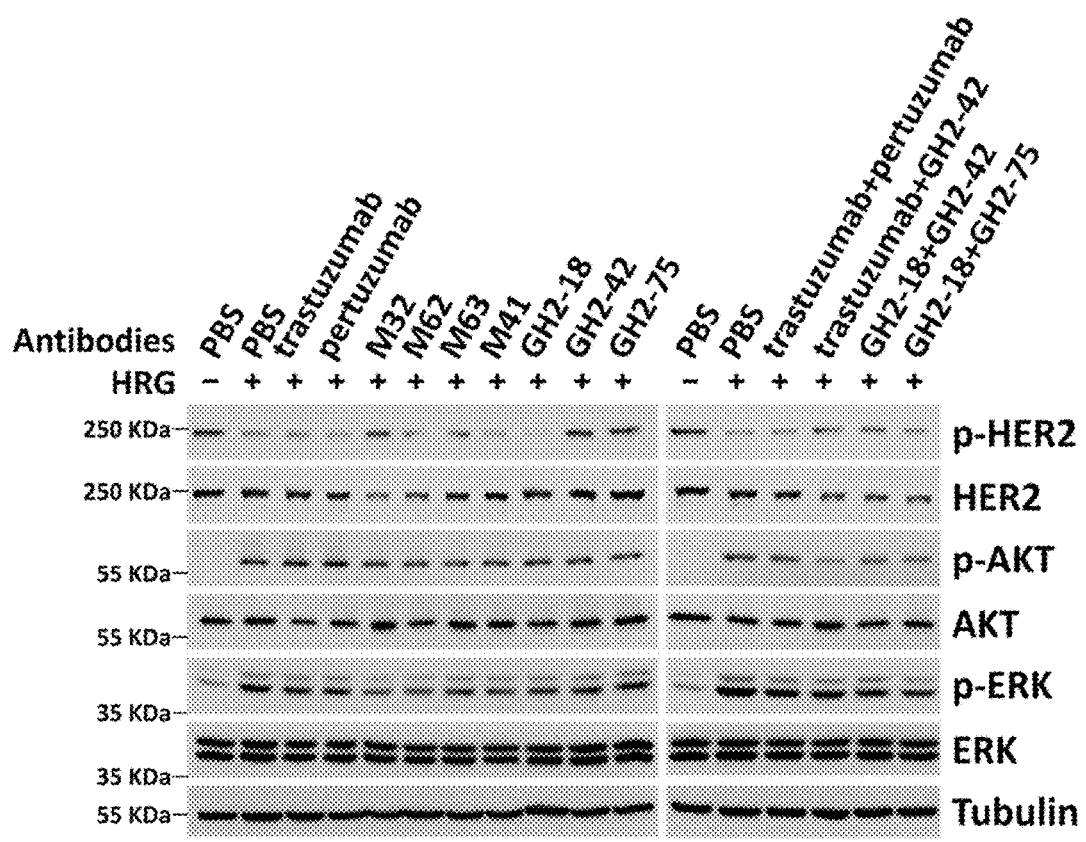
FIG. 2 are photographs of western blot that depict the protein expressions of SKBR3 cells, which were respectively treated with specified antibodies; and the proteins were respectively detected by anti-phosphorylated HER2 (p-HER2), anti-HER2, anti-phosphorylated AKT (p-AKT), anti-AKT, anti-phosphorylated ERK (p-ERK), anti-ERK, and anti-tubulin antibodies according to example 3 of the present disclosure.

The 6 antibodies directly selected from the HER2/ECD immunized mice (i.e., M32, M41, M61, M62, M63, and M64) and the recombinant antibodies produced by GH2 library were respectively evaluated by the functional assay. Compared with trastuzumab and pertuzumab, the antibody M32 bound to a novel epitope on domain I of HER2/ECD (data not shown), and caused the internalization of HER2 followed by the depletion of the receptor on HER2-overexpressed cell SKBR3 surface (FIGS. 1A and 2). The antibody M62 shared the similar epitope with M32 (data not shown), and possessed the similar effect as M32 on cell surface HER2 depletion (FIGS. 1A and 2). Antibodies M63 and M41 respectively bound to the epitopes on domain III and domain IV of HER2, and both them did not cause HER2 depletion (data not shown).

Figure 1B:
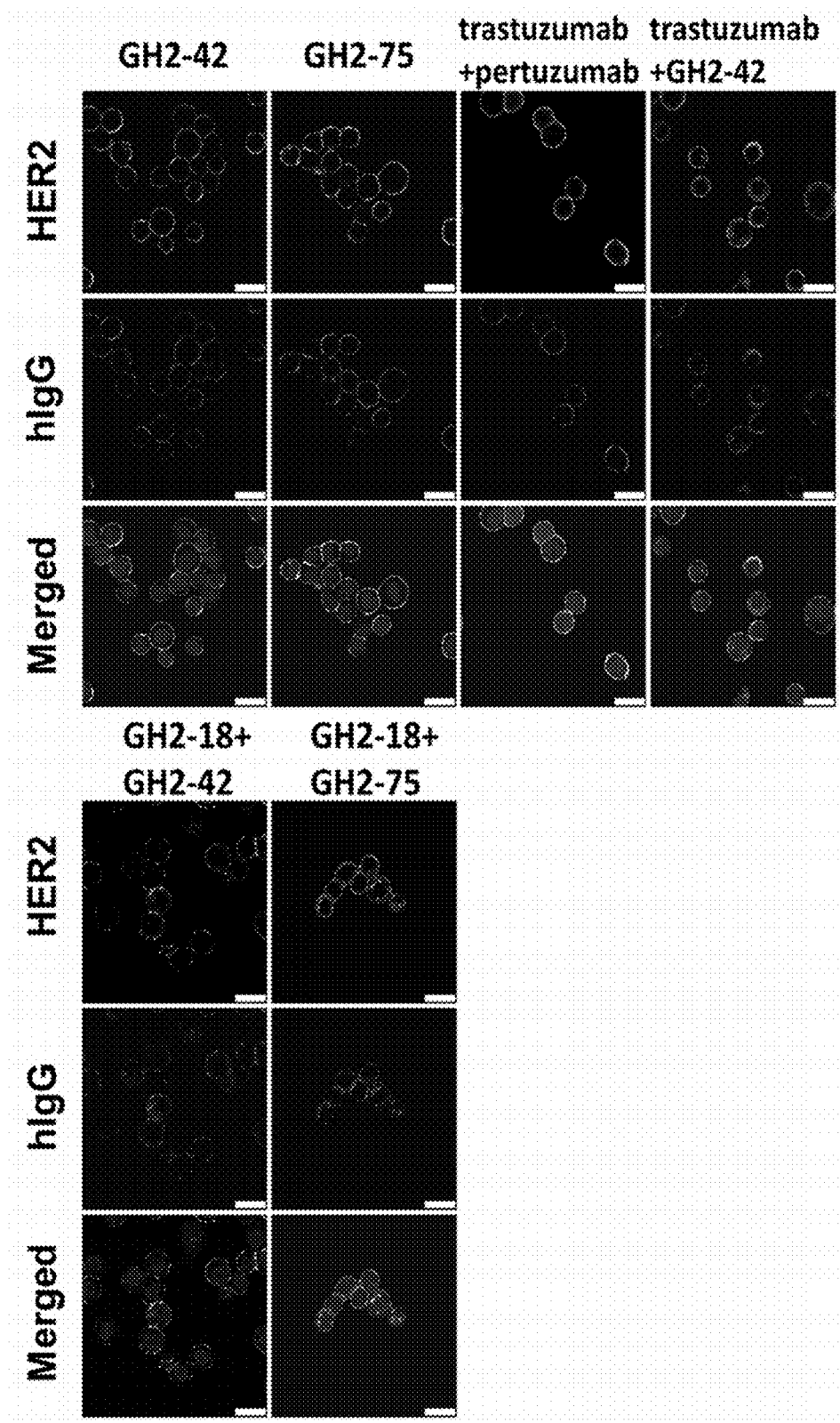
FIG. 1B are photographs of immunofluorescent staining that depict the SKBR3 cells respectively treated with specified antibodies according to example 3 of the present disclosure; the scale bar represents 25 μm.

As to the recombinant antibodies, although recombinant antibodies GH2-42 and GH2-75 recognized the similar epitope and exhibited the similar binding affinity (about $\sim 10^{-10}$ M, Table 2) with M32, they did not cause HER2 depletion as M32 did (FIGS. 1B and 2). Combining GH2-42 with trastuzumab or GH2-18, a recombinant antibody shared the similar paratope with trastuzumab, resulted in HER2 depletion. Besides, combination of GH2-75 with GH2-18 also caused HER2 internalization (FIGS. 1B and 2). The data implied that the simultaneously binding of domains I and IV of HER2/ECD by antibodies would cause the HER2 depletion, whereas the simultaneously binding of domains II and IV of HER2 did not possess the depletion effect.

For the receptor HER2 participated in various signal transduction pathway, the next issue to be addressed was whether the binding of HER2 by different antibodies of the present disclosure would affect the down-stream gene expression or activation. As the western blot data indicated in FIG. 2, the binding of different antibodies to different epitopes on HER2 inhibited both AKT and ERK activation to various extents.

These results indicated that the diversity of recombinant antibodies produced by the present GH2 library can be applied to recognize different epitopes of an antigen, and accordingly, exert various biological functions.

3.4 Binding and Neutralization Characteristics of the Recombinant Antibody Produced from GH2-GH9 and GH11-GH17 Libraries 125 unique scFvs were obtained from three runs of panning against A/California/2009 H1N1 HA according to recombinant HA binding result by ELISA assay. These scFvs were analyzed for native HA protein binding by FACS and H1N1 CA/09 pseudovirus neutralization. In this example, F10 scFv, a well known antibody with strong neutralization for H1N1 influenza virus, was used as positive control; S40 served as another positive control; and AV1 served as the negative control.

Figure 3A:
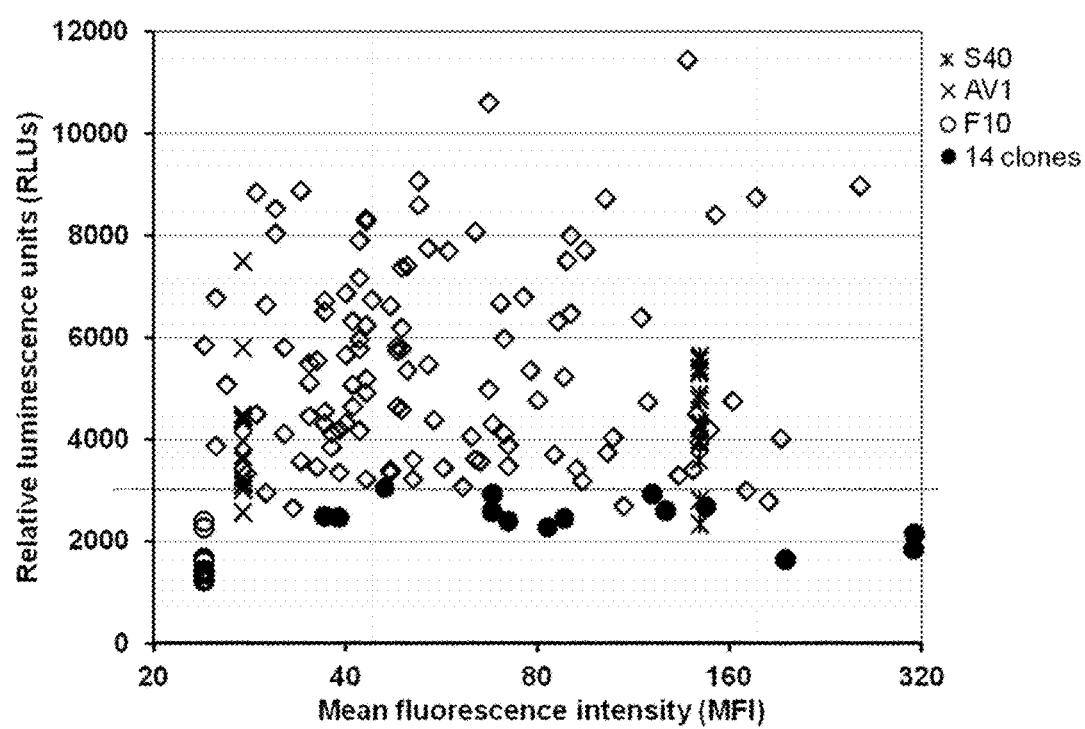
FIG. 3A is a data depicting the correlation of H1N1 neutralization ability and native HA binding affinity of the recombinant antibody produced by the present phage-displayed scFv libraries according to example 3 of the present disclosure.

14 scFvs were selected, in which each of the 14 scFvs may have better neutralization ability than F10 scFv, and range from 1500 RLUs-3000 RLUs (FIG. 3A). When the native protein binding and neutralization result were correlated, 12 of 14 scFvs can bind native protein with high affinity. It is possible that the other two scFv with poor binding ability result from low amount of secreted scFv in culture medium.

Figure 3B:
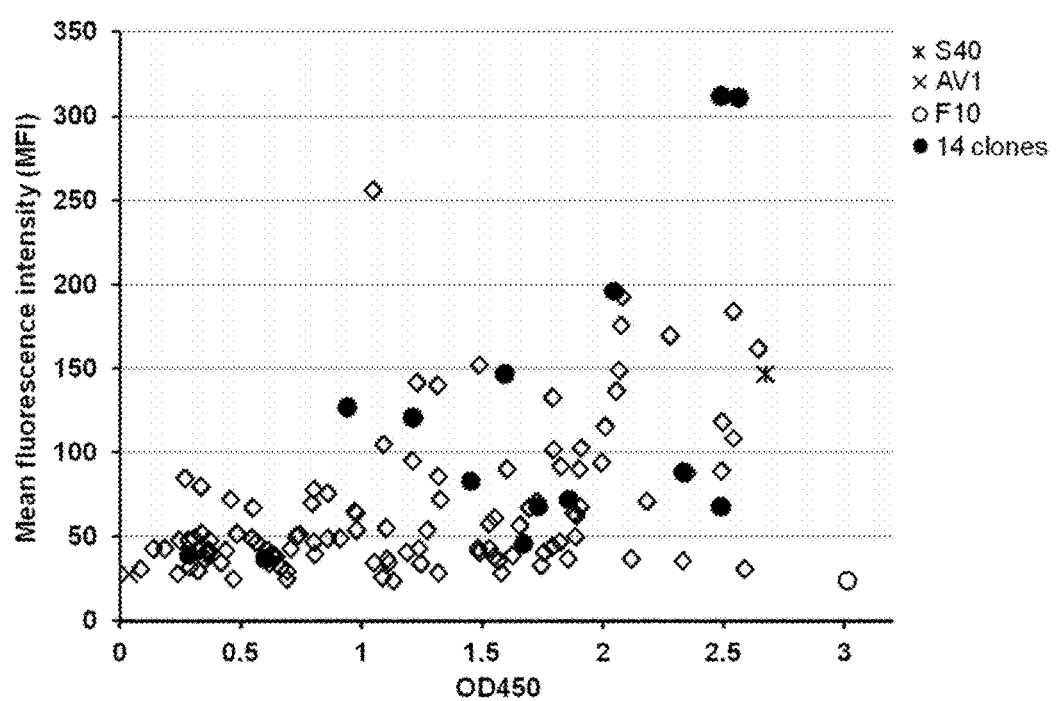
FIG. 3B is a data depicting the correlation of native HA binding affinity and the recombinant HA binding affinity of the recombinant antibody produced by the present phage-displayed scFv libraries according to example 3 of the present disclosure.

The binding affinities of the 14 scFvs to the native HA and the recombinant HA were evaluated by FACS analysis and ELISA assay, respectively. As depicted in FIG. 3B, half of the ELISA positive scFvs can't bind native HA proteins. It is interesting that the 14 scFvs showed positive correlation between ELISA and FACS analysis. This may reflect different amount and affinity of scFvs in culture medium.

In conclusion, the present disclosure provides a phage-displayed scFv library (i.e., GH2 library) that comprised a plurality of phage-displayed scFvs characterized with a specific CS combination, a specific distribution of aromatic residues in each CDR, and a specific sequence in each CDR. The present GH2 library could be used to efficiently produce a plurality of recombinant antibodies exhibiting highly binding affinity to a specific antigen. Those produced recombinant antibodies are diverse in their CDRs and accordingly, capable of binding to different epitopes on the specific antigen so as to exert various biological functions. The present disclosure thus provides a potential means to generate different antigen-specific antibodies promptly in accordance with the need in experimental researches and/or clinical applications.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A recombinant antibody prepared from a phage-displayed single-chain variable fragment (scFv) library comprising a plurality of phage-displayed scFvs, wherein each of the plurality of phage-displayed scFvs comprises a first heavy chain complementarity determining region (CDR-H1), a second heavy chain CDR (CDR-H2), a third heavy chain CDR (CDR-H3), a first light chain CDR (CDR-L1), a second light chain CDR (CDR-L2), and a third light chain CDR (CDR-L3), wherein
   each of the CDR-H1, CDR-L2 and CDR-L3 has a type 1 canonical structure (CS), whereas each of the CDR-H2 and CDR-L1 has a type 2 CS;
   each of the CDR-H1, CDR-H2, CDR-H3, CDR-L1, CDR-L2, and CDR-L3 has a distribution of aromatic residues that is similar to the distribution of aromatic residues in the corresponding CDR-H1, CDR-H2, CDR-H3, CDR-L1, CDR-L2, and CDR-L3 of a natural antibody; and
   the CDR-L1 is encoded by a first coding sequence comprising the nucleic acid sequence of any of SEQ ID NOs: 2-10, the CDR-L2 is encoded by a second coding sequence comprising the nucleic acid sequence of any of SEQ ID NOs: 11-14, the CDR-L3 is encoded by a third coding sequence comprising the nucleic acid sequence of any of SEQ ID NOs: 15-22, the CDR-H1 is encoded by a fourth coding sequence comprising the nucleic acid sequence of any of SEQ ID NOs: 23-26, the CDR-H2 is encoded by a fifth coding sequence comprising the nucleic acid sequence of any of SEQ ID NOs: 27-28, and the CDR-H3 is encoded by a sixth coding sequence comprising the nucleic acid sequence of any of SEQ ID NOs: 29-106.

2. The recombinant antibody of claim 1, wherein the recombinant antibody comprises the amino acid sequence at least 90% identical to any of SEQ ID NOs: 241-330.

3. The recombinant antibody of claim 1, wherein the recombinant antibody comprises the amino acid sequence 100% identical to any of SEQ ID NOs: 241-330.

4. The recombinant antibody of claim 3, wherein the recombinant antibody comprises the amino acid sequence of SEQ ID NO: 241, 244, 245, 249, 250, 251, 253, 256, 257, 268, 272, 274, 284, 288, 289, 290, 294, 295, 299, 301, 304, 307, 312, 315, 319, 320, 322, 325 or 327.

5. The recombinant antibody of claim 4, wherein the recombinant antibody comprises the amino acid sequence of SEQ ID NO: 253.

6. The recombinant antibody of claim 4, wherein the recombinant antibody comprises the amino acid sequence of SEQ ID NO: 274.

7. The recombinant antibody of claim 4, wherein the recombinant antibody comprises the amino acid sequence of SEQ ID NO: 301.

8. A method of treating a HER2-related disease in a subject, comprising administering to the subject a therapeutically effective amount of the recombinant antibody of claim 1 so as to alleviate or ameliorate the symptom of the HER2-related disease.

9. The method of claim 8, wherein the recombinant antibody comprises the amino acid sequence at least 90% identical to any of SEQ ID NOs: 241-330.

10. The method of claim 9, wherein the recombinant antibody comprises the amino acid sequence 100% identical to any of SEQ ID NOs: 241-330.

11. The method of claim 10, wherein the recombinant antibody comprises the amino acid sequence of SEQ ID NO: 241, 244, 245, 249, 250, 251, 253, 256, 257, 268, 272, 274, 284, 288, 289, 290, 294, 295, 299, 301, 304, 307, 312, 315, 319, 320, 322, 325 or 327.

12. The method claim 11, wherein the recombinant antibody comprises the amino acid sequence of SEQ ID NO: 253.

13. The method claim 11, wherein the recombinant antibody comprises the amino acid sequence of SEQ ID NO: 274.

14. The method claim 11, wherein the recombinant antibody comprises the amino acid sequence of SEQ ID NO: 301.

15. The method of claim 8, wherein the HER2-related disease is a tumor.

16. The method of claim 8, wherein the subject is a human.

* * * * *

SEQUENCE LISTING

```
<160> NUMBER OF SEQ ID NOS: 340

<210> SEQ ID NO 1
<211> LENGTH: 798
<212> TYPE: DNA
<213> ORGANISM: Artificial Sequence
<220> FEATURE:
<223> OTHER INFORMATION: Synthetic

<400> SEQUENCE: 1
atggccgata ttcaaatgac ccagagcccg agcagcctga gcgcgagcgt gggagatcgc      60
gtgaccatta cctgccgtgc gagccaggat gttagcacgg cggtcgcatg gtatcagcag     120
aaaccaggca aagcgccgaa acttctgata tactctgcgt ccttcctgta tagcggcgtg     180
ccgtcgcgtt tttcgggcag tggcagcggc acggacttta ccctgacgat atcttcctta     240
caaccggagg attttgcgac ctactactgt caacagcatt ataccacacc gccgaccttc     300
ggtcaaggca ccaaagtgga aatcaaacgc ggaggggggag gtagcatcga gggccgtagc     360
ggaggtggcg ggagcgaagt gcagctggtg gaatcggag gcggtctggt gcaacctggc     420
ggcagccttc gtctgagctg tgcggcgagc gggttcacca ttagcgatta ctggattcat     480
tgggtgcgtc aagctcccgg caaggggctg gagtgggtcg cgggcattac gcccgctggc     540
ggttacacat attatgccga cagcgtgaaa ggtcgcttta cgattagtgc ggacaccagc     600
aaaaataccg cgtacctgca gatgaatagc ctgcgtgcg aagacacagc ggtgtattat     660
tgcgcgcgtt tcgtgttttt tctgccgtat gcgatggatt attgggggca gggcacccttt   720 gttaccgtga gctcggcgtc agcggccgca ggtgcgccgg tgccgtatcc ggatccgctg     780
gaaccgcgtg ccgcatag                                                  798

<210> SEQ ID NO 2
<211> LENGTH: 64
<212> TYPE: DNA
<213> ORGANISM: Artificial Sequence
<220> FEATURE:
<223> OTHER INFORMATION: Synthetic

<400> SEQUENCE: 2
gaccattacc tgccgtgcga gccaggatgt tthythythy gtcgcatggt atcagcagaa      60
acca                                                                  64

<210> SEQ ID NO 3
<211> LENGTH: 64
<212> TYPE: DNA
<213> ORGANISM: Artificial Sequence
<220> FEATURE:
```

<223> OTHER INFORMATION: Synthetic

<400> SEQUENCE: 3
gaccattacc tgccgtgcga gccaggatgt tthythykgg gtcgcatggt atcagcagaa    60
acca    64

<210> SEQ ID NO 4
<211> LENGTH: 64
<212> TYPE: DNA
<213> ORGANISM: Artificial Sequence
<220> FEATURE:
<223> OTHER INFORMATION: Synthetic

<400> SEQUENCE: 4
gaccattacc tgccgtgcga gccaggatgt tthykggkgg gtcgcatggt atcagcagaa    60
acca    64

<210> SEQ ID NO 5
<211> LENGTH: 64
<212> TYPE: DNA
<213> ORGANISM: Artificial Sequence
<220> FEATURE:
<223> OTHER INFORMATION: Synthetic

<400> SEQUENCE: 5
gaccattacc tgccgtgcga gccaggatgt tthykggthy gtcgcatggt atcagcagaa    60
acca    64

<210> SEQ ID NO 6
<211> LENGTH: 64
<212> TYPE: DNA
<213> ORGANISM: Artificial Sequence
<220> FEATURE:
<223> OTHER INFORMATION: Synthetic

<400> SEQUENCE: 6
gaccattacc tgccgtgcga gccaggatgt tkggthythy gtcgcatggt atcagcagaa    60
acca    64

<210> SEQ ID NO 7
<211> LENGTH: 64
<212> TYPE: DNA
<213> ORGANISM: Artificial Sequence
<220> FEATURE:
<223> OTHER INFORMATION: Synthetic

<400> SEQUENCE: 7
gaccattacc tgccgtgcga gccaggatgt tkggthykgg gtcgcatggt atcagcagaa    60
acca    64

<210> SEQ ID NO 8
<211> LENGTH: 64
<212> TYPE: DNA
<213> ORGANISM: Artificial Sequence
<220> FEATURE:
<223> OTHER INFORMATION: Synthetic

<400> SEQUENCE: 8
gaccattacc tgccgtgcga gccaggatgt tkggkggkgg gtcgcatggt atcagcagaa    60
acca    64

<210> SEQ ID NO 9
<211> LENGTH: 64
<212> TYPE: DNA
<213> ORGANISM: Artificial Sequence
<220> FEATURE:
<223> OTHER INFORMATION: Synthetic

<400> SEQUENCE: 9
gaccattacc tgccgtgcga gccaggatgt tkggkggthy gtcgcatggt atcagcagaa    60
acca    64

<210> SEQ ID NO 10
<211> LENGTH: 64
<212> TYPE: DNA
<213> ORGANISM: Artificial Sequence
<220> FEATURE:
<223> OTHER INFORMATION: Synthetic

<400> SEQUENCE: 10
gaccattacc tgccgtgcga gccaggatgt trryrryrry gtcgcatggt atcagcagaa    60
acca    64

<210> SEQ ID NO 11
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,33
<223> OTHER INFORMATION: /note="n is A, T, C, or G"

<400> SEQUENCE: 11
ggcaaagcgc cgaaacttct gatathythy ncnvsythyc tgtatagcgg cgtgccgtcg    60
cgttttcg    69

<210> SEQ ID NO 12
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,33
<223> OTHER INFORMATION: /note="n is A, T, C, or G"

<400> SEQUENCE: 12
ggcaaagcgc cgaaacttct gatathythy ncnvsykggc tgtatagcgg cgtgccgtcg    60
cgttttcg    69

<210> SEQ ID NO 13
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,33
<223> OTHER INFORMATION: /note="n is A, T, C, or G"

<400> SEQUENCE: 13
ggcaaagcgc cgaaacttct gatathykgg ncnvsykggc tgtatagcgg cgtgccgtcg    60

```
cgttttcg                                                              69

<210> SEQ ID NO 14
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31, 33
<223> OTHER INFORMATION: /note="n is A, T, C, or G"

<400> SEQUENCE: 14
ggcaaagcgc cgaaacttct gatathykgg ncnvsythyc tgtatagcgg cgtgccgtcg     60
cgttttcg                                                              69

<210> SEQ ID NO 15
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 43, 45
<223> OTHER INFORMATION: /note="n is A, T, C, or G"

<400> SEQUENCE: 15
gattttgcga cctactactg tcaacagthy thyrrythyc cgntnacctt cggtcaaggc     60
accaaagtgg                                                            70

<210> SEQ ID NO 16
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 43, 45
<223> OTHER INFORMATION: /note="n is A, T, C, or G"

<400> SEQUENCE: 16
gattttgcga cctactactg tcaacagthy thyrrykggc cgntnacctt cggtcaaggc     60
accaaagtgg                                                            70

<210> SEQ ID NO 17
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 43, 45
<223> OTHER INFORMATION: /note="n is A, T, C, or G"

<400> SEQUENCE: 17
gattttgcga cctactactg tcaacagthy kggrrykggc cgntnacctt cggtcaaggc     60
accaaagtgg                                                            70

<210> SEQ ID NO 18
<211> LENGTH: 70
<212> TYPE: DNA
<213> ORGANISM: Artificial Sequence
```

<220> FEATURE:
<223> OTHER INFORMATION: Synthetic
<220> FEATURE:
<221> NAME/KEY: variation
<222> LOCATION: 43,45
<223> OTHER INFORMATION: /note="n is A, T, C, or G"

<400> SEQUENCE: 18
gattttgcga cctactactg tcaacagthy kggrrythyc cgntnacctt cggtcaaggc    60
accaaagtgg                                                          70

<210> SEQ ID NO 19
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 43,45
<223> OTHER INFORMATION: /note="n is A, T, C, or G"

<400> SEQUENCE: 19
gattttgcga cctactactg tcaacagkgg thyrrythyc cgntnacctt cggtcaaggc    60
accaaagtgg                                                          70

<210> SEQ ID NO 20
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 43,45
<223> OTHER INFORMATION: /note="n is A, T, C, or G"

<400> SEQUENCE: 20
gattttgcga cctactactg tcaacagkgg thyrrykggc cgntnacctt cggtcaaggc    60
accaaagtgg                                                          70

<210> SEQ ID NO 21
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: V_region
<222> LOCATION: 43,45
<223> OTHER INFORMATION: /note="n is A, T, C, or G"

<400> SEQUENCE: 21
gattttgcga cctactactg tcaacagkgg kggrrykggc cgntnacctt cggtcaaggc    60
accaaagtgg                                                          70

<210> SEQ ID NO 22
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 43,45
<223> OTHER INFORMATION: /note="n is A, T, C, or G"

```
<400> SEQUENCE: 22
gattttgcga cctactactg tcaacagkgg kggrrythyc cgntnacctt cggtcaaggc    60
accaaagtgg                                                           70

<210> SEQ ID NO 23
<211> LENGTH: 65
<212> TYPE: DNA
<213> ORGANISM: Artificial Sequence
<220> FEATURE:
<223> OTHER INFORMATION: Synthetic

<400> SEQUENCE: 23
gagctgtgcg gcgagcgggt tcaccattrr yrrythythy attcattggg tgcgtcaagc    60
tcccg                                                                65

<210> SEQ ID NO 24
<211> LENGTH: 65
<212> TYPE: DNA
<213> ORGANISM: Artificial Sequence
<220> FEATURE:
<223> OTHER INFORMATION: Synthetic

<400> SEQUENCE: 24
gagctgtgcg gcgagcgggt tcaccattrr yrrythykgg attcattggg tgcgtcaagc    60
tcccg                                                                65

<210> SEQ ID NO 25
<211> LENGTH: 65
<212> TYPE: DNA
<213> ORGANISM: Artificial Sequence
<220> FEATURE:
<223> OTHER INFORMATION: Synthetic

<400> SEQUENCE: 25
gagctgtgcg gcgagcgggt tcaccattrr yrrykggthy attcattggg tgcgtcaagc    60
tcccg                                                                65

<210> SEQ ID NO 26
<211> LENGTH: 65
<212> TYPE: DNA
<213> ORGANISM: Artificial Sequence
<220> FEATURE:
<223> OTHER INFORMATION: Synthetic

<400> SEQUENCE: 26
gagctgtgcg gcgagcgggt tcaccattrr yrrykggkgg attcattggg tgcgtcaagc    60
tcccg                                                                65

<210> SEQ ID NO 27
<211> LENGTH: 84
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,35
<223> OTHER INFORMATION: /note="n is A, T, C, or G"

<400> SEQUENCE: 27
gcaaggggct ggagtgggtc gcgkggattk ggncnthykg gggtthyaca thytatgccg    60
acagcgtgaa aggtcgcttt acga                                           84
```

```
<210> SEQ ID NO 28
<211> LENGTH: 84
<212> TYPE: DNA
<213> ORGANISM: Artificial Sequence
<220> FEATURE:
<223> OTHER INFORMATION: Synthetic
<220> FEATURE:
<221> NAME/KEY: V_region
<222> LOCATION: 33,35
<223> OTHER INFORMATION: /note="n is A, T, C, or G"

<400> SEQUENCE: 28
gcaaggggct ggagtgggtc gcgthyattk ggncnthykg gggtthyaca thytatgccg      60
acagcgtgaa aggtcgcttt acga                                            84

<210> SEQ ID NO 29
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,32,35,38
<223> OTHER INFORMATION: /note="n is A, T, C, or G"

<400> SEQUENCE: 29
agcggtgtat tattgcgcgc gtttcnwynw ynwynwynwy kggkggatgg attattgggg      60
gcagggcacc cttg                                                       74

<210> SEQ ID NO 30
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,32,35,41
<223> OTHER INFORMATION: /note="n is A, T, C, or G"

<400> SEQUENCE: 30
agcggtgtat tattgcgcgc gtttcnwynw ynwynwykgg nwykggatgg attattgggg      60
gcagggcacc cttg                                                       74

<210> SEQ ID NO 31
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,32,38,41
<223> OTHER INFORMATION: /note="n is A, T, C, or G"

<400> SEQUENCE: 31
agcggtgtat tattgcgcgc gtttcnwynw ynwykggnwy nwykggatgg attattgggg      60
gcagggcacc cttg                                                       74

<210> SEQ ID NO 32
<211> LENGTH: 74
<212> TYPE: DNA
<213> ORGANISM: Artificial Sequence
<220> FEATURE:
```

```
<223> OTHER INFORMATION: Synthetic
<220> FEATURE:
<221> NAME/KEY: variation
<222> LOCATION: 26,29,35,38,41
<223> OTHER INFORMATION: /note="n is A, T, C, or G"

<400> SEQUENCE: 32
agcggtgtat tattgcgcgc gtttcnwynw ykggnwynwy nwykggatgg attattgggg     60
gcagggcacc cttg                                                      74

<210> SEQ ID NO 33
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,41
<223> OTHER INFORMATION: /note="n is A, T, C, or G"

<400> SEQUENCE: 33
agcggtgtat tattgcgcgc gtttcnwykg gnwynwynwy nwykggatgg attattgggg     60
gcagggcacc cttg                                                      74

<210> SEQ ID NO 34
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 29,32,35,38,41
<223> OTHER INFORMATION: /note="n is A, T, C, or G"

<400> SEQUENCE: 34
agcggtgtat tattgcgcgc gtttckggnw ynwynwynwy nwykggatgg attattgggg     60
gcagggcacc cttg                                                      74

<210> SEQ ID NO 35
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,32,35,44
<223> OTHER INFORMATION: /note="n is A, T, C, or G"

<400> SEQUENCE: 35
agcggtgtat tattgcgcgc gtttcnwynw ynwynwykgg kggnwyatgg attattgggg     60
gcagggcacc cttg                                                      74

<210> SEQ ID NO 36
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,32,38,41,44
<223> OTHER INFORMATION: /note="n is A, T, C, or G"

<400> SEQUENCE: 36
```
agcggtgtat tattgcgcgc gtttcnwynw ynwykggnwy nwynwyatgg attattgggg    60
gcagggcacc cttg                                                     74

<210> SEQ ID NO 37
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,35,38,41,44
<223> OTHER INFORMATION: /note="n is A, T, C, or G"

<400> SEQUENCE: 37
agcggtgtat tattgcgcgc gtttcnwynw ykggnwynwy nwynwyatgg attattgggg    60
gcagggcacc cttg                                                     74

<210> SEQ ID NO 38
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,41,44
<223> OTHER INFORMATION: /note="n is A, T, C, or G"

<400> SEQUENCE: 38
agcggtgtat tattgcgcgc gtttcnwykg gnwynwynwy nwynwyatgg attattgggg    60
gcagggcacc cttg                                                     74

<210> SEQ ID NO 39
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 29,32,35,38,44
<223> OTHER INFORMATION: /note="n is A, T, C, or G"

<400> SEQUENCE: 39
agcggtgtat tattgcgcgc gtttckggnw ynwynwynwy kggnwyatgg attattgggg    60
gcagggcacc cttg                                                     74

<210> SEQ ID NO 40
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: V_region
<222> LOCATION: 26,29,32,41,44
<223> OTHER INFORMATION: /note="n is A, T, C, or G"

<400> SEQUENCE: 40
agcggtgtat tattgcgcgc gtttcnwynw ynwykggkgg nwynwyatgg attattgggg    60
gcagggcacc cttg                                                     74

<210> SEQ ID NO 41

```
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,35,41,44
<223> OTHER INFORMATION: /note="n is A, T, C, or G"

<400> SEQUENCE: 41
agcggtgtat tattgcgcgc gtttcnwynw ykggnwykgg nwynwyatgg attattgggg      60
gcagggcacc cttg                                                       74

<210> SEQ ID NO 42
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,41,44
<223> OTHER INFORMATION: /note="n is A, T, C, or G"

<400> SEQUENCE: 42
agcggtgtat tattgcgcgc gtttcnwykg gnwynwykgg nwynwyatgg attattgggg      60
gcagggcacc cttg                                                       74

<210> SEQ ID NO 43
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 29,32,35,41,44
<223> OTHER INFORMATION: /note="n is A, T, C, or G"

<400> SEQUENCE: 43
agcggtgtat tattgcgcgc gtttckggnw ynwynwykgg nwynwyatgg attattgggg      60
gcagggcacc cttg                                                       74

<210> SEQ ID NO 44
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,29,38,41,44
<223> OTHER INFORMATION: /note="n is A, T, C, or G"

<400> SEQUENCE: 44
agcggtgtat tattgcgcgc gtttcnwynw ykggkggnwy nwynwyatgg attattgggg      60
gcagggcacc cttg                                                       74

<210> SEQ ID NO 45
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: V_region
```

<222> LOCATION: 26,32,38,41,44
<223> OTHER INFORMATION: /note="n is A, T, C, or G"

<400> SEQUENCE: 45
agcggtgtat tattgcgcgc gtttcnwykg gnwykggnwy nwynwyatgg attattgggg    60
gcagggcacc cttg                                                    74

<210> SEQ ID NO 46
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 29,32,38,41,44
<223> OTHER INFORMATION: /note="n is A, T, C, or G"

<400> SEQUENCE: 46
agcggtgtat tattgcgcgc gtttckggnw ynwykggnwy nwynwyatgg attattgggg    60
gcagggcacc cttg                                                    74

<210> SEQ ID NO 47
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,35,38,41,44
<223> OTHER INFORMATION: /note="n is A, T, C, or G"

<400> SEQUENCE: 47
agcggtgtat tattgcgcgc gtttcnwykg gkggnwynwy nwynwyatgg attattgggg    60
gcagggcacc cttg                                                    74

<210> SEQ ID NO 48
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 29,35,38,41,44
<223> OTHER INFORMATION: /note="n is A, T, C, or G"

<400> SEQUENCE: 48
agcggtgtat tattgcgcgc gtttckggnw ykggnwynwy nwynwyatgg attattgggg    60
gcagggcacc cttg                                                    74

<210> SEQ ID NO 49
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 32,35,38,41,44
<223> OTHER INFORMATION: /note="n is A, T, C, or G"

<400> SEQUENCE: 49
agcggtgtat tattgcgcgc gtttckggkg gnwynwynwy nwynwyatgg attattgggg    60

-continued

```
gcagggcacc cttg                                                  74

<210> SEQ ID NO 50
<211> LENGTH: 71
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,41
<223> OTHER INFORMATION: /note="n is A, T, C, or G"

<400> SEQUENCE: 50
agcggtgtat tattgcgcgc gtttcnwyrg ytmytmyrgy nwyatggatt attgggggca   60
gggcaccctt g                                                       71

<210> SEQ ID NO 51
<211> LENGTH: 77
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,47
<223> OTHER INFORMATION: /note="n is A, T, C, or G"

<400> SEQUENCE: 51
agcggtgtat tattgcgcgc gtttcnwyrg ytmyrgytmy tmyrgynwya tggattattg   60
ggggcagggc acccttg                                                 77

<210> SEQ ID NO 52
<211> LENGTH: 77
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,47
<223> OTHER INFORMATION: /note="n is A, T, C, or G"

<400> SEQUENCE: 52
agcggtgtat tattgcgcgc gtttcnwyrg ytmytmyrgy tmyrgynwya tggattattg   60
ggggcagggc acccttg                                                 77

<210> SEQ ID NO 53
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,47,53
<223> OTHER INFORMATION: /note="n is A, T, C, or G"

<400> SEQUENCE: 53
agcggtgtat tattgcgcgc gtttcnwyrg ynayrgytmy tmyrgynayr gynwyatgga   60
ttattggggg cagggcaccc ttg                                          83

<210> SEQ ID NO 54
<211> LENGTH: 83
<212> TYPE: DNA
<213> ORGANISM: Artificial Sequence
```

<220> FEATURE:
<223> OTHER INFORMATION: Synthetic
<220> FEATURE:
<221> NAME/KEY: variation
<222> LOCATION: 26,32,47,53
<223> OTHER INFORMATION: /note="n is A, T, C, or G"

<400> SEQUENCE: 54
agcggtgtat tattgcgcgc gtttcnwyrg ynaytmyrgy tmytmynayr gynwyatgga      60
ttattggggg cagggcaccc ttg                                             83

<210> SEQ ID NO 55
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,47,53
<223> OTHER INFORMATION: /note="n is A, T, C, or G"

<400> SEQUENCE: 55
agcggtgtat tattgcgcgc gtttcnwyrg ynaytmytmy rgytmynayr gynwyatgga      60
ttattggggg cagggcaccc ttg                                             83

<210> SEQ ID NO 56
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,53,59
<223> OTHER INFORMATION: /note="n is A, T, C, or G"

<400> SEQUENCE: 56
agcggtgtat tattgcgcgc gtttcnwyrg ynayrgytmy tmytmytmyr gynayrgynw      60
yatggattat tggggcagg gcacccttg                                        89

<210> SEQ ID NO 57
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,50,53,59
<223> OTHER INFORMATION: /note="n is A, T, C, or G"

<400> SEQUENCE: 57
agcggtgtat tattgcgcgc gtttcnwyrg ynaynayrgy tmytmyrgyn aynayrgynw      60
yatggattat tggggcagg gcacccttg                                        89

<210> SEQ ID NO 58
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,50,53,59
<223> OTHER INFORMATION: /note="n is A, T, C, or G"

<400> SEQUENCE: 58
agcggtgtat tattgcgcgc gtttcnwyrg ynaynaytmy rgytmytmyn aynayrgynw        60
yatggattat tggggcagg g

<210> SEQ ID NO 63
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,53,56,59,65
<223> OTHER INFORMATION: /note="n is A, T, C, or G"

<400> SEQUENCE: 63
agcggtgtat tattgcgcgc gtttcnwyrg ynaynaynay tmyrgytmyt mynaynayna    60
yrgynwyatg gattattggg ggcagggcac ccttg                              95

<210> SEQ ID NO 64
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,53,56,59,65
<223> OTHER INFORMATION: /note="n is A, T, C, or G"

<400> SEQUENCE: 64
agcggtgtat tattgcgcgc gtttcnwyrg ynaynaynay tmytmyrgyt mynaynayna    60
yrgynwyatg gattattggg ggcagggcac ccttg                              95

<210> SEQ ID NO 65
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,38,41,56,59,65,71
<223> OTHER INFORMATION: /note="n is A, T, C, or G"

<400> SEQUENCE: 65
agcggtgtat tattgcgcgc gtttcnwyrg ynayrgynay naytmytmyt mytmynayna    60
yrgynayrgy nwyatggatt attgggggca gggcacccct tg                      101

<210> SEQ ID NO 66
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,41,56,62,65,71
<223> OTHER INFORMATION: /note="n is A, T, C, or G"

<400> SEQUENCE: 66
agcggtgtat tattgcgcgc gtttcnwyrg ynaynayrgy naytmytmyt mytmynayrg    60
ynaynayrgy nwyatggatt attgggggca gggcacccct tg                      101

<210> SEQ ID NO 67
<211> LENGTH: 101
<212> TYPE: DNA
<213> ORGANISM: Artificial Sequence
<220> FEATURE:
<223> OTHER INFORMATION: Synthetic
<220> FEATURE:

<221> NAME/KEY: variation
<222> LOCATION: 26,32,35,38,59,62,65,71
<223> OTHER INFORMATION: /note="n is A, T, C, or G"

<400> SEQUENCE: 67
agcggtgtat tattgcgcgc gtttcnwyrg ynaynaynay rgytmytmyt mytmyrgyna    60
ynaynayrgy nwyatggatt attgggggca gggcaccctt g    101

<210> SEQ ID NO 68
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: V_region
<222> LOCATION: 26,32,35,38,41,56,59,62,65,71
<223> OTHER INFORMATION: /note="n is A, T, C, or G"

<400> SEQUENCE: 68
agcggtgtat tattgcgcgc gtttcnwyrg ynaynaynay nayrgytmyt myrgynayna    60
ynaynayrgy nwyatggatt attgggggca gggcaccctt g    101

<210> SEQ ID NO 69
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,41,56,59,62,65,71
<223> OTHER INFORMATION: /note="n is A, T, C, or G"

<400> SEQUENCE: 69
agcggtgtat tattgcgcgc gtttcnwyrg ynaynaynay naytmyrgyt mytmynayna    60
ynaynayrgy nwyatggatt attgggggca gggcaccctt g    101

<210> SEQ ID NO 70
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,41,56,59,62,65,71
<223> OTHER INFORMATION: /note="n is A, T, C, or G"

<400> SEQUENCE: 70
agcggtgtat tattgcgcgc gtttcnwyrg ynaynaynay naytmytmyr gytmynayna    60
ynaynayrgy nwyatggatt attgggggca gggcaccctt g    101

<210> SEQ ID NO 71
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,38,41,44,59,62,65,71,77
<223> OTHER INFORMATION: /note="n is A, T, C, or G"

<400> SEQUENCE: 71
agcggtgtat tattgcgcgc gtttcnwyrg ynayrgynay naynaytmyt mytmytmyna    60
ynaynayrgy nayrgynwya tggattattg ggggcagggc acccttg         107

<210> SEQ ID NO 72
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,41,44,59,62,68,71,77
<223> OTHER INFORMATION: /note="n is A, T, C, or G"

<400> SEQUENCE: 72
agcggtgtat tattgcgcgc gtttcnwyrg ynaynayrgy naynaytmyt mytmytmyna    60
ynayrgynay nayrgynwya tggattattg ggggcagggc acccttg               107

<210> SEQ ID NO 73
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,44,59,65,68,71,77
<223> OTHER INFORMATION: /note="n is A, T, C, or G"

<400> SEQUENCE: 73
agcggtgtat tattgcgcgc gtttcnwyrg ynaynaynay rgynaytmyt mytmytmyna    60
yrgynaynay nayrgynwya tggattattg ggggcagggc acccttg               107

<210> SEQ ID NO 74
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: V_region
<222> LOCATION: 26,32,35,38,41,62,65,68,71,77
<223> OTHER INFORMATION: /note="n is A, T, C, or G"

<400> SEQUENCE: 74
agcggtgtat tattgcgcgc gtttcnwyrg ynaynaynay nayrgytmyt mytmytmyrg    60
ynaynaynay nayrgynwya tggattattg ggggcagggc acccttg               107

<210> SEQ ID NO 75
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,41,44,59,62,65,68,71,77
<223> OTHER INFORMATION: /note="n is A, T, C, or G"

<400> SEQUENCE: 75
agcggtgtat tattgcgcgc gtttcnwyrg ynaynaynay naynayrgyt mytmyrgyna    60
ynaynaynay nayrgynwya tggattattg ggggcagggc acccttg               107

<210> SEQ ID NO 76
<211> LENGTH: 107
<212> TYPE: DNA

<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,41,44,59,62,65,68,71,77
<223> OTHER INFORMATION: /note="n is A, T, C, or G"

<400> SEQUENCE: 76
agcggtgtat tattgcgcgc gtttcnwyrg ynaynaynay naynaytmyr gytmytmyna    60
ynaynaynay nayrgynwya tggattattg ggggcagggc acccttg                 107

<210> SEQ ID NO 77
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,32,35,38,41,44,59,62,65,68,71,77
<223> OTHER INFORMATION: /note="n is A, T, C, or G"

<400> SEQUENCE: 77
agcggtgtat tattgcgcgc gtttcnwyrg ynaynaynay naynaytmyt myrgytmyna    60
ynaynaynay nayrgynwya tggattattg ggggcagggc acccttg                 107

<210> SEQ ID NO 78
<211> LENGTH: 75
<212> TYPE: DNA
<213> ORGANISM: Artificial Sequence
<220> FEATURE:
<223> OTHER INFORMATION: Synthetic

<400> SEQUENCE: 78
cacagcggtg tattattgcg cgcgtkggth ythykggthy thythygatt attgggggca    60 gggcacccctt gttac                                                    75

<210> SEQ ID NO 79
<211> LENGTH: 75
<212> TYPE: DNA
<213> ORGANISM: Artificial Sequence
<220> FEATURE:
<223> OTHER INFORMATION: Synthetic

<400> SEQUENCE: 79
cacagcggtg tattattgcg cgcgtkggth ythythykgg thythygatt attgggggca    60 gggcacccctt gttac                                                    75

<210> SEQ ID NO 80
<211> LENGTH: 75
<212> TYPE: DNA
<213> ORGANISM: Artificial Sequence
<220> FEATURE:
<223> OTHER INFORMATION: Synthetic

<400> SEQUENCE: 80
cacagcggtg tattattgcg cgcgtkggth ythythythy kggthygatt attgggggca    60 gggcacccctt gttac                                                    75

<210> SEQ ID NO 81
<211> LENGTH: 75
<212> TYPE: DNA
<213> ORGANISM: Artificial Sequence

```
<220> FEATURE:
<223> OTHER INFORMATION: Synthetic

<400> SEQUENCE: 81
cacagcggtg tattattgcg cgcgtkggth ythythythy thykgggatt attgggggca    60
gggcaccctt gttac                                                    75

<210> SEQ ID NO 82
<211> LENGTH: 75
<212> TYPE: DNA
<213> ORGANISM: Artificial Sequence
<220> FEATURE:
<223> OTHER INFORMATION: Synthetic

<400> SEQUENCE: 82
cacagcggtg tattattgcg cgcgtthykg gthythykgg thythygatt attgggggca    60
gggcaccctt gttac                                                    75

<210> SEQ ID NO 83
<211> LENGTH: 75
<212> TYPE: DNA
<213> ORGANISM: Artificial Sequence
<220> FEATURE:
<223> OTHER INFORMATION: Synthetic

<400> SEQUENCE: 83
cacagcggtg tattattgcg cgcgtthykg gthythythy kggthygatt attgggggca    60
gggcaccctt gttac                                                    75

<210> SEQ ID NO 84
<211> LENGTH: 75
<212> TYPE: DNA
<213> ORGANISM: Artificial Sequence
<220> FEATURE:
<223> OTHER INFORMATION: Synthetic

<400> SEQUENCE: 84
cacagcggtg tattattgcg cgcgtthykg gthythythy thykgggatt attgggggca    60
gggcaccctt gttac                                                    75

<210> SEQ ID NO 85
<211> LENGTH: 75
<212> TYPE: DNA
<213> ORGANISM: Artificial Sequence
<220> FEATURE:
<223> OTHER INFORMATION: Synthetic

<400> SEQUENCE: 85
cacagcggtg tattattgcg cgcgtthyth ykggthythy kggthygatt attgggggca    60
gggcaccctt gttac                                                    75

<210> SEQ ID NO 86
<211> LENGTH: 75
<212> TYPE: DNA
<213> ORGANISM: Artificial Sequence
<220> FEATURE:
<223> OTHER INFORMATION: Synthetic

<400> SEQUENCE: 86
cacagcggtg tattattgcg cgcgtthyth ykggthythy thykgggatt attgggggca    60
gggcaccctt gttac                                                    75
```

<210> SEQ ID NO 87
<211> LENGTH: 75
<212> TYPE: DNA
<213> ORGANISM: Artificial Sequence
<220> FEATURE:
<223> OTHER INFORMATION: Synthetic

<400> SEQUENCE: 87
cacagcggtg tattattgcg cgcgtthyth ythykggthy thykgggatt attgggggca      60
gggcacccTT gttac      75

<210> SEQ ID NO 88
<211> LENGTH: 72
<212> TYPE: DNA
<213> ORGANISM: Artificial Sequence
<220> FEATURE:
<223> OTHER INFORMATION: Synthetic

<400> SEQUENCE: 88
cacagcggtg tattattgcg cgcgtkggth ythykggthy thygattatt ggggggcaggg      60 caccctTgtt ac      72

<210> SEQ ID NO 89
<211> LENGTH: 72
<212> TYPE: DNA
<213> ORGANISM: Artificial Sequence
<220> FEATURE:
<223> OTHER INFORMATION: Synthetic

<400> SEQUENCE: 89
cacagcggtg tattattgcg cgcgtkggth ythythykgg thygattatt ggggggcaggg      60 cacccTtgtt ac      72

<210> SEQ ID NO 90
<211> LENGTH: 72
<212> TYPE: DNA
<213> ORGANISM: Artificial Sequence
<220> FEATURE:
<223> OTHER INFORMATION: Synthetic

<400> SEQUENCE: 90
cacagcggtg tattattgcg cgcgtkggth ythythythy kgggattatt ggggggcaggg      60 cacccTtgtt ac      72

<210> SEQ ID NO 91
<211> LENGTH: 72
<212> TYPE: DNA
<213> ORGANISM: Artificial Sequence
<220> FEATURE:
<223> OTHER INFORMATION: Synthetic

<400> SEQUENCE: 91
cacagcggtg tattattgcg cgcgtthykg gthythykgg thygattatt ggggggcaggg      60 cacccTtgtt ac      72

<210> SEQ ID NO 92
<211> LENGTH: 72
<212> TYPE: DNA
<213> ORGANISM: Artificial Sequence
<220> FEATURE:
<223> OTHER INFORMATION: Synthetic

<400> SEQUENCE: 92
cacagcggtg tattattgcg cgcgtthykg gthythythy kgggattatt gggggcaggg    60 caccccttgtt ac    72

<210> SEQ ID NO 93
<211> LENGTH: 72
<212> TYPE: DNA
<213> ORGANISM: Artificial Sequence
<220> FEATURE:
<223> OTHER INFORMATION: Synthetic

<400> SEQUENCE: 93
cacagcggtg tattattgcg cgcgtthyth ykggthythy kgggattatt gggggcaggg    60 caccccttgtt ac    72

<210> SEQ ID NO 94
<211> LENGTH: 69
<212> TYPE: DNA
<213> ORGANISM: Artificial Sequence
<220> FEATURE:
<223> OTHER INFORMATION: Synthetic

<400> SEQUENCE: 94
cacagcggtg tattattgcg cgcgtkggth ythykggthy gattattggg ggcagggcac    60
ccttgttac    69

<210> SEQ ID NO 95
<211> LENGTH: 69
<212> TYPE: DNA
<213> ORGANISM: Artificial Sequence
<220> FEATURE:
<223> OTHER INFORMATION: Synthetic

<400> SEQUENCE: 95
cacagcggtg tattattgcg cgcgtkggth ythythykgg gattattggg ggcagggcac    60
ccttgttac    69

<210> SEQ ID NO 96
<211> LENGTH: 69
<212> TYPE: DNA
<213> ORGANISM: Artificial Sequence
<220> FEATURE:
<223> OTHER INFORMATION: Synthetic

<400> SEQUENCE: 96
cacagcggtg tattattgcg cgcgtthykg gthythykgg gattattggg ggcagggcac    60
ccttgttac    69

<210> SEQ ID NO 97
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31, 46
<223> OTHER INFORMATION: /note="n is A, T, C, or G"

<400> SEQUENCE: 97
gcggaagaca cagcggtgta ttattgcgcg nggkggthyk ggthynayta ttgggggcag    60
ggcacccttg ttaccgtg    78

<210> SEQ ID NO 98
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,46
<223> OTHER INFORMATION: /note="n is A, T, C, or G"

<400> SEQUENCE: 98
gcggaagaca cagcggtgta ttattgcgcg nggkggthyt hykggnayta ttgggggcag    60
ggcacccttg ttaccgtg                                                 78

<210> SEQ ID NO 99
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,46
<223> OTHER INFORMATION: /note="n is A, T, C, or G"

<400> SEQUENCE: 99
gcggaagaca cagcggtgta ttattgcgcg nggthykggt hykggnayta ttgggggcag    60
ggcacccttg ttaccgtg                                                 78

<210> SEQ ID NO 100
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,43
<223> OTHER INFORMATION: /note="n is A, T, C, or G"

<400> SEQUENCE: 100
gcggaagaca cagcggtgta ttattgcgcg nggkggthyt hynaytattg ggggcagggc    60
acccttgtta ccgtg                                                    75

<210> SEQ ID NO 101
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,43
<223> OTHER INFORMATION: /note="n is A, T, C, or G"

<400> SEQUENCE: 101
gcggaagaca cagcggtgta ttattgcgcg nggthykggt hynaytattg ggggcagggc    60
acccttgtta ccgtg                                                    75

<210> SEQ ID NO 102
<211> LENGTH: 75
<212> TYPE: DNA
<213> ORGANISM: Artificial Sequence
<220> FEATURE:
<223> OTHER INFORMATION: Synthetic

```
<220> FEATURE:
<221> NAME/KEY: V_region
<222> LOCATION: 31,43
<223> OTHER INFORMATION: /note="n is A, T, C, or G"

<400> SEQUENCE: 102
gcggaagaca cagcggtgta ttattgcgcg nggthythyk ggnaytattg ggggcagggc    60
acccttgtta ccgtg                                                    75

<210> SEQ ID NO 103
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,40
<223> OTHER INFORMATION: /note="n is A, T, C, or G"

<400> SEQUENCE: 103
gcggaagaca cagcggtgta ttattgcgcg nggkggthyn aytattgggg gcagggcacc    60
cttgttaccg tg                                                       72

<210> SEQ ID NO 104
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,40
<223> OTHER INFORMATION: /note="n is A, T, C, or G"

<400> SEQUENCE: 104
gcggaagaca cagcggtgta ttattgcgcg nggthykggn aytattgggg gcagggcacc    60
cttgttaccg tg                                                       72

<210> SEQ ID NO 105
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37
<223> OTHER INFORMATION: /note="n is A, T, C, or G"

<400> SEQUENCE: 105
gcggaagaca cagcggtgta ttattgcgcg nggkggnayt attgggggca gggcaccctt    60
gttaccgtg                                                           69

<210> SEQ ID NO 106
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37
<223> OTHER INFORMATION: /note="n is A, T, C, or G"

<400> SEQUENCE: 106
```

```
gcggaagaca cagcggtgta ttattgcgcg nggthynayt attgggggca gggcacccttt    60 gttaccgtg                                                             69

<210> SEQ ID NO 107
<211> LENGTH: 64
<212> TYPE: DNA
<213> ORGANISM: Artificial Sequence
<220> FEATURE:
<223> OTHER INFORMATION: Synthetic

<400> SEQUENCE: 107
tggtttctgc tgataccatg cgacrdarda rdaaacatcc tggctcgcac ggcaggtaat    60
ggtc                                                                  64

<210> SEQ ID NO 108
<211> LENGTH: 64
<212> TYPE: DNA
<213> ORGANISM: Artificial Sequence
<220> FEATURE:
<223> OTHER INFORMATION: Synthetic

<400> SEQUENCE: 108
tggtttctgc tgataccatg cgacccmrda rdaaacatcc tggctcgcac ggcaggtaat    60
ggtc                                                                  64

<210> SEQ ID NO 109
<211> LENGTH: 64
<212> TYPE: DNA
<213> ORGANISM: Artificial Sequence
<220> FEATURE:
<223> OTHER INFORMATION: Synthetic

<400> SEQUENCE: 109
tggtttctgc tgataccatg cgacccmccm rdaaacatcc tggctcgcac ggcaggtaat    60
ggtc                                                                  64

<210> SEQ ID NO 110
<211> LENGTH: 64
<212> TYPE: DNA
<213> ORGANISM: Artificial Sequence
<220> FEATURE:
<223> OTHER INFORMATION: Synthetic

<400> SEQUENCE: 110
tggtttctgc tgataccatg cgacrdaccm rdaaacatcc tggctcgcac ggcaggtaat    60
ggtc                                                                  64

<210> SEQ ID NO 111
<211> LENGTH: 64
<212> TYPE: DNA
<213> ORGANISM: Artificial Sequence
<220> FEATURE:
<223> OTHER INFORMATION: Synthetic

<400> SEQUENCE: 111
tggtttctgc tgataccatg cgacrdarda ccmaacatcc tggctcgcac ggcaggtaat    60
ggtc                                                                  64

<210> SEQ ID NO 112
<211> LENGTH: 64
<212> TYPE: DNA
<213> ORGANISM: Artificial Sequence
```

<220> FEATURE:
<223> OTHER INFORMATION: Synthetic

<400> SEQUENCE: 112
tggtttctgc tgataccatg cgacccmrda ccmaacatcc tggctcgcac ggcaggtaat    60
ggtc    64

<210> SEQ ID NO 113
<211> LENGTH: 64
<212> TYPE: DNA
<213> ORGANISM: Artificial Sequence
<220> FEATURE:
<223> OTHER INFORMATION: Synthetic

<400> SEQUENCE: 113
tggtttctgc tgataccatg cgacccmccm ccmaacatcc tggctcgcac ggcaggtaat    60
ggtc    64

<210> SEQ ID NO 114
<211> LENGTH: 64
<212> TYPE: DNA
<213> ORGANISM: Artificial Sequence
<220> FEATURE:
<223> OTHER INFORMATION: Synthetic

<400> SEQUENCE: 114
tggtttctgc tgataccatg cgacrdaccm ccmaacatcc tggctcgcac ggcaggtaat    60
ggtc    64

<210> SEQ ID NO 115
<211> LENGTH: 64
<212> TYPE: DNA
<213> ORGANISM: Artificial Sequence
<220> FEATURE:
<223> OTHER INFORMATION: Synthetic

<400> SEQUENCE: 115
tggtttctgc tgataccatg cgacryyryy ryyaacatcc tggctcgcac ggcaggtaat    60
ggtc    64

<210> SEQ ID NO 116
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 37,39
<223> OTHER INFORMATION: /note="n is A, T, C, or G"

<400> SEQUENCE: 116
cgaaaaacgc gacggcacgc cgctatacag rdarsbngnr dardatatca gaagtttcgg    60
cgctttgcc    69

<210> SEQ ID NO 117
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 37,39

<223> OTHER INFORMATION: /note="n is A, T, C, or G"

<400> SEQUENCE: 117
cgaaaaacgc gacggcacgc cgctatacag ccmrsbngnr dardatatca gaagtttcgg    60
cgctttgcc                                                           69

<210> SEQ ID NO 118
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 37,39
<223> OTHER INFORMATION: /note="n is A, T, C, or G"

<400> SEQUENCE: 118
cgaaaaacgc gacggcacgc cgctatacag ccmrsbngnc cmrdatatca gaagtttcgg    60
cgctttgcc                                                           69

<210> SEQ ID NO 119
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 37,39
<223> OTHER INFORMATION: /note="n is A, T, C, or G"

<400> SEQUENCE: 119
cgaaaaacgc gacggcacgc cgctatacag rdarsbngnc cmrdatatca gaagtttcgg    60
cgctttgcc                                                           69

<210> SEQ ID NO 120
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 120
ccactttggt gccttgaccg aaggtnancg grdaryyrda rdactgttga cagtagtagg    60
tcgcaaaatc                                                          70

<210> SEQ ID NO 121
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 121
ccactttggt gccttgaccg aaggtnancg gccmryyrda rdactgttga cagtagtagg    60
tcgcaaaatc                                                          70

<210> SEQ ID NO 122
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 122
ccactttggt gccttgaccg aaggtnancg gccmryyccm rdactgttga cagtagtagg      60
tcgcaaaatc                                                            70

<210> SEQ ID NO 123
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 123
ccactttggt gccttgaccg aaggtnancg grdaryyccm rdactgttga cagtagtagg      60
tcgcaaaatc                                                            70

<210> SEQ ID NO 124
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 124
ccactttggt gccttgaccg aaggtnancg grdaryyrda ccmctgttga cagtagtagg      60
tcgcaaaatc                                                            70

<210> SEQ ID NO 125
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 125
ccactttggt gccttgaccg aaggtnancg gccmryyrda ccmctgttga cagtagtagg      60
tcgcaaaatc                                                            70

<210> SEQ ID NO 126
<211> LENGTH: 70
<212> TYPE: DNA
<213> ORGANISM: Artificial Sequence
<220> FEATURE:

<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 126
ccactttggt gccttgaccg aaggtnancg gccmryyccm ccmctgttga cagtagtagg        60
tcgcaaaatc                                                              70

<210> SEQ ID NO 127
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 26,28
<223> OTHER INFORMATION: /note="n is A, T, C, or G"

<400> SEQUENCE: 127
ccactttggt gccttgaccg aaggtnancg grdaryyccm ccmctgttga cagtagtagg        60
tcgcaaaatc                                                              70

<210> SEQ ID NO 128
<211> LENGTH: 65
<212> TYPE: DNA
<213> ORGANISM: Artificial Sequence
<220> FEATURE:
<223> OTHER INFORMATION: Synthetic

<400> SEQUENCE: 128
cgggagcttg acgcacccaa tgaatrdard aryyryyaat ggtgaacccg ctcgccgcac        60
agctc                                                                   65

<210> SEQ ID NO 129
<211> LENGTH: 65
<212> TYPE: DNA
<213> ORGANISM: Artificial Sequence
<220> FEATURE:
<223> OTHER INFORMATION: Synthetic

<400> SEQUENCE: 129
cgggagcttg acgcacccaa tgaatccmrd aryyryyaat ggtgaacccg ctcgccgcac        60
agctc                                                                   65

<210> SEQ ID NO 130
<211> LENGTH: 65
<212> TYPE: DNA
<213> ORGANISM: Artificial Sequence
<220> FEATURE:
<223> OTHER INFORMATION: Synthetic

<400> SEQUENCE: 130
cgggagcttg acgcacccaa tgaatrdacc mryyryyaat ggtgaacccg ctcgccgcac        60
agctc                                                                   65

<210> SEQ ID NO 131
<211> LENGTH: 65
<212> TYPE: DNA
<213> ORGANISM: Artificial Sequence
<220> FEATURE:
<223> OTHER INFORMATION: Synthetic

<400> SEQUENCE: 131
cgggagcttg acgcacccaa tgaatccmcc mryyryyaat ggtgaacccg ctcgccgcac    60
agctc                                                                65

<210> SEQ ID NO 132
<211> LENGTH: 84
<212> TYPE: DNA
<213> ORGANISM: Artificial Sequence
<220> FEATURE:
<223> OTHER INFORMATION: Synthetic

<400> SEQUENCE: 132
tcgtaaagcg acctttcacg ctgtcggcat ardatgtrda accccmrdag ggccmaatcc    60
mcgcgaccca ctccagcccc ttgc                                           84

<210> SEQ ID NO 133
<211> LENGTH: 84
<212> TYPE: DNA
<213> ORGANISM: Artificial Sequence
<220> FEATURE:
<223> OTHER INFORMATION: Synthetic

<400> SEQUENCE: 133
tcgtaaagcg acctttcacg ctgtcggcat ardatgtrda accccmrdag ggccmaatrd    60
acgcgaccca ctccagcccc ttgc                                           84

<210> SEQ ID NO 134
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 37,40,43,46,49
<223> OTHER INFORMATION: /note="n is A, T, C, or G"

<400> SEQUENCE: 134
caagggtgcc ctgcccccaa taatccatcc mccmrwnrwn rwnrwnrwng aaacgcgcgc    60
aataatacac cgct                                                      74

<210> SEQ ID NO 135
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 34,40,43,46,49
<223> OTHER INFORMATION: /note="n is A, T, C, or G"

<400> SEQUENCE: 135
caagggtgcc ctgcccccaa taatccatcc mrwnccmrwn rwnrwnrwng aaacgcgcgc    60
aataatacac cgct                                                      74

<210> SEQ ID NO 136
<211> LENGTH: 74
<212> TYPE: DNA
<213> ORGANISM: Artificial Sequence
<220> FEATURE:
<223> OTHER INFORMATION: Synthetic
<220> FEATURE:

<221> NAME/KEY: variation
<222> LOCATION: 34,37,43,46,49
<223> OTHER INFORMATION: /note="n is A, T, C, or G"

<400> SEQUENCE: 136
caagggtgcc ctgcccccaa taatccatcc mrwnrwnccm rwnrwnrwng aaacgcgcgc    60
aataatacac cgct    74

<210> SEQ ID NO 137
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 34,37,40,46,49
<223> OTHER INFORMATION: /note="n is A, T, C, or G"

<400> SEQUENCE: 137
caagggtgcc ctgcccccaa taatccatcc mrwnrwnrwn ccmrwnrwng aaacgcgcgc    60
aataatacac cgct    74

<210> SEQ ID NO 138
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 34,37,40,43,49
<223> OTHER INFORMATION: /note="n is A, T, C, or G"

<400> SEQUENCE: 138
caagggtgcc ctgcccccaa taatccatcc mrwnrwnrwn rwnccmrwng aaacgcgcgc    60
aataatacac cgct    74

<210> SEQ ID NO 139
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 34,37,40,43,46
<223> OTHER INFORMATION: /note="n is A, T, C, or G"

<400> SEQUENCE: 139
caagggtgcc ctgcccccaa taatccatcc mrwnrwnrwn rwnrwnccmg aaacgcgcgc    60
aataatacac cgct    74

<210> SEQ ID NO 140
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,40,43,46,49
<223> OTHER INFORMATION: /note="n is A, T, C, or G"

<400> SEQUENCE: 140
caagggtgcc ctgcccccaa taatccatrw nccmccmrwn rwnrwnrwng aaacgcgcgc    60
aataatacac cgct 74

<210> SEQ ID NO 141
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,43,46,49
<223> OTHER INFORMATION: /note="n is A, T, C, or G"

<400> SEQUENCE: 141
caagggtgcc ctgcccccaa taatccatrw nccmrwnccm rwnrwnrwng aaacgcgcgc 60
aataatacac cgct 74

<210> SEQ ID NO 142
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,46,49
<223> OTHER INFORMATION: /note="n is A, T, C, or G"

<400> SEQUENCE: 142
caagggtgcc ctgcccccaa taatccatrw nccmrwnrwn ccmrwnrwng aaacgcgcgc 60
aataatacac cgct 74

<210> SEQ ID NO 143
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,49
<223> OTHER INFORMATION: /note="n is A, T, C, or G"

<400> SEQUENCE: 143
caagggtgcc ctgcccccaa taatccatrw nccmrwnrwn rwnccmrwng aaacgcgcgc 60
aataatacac cgct 74

<210> SEQ ID NO 144
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,46
<223> OTHER INFORMATION: /note="n is A, T, C, or G"

<400> SEQUENCE: 144
caagggtgcc ctgcccccaa taatccatrw nccmrwnrwn rwnrwnccmg aaacgcgcgc 60
aataatacac cgct 74

<210> SEQ ID NO 145
<211> LENGTH: 74
<212> TYPE: DNA

<213> ORGANISM: Artificial Sequence
<220> FEATURE:
<223> OTHER INFORMATION: Synthetic
<220> FEATURE:
<221> NAME/KEY: variation
<222> LOCATION: 31,34,43,46,49
<223> OTHER INFORMATION: /note="n is A, T, C, or G"

<400> SEQUENCE: 145
caagggtgcc ctgcccccaa taatccatrw nrwnccmccm rwnrwnrwng aaacgcgcgc    60
aataatacac cgct    74

<210> SEQ ID NO 146
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,40,46,49
<223> OTHER INFORMATION: /note="n is A, T, C, or G"

<400> SEQUENCE: 146
caagggtgcc ctgccccaa taatccatrw nrwnccmrwn ccmrwnrwng aaacgcgcgc    60
aataatacac cgct    74

<210> SEQ ID NO 147
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,40,43,49
<223> OTHER INFORMATION: /note="n is A, T, C, or G"

<400> SEQUENCE: 147
caagggtgcc ctgccccaa taatccatrw nrwnccmrwn rwnccmrwng aaacgcgcgc    60
aataatacac cgct    74

<210> SEQ ID NO 148
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,40,43,46
<223> OTHER INFORMATION: /note="n is A, T, C, or G"

<400> SEQUENCE: 148
caagggtgcc ctgccccaa taatccatrw nrwnccmrwn rwnrwnccmg aaacgcgcgc    60
aataatacac cgct    74

<210> SEQ ID NO 149
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,37,46,49
<223> OTHER INFORMATION: /note="n is A, T, C, or G"

<400> SEQUENCE: 149
caagggtgcc ctgcccccaa taatccatrw nrwnrwnccm ccmrwnrwng aaacgcgcgc    60
aataatacac cgct    74

<210> SEQ ID NO 150
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,37,43,49
<223> OTHER INFORMATION: /note="n is A, T, C, or G"

<400> SEQUENCE: 150
caagggtgcc ctgcccccaa taatccatrw nrwnrwnccm rwnccmrwng aaacgcgcgc    60
aataatacac cgct    74

<210> SEQ ID NO 151
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,37,43,46
<223> OTHER INFORMATION: /note="n is A, T, C, or G"

<400> SEQUENCE: 151
caagggtgcc ctgcccccaa taatccatrw nrwnrwnccm rwnrwnccmg aaacgcgcgc    60
aataatacac cgct    74

<210> SEQ ID NO 152
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,37,40,49
<223> OTHER INFORMATION: /note="n is A, T, C, or G"

<400> SEQUENCE: 152
caagggtgcc ctgcccccaa taatccatrw nrwnrwnrwn ccmccmrwng aaacgcgcgc    60
aataatacac cgct    74

<210> SEQ ID NO 153
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,37,40,46
<223> OTHER INFORMATION: /note="n is A, T, C, or G"

<400> SEQUENCE: 153
caagggtgcc ctgcccccaa taatccatrw nrwnrwnrwn ccmrwnccmg aaacgcgcgc    60
aataatacac cgct    74

<210> SEQ ID NO 154
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,34,37,40,43
<223> OTHER INFORMATION: /note="n is A, T, C, or G"

<400> SEQUENCE: 154
caagggtgcc ctgcccccaa taatccatrw nrwnrwnrwn rwnccmccmg aaacgcgcgc    60
aataatacac cgct                                                    74

<210> SEQ ID NO 155
<211> LENGTH: 71
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,46
<223> OTHER INFORMATION: /note="n is A, T, C, or G"

<400> SEQUENCE: 155
caagggtgcc ctgcccccaa taatccatrw nrcyrkarka rcyrwngaaa cgcgcgcaat    60
aatacaccgc t                                                       71

<210> SEQ ID NO 156
<211> LENGTH: 77
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,52
<223> OTHER INFORMATION: /note="n is A, T, C, or G"

<400> SEQUENCE: 156
caagggtgcc ctgcccccaa taatccatrw nrcyrkarka rcyrkarcyr wngaaacgcg    60
cgcaataata caccgct                                                 77

<210> SEQ ID NO 157
<211> LENGTH: 77
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,52
<223> OTHER INFORMATION: /note="n is A, T, C, or G"

<400> SEQUENCE: 157
caagggtgcc ctgcccccaa taatccatrw nrcyrkarcy rkarkarcyr wngaaacgcg    60
cgcaataata caccgct                                                 77

<210> SEQ ID NO 158
<211> LENGTH: 83
<212> TYPE: DNA
<213> ORGANISM: Artificial Sequence
<220> FEATURE:
<223> OTHER INFORMATION: Synthetic

```
<220> FEATURE:
<221> NAME/KEY: variation
<222> LOCATION: 31,37,52,58
<223> OTHER INFORMATION: /note="n is A, T, C, or G"

<400> SEQUENCE: 158
caagggtgcc ctgcccccaa taatccatrw nrcyrtnrcy rkarkarcyr tnrcyrwnga      60
aacgcgcgca ataatacacc gct                                             83

<210> SEQ ID NO 159
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,52,58
<223> OTHER INFORMATION: /note="n is A, T, C, or G"

<400> SEQUENCE: 159
caagggtgcc ctgcccccaa taatccatrw nrcyrtnrka rkarcyrkar tnrcyrwnga      60
aacgcgcgca ataatacacc gct                                             83

<210> SEQ ID NO 160
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,52,58
<223> OTHER INFORMATION: /note="n is A, T, C, or G"

<400> SEQUENCE: 160
caagggtgcc ctgcccccaa taatccatrw nrcyrtnrka rcyrkarkar tnrcyrwnga      60
aacgcgcgca ataatacacc gct                                             83

<210> SEQ ID NO 161
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,58,64
<223> OTHER INFORMATION: /note="n is A, T, C, or G"

<400> SEQUENCE: 161
caagggtgcc ctgcccccaa taatccatrw nrcyrtnrcy rkarkarkar karcyrtnrc      60
yrwngaaacg cgcgcaataa tacaccgct                                       89

<210> SEQ ID NO 162
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,55,58,64
<223> OTHER INFORMATION: /note="n is A, T, C, or G"

<400> SEQUENCE: 162
```
caagggtgcc ctgcccccaa taatccatrw nrcyrtnrtn rcyrkarkar cyrtnrtnrc    60
yrwngaaacg cgcgcaataa tacaccgct                                     89

<210> SEQ ID NO 163
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,55,58,64
<223> OTHER INFORMATION: /note="n is A, T, C, or G"

<400> SEQUENCE: 163
caagggtgcc ctgcccccaa taatccatrw nrcyrtnrtn rkarkarcyr kartnrtnrc    60
yrwngaaacg cgcgcaataa tacaccgct                                     89

<210> SEQ ID NO 164
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,55,58,64
<223> OTHER INFORMATION: /note="n is A, T, C, or G"

<400> SEQUENCE: 164
caagggtgcc ctgcccccaa taatccatrw nrcyrtnrtn rkarcyrkar kartnrtnrc    60
yrwngaaacg cgcgcaataa tacaccgct                                     89

<210> SEQ ID NO 165
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,43,58,64,70
<223> OTHER INFORMATION: /note="n is A, T, C, or G"

<400> SEQUENCE: 165
caagggtgcc ctgcccccaa taatccatrw nrcyrtnrcy rtnrkarkar karkartnrc    60
yrtnrcyrwn gaaacgcgcg caataataca ccgct                              95

<210> SEQ ID NO 166
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,61,64,70
<223> OTHER INFORMATION: /note="n is A, T, C, or G"

<400> SEQUENCE: 166
caagggtgcc ctgcccccaa taatccatrw nrcyrtnrtn rcyrkarkar karkarcyrt    60
nrtnrcyrwn gaaacgcgcg caataataca ccgct                              95

<210> SEQ ID NO 167
<211> LENGTH: 95

```
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,58,61,64,70
<223> OTHER INFORMATION: /note="n is A, T, C, or G"

<400> SEQUENCE: 167
caagggtgcc ctgccccaa taatccatrw nrcyrtnrtn rtnrcyrkar karcyrtnrt      60
nrtnrcyrwn gaaacgcgcg caataataca ccgct                                95

<210> SEQ ID NO 168
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,58,61,64,70
<223> OTHER INFORMATION: /note="n is A, T, C, or G"

<400> SEQUENCE: 168
caagggtgcc ctgccccaa taatccatrw nrcyrtnrtn rtnrkarkar cyrkartnrt      60
nrtnrcyrwn gaaacgcgcg caataataca ccgct                                95

<210> SEQ ID NO 169
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,58,61,64,70
<223> OTHER INFORMATION: /note="n is A, T, C, or G"

<400> SEQUENCE: 169
caagggtgcc ctgccccaa taatccatrw nrcyrtnrtn rtnrkarcyr karkartnrt      60
nrtnrcyrwn gaaacgcgcg caataataca ccgct                                95

<210> SEQ ID NO 170
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,43,46,61,64,70,76
<223> OTHER INFORMATION: /note="n is A, T, C, or G"

<400> SEQUENCE: 170
caagggtgcc ctgccccaa taatccatrw nrcyrtnrcy rtnrtnrkar karkarkart     60
nrtnrcyrtn rcyrwngaaa cgcgcgcaat aatacaccgc t                        101

<210> SEQ ID NO 171
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,46,61,67,70,76
```

<223> OTHER INFORMATION: /note="n is A, T, C, or G"

<400> SEQUENCE: 171
caagggtgcc ctgcccccaa taatccatrw nrcyrtnrtn rcyrtnrkar karkarkart    60
nrcyrtnrtn rcyrwngaaa cgcgcgcaat aatacaccgc t    101

<210> SEQ ID NO 172
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,64,67,70,76
<223> OTHER INFORMATION: /note="n is A, T, C, or G"

<400> SEQUENCE: 172
caagggtgcc ctgcccccaa taatccatrw nrcyrtnrtn rtnrcyrkar karkarkarc    60
yrtnrtnrtn rcyrwngaaa cgcgcgcaat aatacaccgc t    101

<210> SEQ ID NO 173
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,46,61,64,67,70,76
<223> OTHER INFORMATION: /note="n is A, T, C, or G"

<400> SEQUENCE: 173
caagggtgcc ctgcccccaa taatccatrw nrcyrtnrtn rtnrtnrcyr karkarcyrt    60
nrtnrtnrtn rcyrwngaaa cgcgcgcaat aatacaccgc t    101

<210> SEQ ID NO 174
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,46,61,64,67,70,76
<223> OTHER INFORMATION: /note="n is A, T, C, or G"

<400> SEQUENCE: 174
caagggtgcc ctgcccccaa taatccatrw nrcyrtnrtn rtnrtnrkar karcyrkart    60
nrtnrtnrtn rcyrwngaaa cgcgcgcaat aatacaccgc t    101

<210> SEQ ID NO 175
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,46,61,64,67,70,76
<223> OTHER INFORMATION: /note="n is A, T, C, or G"

<400> SEQUENCE: 175
caagggtgcc ctgcccccaa taatccatrw nrcyrtnrtn rtnrtnrkar cyrkarkart    60
nrtnrtnrtn rcyrwngaaa cgcgcgcaat aatacaccgc t    101

<210> SEQ ID NO 176
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,43,46,49,64,67,70,76,82
<223> OTHER INFORMATION: /note="n is A, T, C, or G"

<400> SEQUENCE: 176
caagggtgcc ctgcccccaa taatccatrw nrcyrtnrcy rtnrtnrtnr karkarkark    60
artnrtnrtn rcyrtnrcyr wngaaacgcg cgcaataata caccgct                  107

<210> SEQ ID NO 177
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,46,49,64,67,73,76,82
<223> OTHER INFORMATION: /note="n is A, T, C, or G"

<400> SEQUENCE: 177
caagggtgcc ctgccccaa taatccatrw nrcyrtnrtn rcyrtnrtnr karkarkark    60
artnrtnrcy rtnrtnrcyr wngaaacgcg cgcaataata caccgct                  107

<210> SEQ ID NO 178
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,49,64,70,73,76,82
<223> OTHER INFORMATION: /note="n is A, T, C, or G"

<400> SEQUENCE: 178
caagggtgcc ctgccccaa taatccatrw nrcyrtnrtn rtnrcyrtnr karkarkark    60
artnrcyrtn rtnrtnrcyr wngaaacgcg cgcaataata caccgct                  107

<210> SEQ ID NO 179
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,46,67,70,73,76,82
<223> OTHER INFORMATION: /note="n is A, T, C, or G"

<400> SEQUENCE: 179
caagggtgcc ctgccccaa taatccatrw nrcyrtnrtn rtnrtnrcyr karkarkark    60
arcyrtnrtn rtnrtnrcyr wngaaacgcg cgcaataata caccgct                  107

<210> SEQ ID NO 180
<211> LENGTH: 107
<212> TYPE: DNA
<213> ORGANISM: Artificial Sequence
<220> FEATURE:

<223> OTHER INFORMATION: Synthetic
<220> FEATURE:
<221> NAME/KEY: variation
<222> LOCATION: 31,37,40,43,46,49,64,67,70,73,76,82
<223> OTHER INFORMATION: /note="n is A, T, C, or G"

<400> SEQUENCE: 180
caagggtgcc ctgcccccaa taatccatrw nrcyrtnrtn rtnrtnrtnr cyrkarkarc    60
yrtnrtnrtn rtnrtnrcyr wngaaacgcg cgcaataata caccgct    107

<210> SEQ ID NO 181
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: V_region
<222> LOCATION: 31,37,40,43,46,49,64,67,70,73,76,82
<223> OTHER INFORMATION: /note="n is A, T, C, or G"

<400> SEQUENCE: 181
caagggtgcc ctgcccccaa taatccatrw nrcyrtnrtn rtnrtnrtnr karkarcyrk    60
artnrtnrtn rtnrtnrcyr wngaaacgcg cgcaataata caccgct    107

<210> SEQ ID NO 182
<211> LENGTH: 107
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 31,37,40,43,46,49,64,67,70,73,76,82
<223> OTHER INFORMATION: /note="n is A, T, C, or G"

<400> SEQUENCE: 182
caagggtgcc ctgcccccaa taatccatrw nrcyrtnrtn rtnrtnrtnr karcyrkark    60
artnrtnrtn rtnrtnrcyr wngaaacgcg cgcaataata caccgct    107

<210> SEQ ID NO 183
<211> LENGTH: 75
<212> TYPE: DNA
<213> ORGANISM: Artificial Sequence
<220> FEATURE:
<223> OTHER INFORMATION: Synthetic

<400> SEQUENCE: 183
gtaacaaggg tgccctgccc ccaataatcr dardardacc mrdardaccm acgcgcgcaa    60
taatacaccg ctgtg    75

<210> SEQ ID NO 184
<211> LENGTH: 75
<212> TYPE: DNA
<213> ORGANISM: Artificial Sequence
<220> FEATURE:
<223> OTHER INFORMATION: Synthetic

<400> SEQUENCE: 184
gtaacaaggg tgccctgccc ccaataatcr dardaccmrd ardardaccm acgcgcgcaa    60
taatacaccg ctgtg    75

<210> SEQ ID NO 185
<211> LENGTH: 75

```
<212> TYPE: DNA
<213> ORGANISM: Artificial Sequence
<220> FEATURE:
<223> OTHER INFORMATION: Synthetic

<400> SEQUENCE: 185
gtaacaaggg tgccctgccc ccaataatcr daccmrdard ardardaccm acgcgcgcaa      60
taatacaccg ctgtg                                                      75

<210> SEQ ID NO 186
<211> LENGTH: 75
<212> TYPE: DNA
<213> ORGANISM: Artificial Sequence
<220> FEATURE:
<223> OTHER INFORMATION: Synthetic

<400> SEQUENCE: 186
gtaacaaggg tgccctgccc ccaataatcc cmrdardard ardardaccm acgcgcgcaa      60
taatacaccg ctgtg                                                      75

<210> SEQ ID NO 187
<211> LENGTH: 75
<212> TYPE: DNA
<213> ORGANISM: Artificial Sequence
<220> FEATURE:
<223> OTHER INFORMATION: Synthetic

<400> SEQUENCE: 187
gtaacaaggg tgccctgccc ccaataatcr dardaccmrd ardaccmrda acgcgcgcaa      60
taatacaccg ctgtg                                                      75

<210> SEQ ID NO 188
<211> LENGTH: 75
<212> TYPE: DNA
<213> ORGANISM: Artificial Sequence
<220> FEATURE:
<223> OTHER INFORMATION: Synthetic

<400> SEQUENCE: 188
gtaacaaggg tgccctgccc ccaataatcr daccmrdard ardaccmrda acgcgcgcaa      60
taatacaccg ctgtg                                                      75

<210> SEQ ID NO 189
<211> LENGTH: 75
<212> TYPE: DNA
<213> ORGANISM: Artificial Sequence
<220> FEATURE:
<223> OTHER INFORMATION: Synthetic

<400> SEQUENCE: 189
gtaacaaggg tgccctgccc ccaataatcc cmrdardard ardaccmrda acgcgcgcaa      60
taatacaccg ctgtg                                                      75

<210> SEQ ID NO 190
<211> LENGTH: 75
<212> TYPE: DNA
<213> ORGANISM: Artificial Sequence
<220> FEATURE:
<223> OTHER INFORMATION: Synthetic

<400> SEQUENCE: 190
gtaacaaggg tgccctgccc ccaataatcr daccmrdard accmrdarda acgcgcgcaa      60
```

```
taatacaccg ctgtg                                                      75

<210> SEQ ID NO 191
<211> LENGTH: 75
<212> TYPE: DNA
<213> ORGANISM: Artificial Sequence
<220> FEATURE:
<223> OTHER INFORMATION: Synthetic

<400> SEQUENCE: 191
gtaacaaggg tgccctgccc ccaataatcc cmrdardard accmrdarda acgcgcgcaa     60
taatacaccg ctgtg                                                      75

<210> SEQ ID NO 192
<211> LENGTH: 75
<212> TYPE: DNA
<213> ORGANISM: Artificial Sequence
<220> FEATURE:
<223> OTHER INFORMATION: Synthetic

<400> SEQUENCE: 192
gtaacaaggg tgccctgccc ccaataatcc cmrdardacc mrdardarda acgcgcgcaa     60
taatacaccg ctgtg                                                      75

<210> SEQ ID NO 193
<211> LENGTH: 72
<212> TYPE: DNA
<213> ORGANISM: Artificial Sequence
<220> FEATURE:
<223> OTHER INFORMATION: Synthetic

<400> SEQUENCE: 193
gtaacaaggg tgccctgccc ccaataatcr dardaccmrd ardaccmacg cgcgcaataa     60
tacaccgctg tg                                                         72

<210> SEQ ID NO 194
<211> LENGTH: 72
<212> TYPE: DNA
<213> ORGANISM: Artificial Sequence
<220> FEATURE:
<223> OTHER INFORMATION: Synthetic

<400> SEQUENCE: 194
gtaacaaggg tgccctgccc ccaataatcr daccmrdard ardaccmacg cgcgcaataa     60
tacaccgctg tg                                                         72

<210> SEQ ID NO 195
<211> LENGTH: 72
<212> TYPE: DNA
<213> ORGANISM: Artificial Sequence
<220> FEATURE:
<223> OTHER INFORMATION: Synthetic

<400> SEQUENCE: 195
gtaacaaggg tgccctgccc ccaataatcc cmrdardard ardaccmacg cgcgcaataa     60
tacaccgctg tg                                                         72

<210> SEQ ID NO 196
<211> LENGTH: 72
<212> TYPE: DNA
<213> ORGANISM: Artificial Sequence
<220> FEATURE:
<223> OTHER INFORMATION: Synthetic
```

<400> SEQUENCE: 196
gtaacaaggg tgccctgccc ccaataatcr daccmrdard accmrdaacg cgcgcaataa    60
tacaccgctg tg    72

<210> SEQ ID NO 197
<211> LENGTH: 72
<212> TYPE: DNA
<213> ORGANISM: Artificial Sequence
<220> FEATURE:
<223> OTHER INFORMATION: Synthetic

<400> SEQUENCE: 197
gtaacaaggg tgccctgccc ccaataatcc cmrdardard accmrdaacg cgcgcaataa    60
tacaccgctg tg    72

<210> SEQ ID NO 198
<211> LENGTH: 72
<212> TYPE: DNA
<213> ORGANISM: Artificial Sequence
<220> FEATURE:
<223> OTHER INFORMATION: Synthetic

<400> SEQUENCE: 198
gtaacaaggg tgccctgccc ccaataatcc cmrdardacc mrdardaacg cgcgcaataa    60
tacaccgctg tg    72

<210> SEQ ID NO 199
<211> LENGTH: 69
<212> TYPE: DNA
<213> ORGANISM: Artificial Sequence
<220> FEATURE:
<223> OTHER INFORMATION: Synthetic

<400> SEQUENCE: 199
gtaacaaggg tgccctgccc ccaataatcr daccmrdard accmacgcgc gcaataatac    60
accgctgtg    69

<210> SEQ ID NO 200
<211> LENGTH: 69
<212> TYPE: DNA
<213> ORGANISM: Artificial Sequence
<220> FEATURE:
<223> OTHER INFORMATION: Synthetic

<400> SEQUENCE: 200
gtaacaaggg tgccctgccc ccaataatcc cmrdardard accmacgcgc gcaataatac    60
accgctgtg    69

<210> SEQ ID NO 201
<211> LENGTH: 69
<212> TYPE: DNA
<213> ORGANISM: Artificial Sequence
<220> FEATURE:
<223> OTHER INFORMATION: Synthetic

<400> SEQUENCE: 201
gtaacaaggg tgccctgccc ccaataatcc cmrdardacc mrdaacgcgc gcaataatac    60
accgctgtg    69

<210> SEQ ID NO 202

```
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,48
<223> OTHER INFORMATION: /note="n is A, T, C, or G"

<400> SEQUENCE: 202
cacggtaaca agggtgccct gcccccaata rtnrdaccmr daccmccncg cgcaataata    60
caccgctgtg tcttccgc                                                  78

<210> SEQ ID NO 203
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,48
<223> OTHER INFORMATION: /note="n is A, T, C, or G"

<400> SEQUENCE: 203
cacggtaaca agggtgccct gcccccaata rtnccmrdar daccmccncg cgcaataata    60
caccgctgtg tcttccgc                                                  78

<210> SEQ ID NO 204
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,48
<223> OTHER INFORMATION: /note="n is A, T, C, or G"

<400> SEQUENCE: 204
cacggtaaca agggtgccct gcccccaata rtnccmrdac cmrdaccncg cgcaataata    60
caccgctgtg tcttccgc                                                  78

<210> SEQ ID NO 205
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,45
<223> OTHER INFORMATION: /note="n is A, T, C, or G"

<400> SEQUENCE: 205
cacggtaaca agggtgccct gcccccaata rtnrdardac cmccncgcgc aataatacac    60
cgctgtgtct tccgc                                                     75

<210> SEQ ID NO 206
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: variation
```

<222> LOCATION: 33,45
<223> OTHER INFORMATION: /note="n is A, T, C, or G"

<400> SEQUENCE: 206
cacggtaaca agggtgccct gccccaata rtnrdaccmr daccncgcgc aataatacac    60
cgctgtgtct tccgc    75

<210> SEQ ID NO 207
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,45
<223> OTHER INFORMATION: /note="n is A, T, C, or G"

<400> SEQUENCE: 207
cacggtaaca agggtgccct gccccaata rtnccmrdar daccncgcgc aataatacac    60
cgctgtgtct tccgc    75

<210> SEQ ID NO 208
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,42
<223> OTHER INFORMATION: /note="n is A, T, C, or G"

<400> SEQUENCE: 208
cacggtaaca agggtgccct gccccaata rtnrdaccmc cncgcgcaat aatacaccgc    60
tgtgtcttcc gc    72

<210> SEQ ID NO 209
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,42
<223> OTHER INFORMATION: /note="n is A, T, C, or G"

<400> SEQUENCE: 209
cacggtaaca agggtgccct gccccaata rtnccmrdac cncgcgcaat aatacaccgc    60
tgtgtcttcc gc    72

<210> SEQ ID NO 210
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,39
<223> OTHER INFORMATION: /note="n is A, T, C, or G"

<400> SEQUENCE: 210
cacggtaaca agggtgccct gccccaata rtnccmccnc gcgcaataat acaccgctgt    60
gtcttccgc 69

<210> SEQ ID NO 211
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: variation
<222> LOCATION: 33,39
<223> OTHER INFORMATION: /note="n is A, T, C, or G"

<400> SEQUENCE: 211
cacggtaaca agggtgccct gcccccaata rtnrdaccnc gcgcaataat acaccgctgt 60
gtcttccgc 69

<210> SEQ ID NO 212
<211> LENGTH: 47
<212> TYPE: DNA
<213> ORGANISM: Artificial Sequence
<220> FEATURE:
<223> OTHER INFORMATION: Synthetic

<400> SEQUENCE: 212
gggcccagcc ggccatggcc gatattcaaa tgacccagag cccgagc 47

<210> SEQ ID NO 213
<211> LENGTH: 51
<212> TYPE: DNA
<213> ORGANISM: Artificial Sequence
<220> FEATURE:
<223> OTHER INFORMATION: Synthetic

<400> SEQUENCE: 213
ggaagatcta gaggaaccac cgcgtttgat ttccactttg gtgccttgac c 51

<210> SEQ ID NO 214
<211> LENGTH: 77
<212> TYPE: DNA
<213> ORGANISM: Artificial Sequence
<220> FEATURE:
<223> OTHER INFORMATION: Synthetic

<400> SEQUENCE: 214
ggtggttcct ctagatcttc ctcctctggt ggcggtggct cgggcggtgg tggggaagtg 60
cagctggtgg aatcggg 77

<210> SEQ ID NO 215
<211> LENGTH: 26
<212> TYPE: DNA
<213> ORGANISM: Artificial Sequence
<220> FEATURE:
<223> OTHER INFORMATION: Synthetic

<400> SEQUENCE: 215
cctgcctgcg gccgctgacg ccgagc 26

<210> SEQ ID NO 216
<211> LENGTH: 48
<212> TYPE: DNA
<213> ORGANISM: Artificial Sequence
<220> FEATURE:
<223> OTHER INFORMATION: Synthetic

<400> SEQUENCE: 216
gaggaggagg aggaggaggc ggggcccagc cggccatggc cgatattc         48

<210> SEQ ID NO 217
<211> LENGTH: 40
<212> TYPE: DNA
<213> ORGANISM: Artificial Sequence
<220> FEATURE:
<223> OTHER INFORMATION: Synthetic

<400> SEQUENCE: 217
gaggaggagg aggaggagcc tgcctgcggc cgctgacgcc                  40

<210> SEQ ID NO 218
<211> LENGTH: 59
<212> TYPE: DNA
<213> ORGANISM: Artificial Sequence
<220> FEATURE:
<223> OTHER INFORMATION: Synthetic

<400> SEQUENCE: 218
caggtgcacg atgtgatggt accgatattc aaatgaccca gagcccgagc agcctgagc    59

<210> SEQ ID NO 219
<211> LENGTH: 36
<212> TYPE: DNA
<213> ORGANISM: Artificial Sequence
<220> FEATURE:
<223> OTHER INFORMATION: Synthetic

<400> SEQUENCE: 219
tgcagccacc gtacgtttga tttccacctt ggtgcc                      36

<210> SEQ ID NO 220
<211> LENGTH: 36
<212> TYPE: DNA
<213> ORGANISM: Artificial Sequence
<220> FEATURE:
<223> OTHER INFORMATION: Synthetic

<400> SEQUENCE: 220
cgtgtcgcat ctgaagtgca gctggtggaa tcggga                      36

<210> SEQ ID NO 221
<211> LENGTH: 48
<212> TYPE: DNA
<213> ORGANISM: Artificial Sequence
<220> FEATURE:
<223> OTHER INFORMATION: Synthetic

<400> SEQUENCE: 221
gaccgatggg cccttggtgc tagccgagct cacggtaaca agggtgcc         48

<210> SEQ ID NO 222
<211> LENGTH: 39
<212> TYPE: DNA
<213> ORGANISM: Artificial Sequence
<220> FEATURE:
<223> OTHER INFORMATION: Synthetic

<400> SEQUENCE: 222
aaggtggaaa tcaaacgtac ggtggctgca ccatctgtc                   39

<210> SEQ ID NO 223
<211> LENGTH: 33
<212> TYPE: DNA

<213> ORGANISM: Artificial Sequence
<220> FEATURE:
<223> OTHER INFORMATION: Synthetic

<400> SEQUENCE: 223
ctgcacttca gatgcgacac gcgtagcaac agc                                    33

<210> SEQ ID NO 224
<211> LENGTH: 475
<212> TYPE: PRT
<213> ORGANISM: Artificial Sequence
<220> FEATURE:
<223> OTHER INFORMATION: Synthetic

<400> SEQUENCE: 224

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
```

```
                   325                 330                 335
Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Leu His His His His His Ser Leu His His His His
        370                 375                 380

His Ser Ser Asn Asn Asn Asn Asn Asn Asn Asn Leu Gly Ile
385                 390                 395                 400

Glu Gly Arg Ile Ser Glu Phe Arg Cys Trp Gly Glu Ser Ser Glu Asp
                405                 410                 415

Cys Gln Ser Leu Thr Arg Thr Val Cys Ala Gly Gly Cys Ala Arg Cys
                420                 425                 430

Lys Gly Pro Leu Pro Thr Asp Cys Cys His Glu Gln Cys Ala Ala Gly
                435                 440                 445

Cys Thr Gly Pro Lys His Ser Asp Cys Leu Ala Cys Leu His Phe Asn
450                 455                 460

His Ser Gly Leu Glu His His His His His
465                 470                 475

<210> SEQ ID NO 225
<211> LENGTH: 670
<212> TYPE: PRT
<213> ORGANISM: Artificial Sequence
<220> FEATURE:
<223> OTHER INFORMATION: Synthetic

<400> SEQUENCE: 225

Asp Ala Ala Gln Pro Ala Thr Gln Val Cys Thr Gly Thr Asp Met Lys
1               5                   10                  15

Leu Arg Leu Pro Ala Ser Pro Glu Thr His Leu Asp Met Leu Arg His
                20                  25                  30

Leu Tyr Gln Gly Cys Gln Val Val Gln Gly Asn Leu Glu Leu Thr Tyr
            35                  40                  45

Leu Pro Thr Asn Ala Ser Leu Ser Phe Leu Gln Asp Ile Gln Glu Val
        50                  55                  60

Gln Gly Tyr Val Leu Ile Ala His Asn Gln Val Arg Gln Val Pro Leu
65                  70                  75                  80

Gln Arg Leu Arg Ile Val Arg Gly Thr Gln Leu Phe Glu Asp Asn Tyr
                85                  90                  95

Ala Leu Ala Val Leu Asp Asn Gly Asp Pro Leu Asn Asn Thr Thr Pro
            100                 105                 110

Val Thr Gly Ala Ser Pro Gly Gly Leu Arg Glu Leu Gln Leu Arg Ser
        115                 120                 125

Leu Thr Glu Ile Leu Lys Gly Gly Val Leu Ile Gln Arg Asn Pro Gln
130                 135                 140

Leu Cys Tyr Gln Asp Thr Ile Leu Trp Lys Asp Ile Phe His Lys Asn
145                 150                 155                 160

Asn Gln Leu Ala Leu Thr Leu Ile Asp Thr Asn Arg Ser Arg Ala Cys
                165                 170                 175

His Pro Cys Ser Pro Met Cys Lys Gly Ser Arg Cys Trp Gly Glu Ser
            180                 185                 190

Ser Glu Asp Cys Gln Ser Leu Thr Arg Thr Val Cys Ala Gly Gly Cys
        195                 200                 205

Ala Arg Cys Lys Gly Pro Leu Pro Thr Asp Cys Cys His Glu Gln Cys
```

```
                210                 215                 220
Ala Ala Gly Cys Thr Gly Pro Lys His Ser Asp Cys Leu Ala Cys Leu
225                 230                 235                 240

His Phe Asn His Ser Gly Ile Cys Glu Leu His Cys Pro Ala Leu Val
                245                 250                 255

Thr Tyr Asn Thr Asp Thr Phe Glu Ser Met Pro Asn Pro Glu Gly Arg
                260                 265                 270

Tyr Thr Phe Gly Ala Ser Cys Val Thr Ala Cys Pro Tyr Asn Tyr Leu
                275                 280                 285

Ser Thr Asp Val Gly Ser Cys Thr Leu Val Cys Pro Leu His Asn Gln
                290                 295                 300

Glu Val Thr Ala Glu Asp Gly Thr Gln Arg Cys Glu Lys Cys Ser Lys
305                 310                 315                 320

Pro Cys Ala Arg Val Cys Tyr Gly Leu Gly Met Glu His Leu Arg Glu
                325                 330                 335

Val Arg Ala Val Thr Ser Ala Asn Ile Gln Glu Phe Ala Gly Cys Lys
                340                 345                 350

Lys Ile Phe Gly Ser Leu Ala Phe Leu Pro Glu Ser Phe Asp Gly Asp
                355                 360                 365

Pro Ala Ser Asn Thr Ala Pro Leu Gln Pro Glu Gln Leu Gln Val Phe
                370                 375                 380

Glu Thr Leu Glu Glu Ile Thr Gly Tyr Leu Tyr Ile Ser Ala Trp Pro
385                 390                 395                 400

Asp Ser Leu Pro Asp Leu Ser Val Phe Gln Asn Leu Gln Val Ile Arg
                405                 410                 415

Gly Arg Ile Leu His Asn Gly Ala Tyr Ser Leu Thr Leu Gln Gly Leu
                420                 425                 430

Gly Ile Ser Trp Leu Gly Leu Arg Ser Leu Arg Glu Leu Gly Ser Gly
                435                 440                 445

Leu Ala Leu Ile His His Asn Thr His Leu Cys Phe Val His Thr Val
                450                 455                 460

Pro Trp Asp Gln Leu Phe Arg Asn Pro His Gln Ala Leu Leu His Thr
465                 470                 475                 480

Ala Asn Arg Pro Glu Asp Glu Cys Val Gly Glu Gly Leu Ala Cys His
                485                 490                 495

Gln Leu Cys Ala Arg Gly His Cys Trp Gly Pro Gly Pro Thr Gln Cys
                500                 505                 510

Val Asn Cys Ser Gln Phe Leu Arg Gly Gln Glu Cys Val Glu Glu Cys
                515                 520                 525

Arg Val Leu Gln Gly Leu Pro Arg Glu Tyr Val Asn Ala Arg His Cys
530                 535                 540

Leu Pro Cys His Pro Glu Cys Gln Pro Gln Asn Gly Ser Val Thr Cys
545                 550                 555                 560

Phe Gly Pro Glu Ala Asp Gln Cys Val Ala Cys Ala His Tyr Lys Asp
                565                 570                 575

Pro Pro Phe Cys Val Ala Arg Cys Pro Ser Gly Val Lys Pro Asp Leu
                580                 585                 590

Ser Tyr Met Pro Ile Trp Lys Phe Pro Asp Glu Glu Gly Ala Cys Gln
                595                 600                 605

Pro Cys Pro Ile Asn Cys Thr His Ser Cys Val Asp Leu Asp Asp Lys
                610                 615                 620

Gly Cys Pro Ala Glu Gln Asp Ile Glu Asn Leu Tyr Phe Gln Gly Ala
625                 630                 635                 640
```

```
Met Ala Ala Ala Ala Arg Gly Gly Pro Glu Gln Lys Leu Ile Ser Glu
                645                 650                 655

Glu Asp Leu Asn Ser Ala Val Asp His His His His His His
        660                 665                 670
```

<210> SEQ ID NO 226
<211> LENGTH: 47
<212> TYPE: DNA
<213> ORGANISM: Artificial Sequence
<220> FEATURE:
<223> OTHER INFORMATION: Synthetic

<400> SEQUENCE: 226
gaggaggagg aggaggaggc ggggcccagc cggccatggc cgagctc           47

<210> SEQ ID NO 227
<211> LENGTH: 40
<212> TYPE: DNA
<213> ORGANISM: Artificial Sequence
<220> FEATURE:
<223> OTHER INFORMATION: Synthetic

<400> SEQUENCE: 227
gaggaggagg aggaggagcc tgcctgcggc cgcactagtg                    40

<210> SEQ ID NO 228
<211> LENGTH: 17
<212> TYPE: DNA
<213> ORGANISM: Artificial Sequence
<220> FEATURE:
<223> OTHER INFORMATION: Synthetic

<400> SEQUENCE: 228
gcccagccgg ccatggc                                             17

<210> SEQ ID NO 229
<211> LENGTH: 18
<212> TYPE: DNA
<213> ORGANISM: Artificial Sequence
<220> FEATURE:
<223> OTHER INFORMATION: Synthetic

<400> SEQUENCE: 229
gccaccgcca ccagagga                                            18

<210> SEQ ID NO 230
<211> LENGTH: 22
<212> TYPE: DNA
<213> ORGANISM: Artificial Sequence
<220> FEATURE:
<223> OTHER INFORMATION: Synthetic

<400> SEQUENCE: 230
gggtggttcc tctagatctt cc                                       22

<210> SEQ ID NO 231
<211> LENGTH: 19
<212> TYPE: DNA
<213> ORGANISM: Artificial Sequence
<220> FEATURE:
<223> OTHER INFORMATION: Synthetic

<400> SEQUENCE: 231
cacctgcggc cgcactagt                                           19

<210> SEQ ID NO 232
<211> LENGTH: 792
<212> TYPE: DNA
<213> ORGANISM: Artificial Sequence
<220> FEATURE:
<223> OTHER INFORMATION: Synthetic

<400> SEQUENCE: 232

```
atggccgagc tcggcattga gctgacccaa tctcaaaaat tcatgtccac atcagtagga      60
gacagggtca gcatcacctg caaggccagt cagaatgtgg gtactgctgt agcctggtat     120
caacagaaac caggacaatc tcctaaacta ctgatttact cggcatccaa tcggtacact     180
ggagtccctg atcgcttcac aggcagtgga tctgggacag atttcactct caccatcagc     240
aatatgcagt ctgaagacct ggcagattat ttctgccagc aatatagcag ctatcctcta     300
gcgttcggag ggggaccaa actggaaata aaatcctctg gtggcggtgg ctcgggcggt      360
ggtggggtg gttcctctag atcttccctc gaggtgcagc tggtggagtc tggggctgag      420
cttgtgaggc caggggcctt agtcaagttg tcctgcaaag cttctggctt caacattaaa     480
gactactta tgtactgggt gaagcagagg cctgagcagg gcctggagtg ggttggatgg     540
attgatcctg agaatggtaa tactatatat gacccgaagt tccagggcaa ggccagtata    600
acagcagaca catcctccaa cacagcctac ctgcagctca gcagcctgac atctgaggac    660
actgccgtct attactgtac tagagggtac tacggtagta gagtgcttgc tatggactat    720
tggggtcaag gaacctcagt caccgtctcc tcagccaaaa caacaccccc atctgtcact    780
agtgcggccg ca                                                        792
```

<210> SEQ ID NO 233
<211> LENGTH: 264
<212> TYPE: PRT
<213> ORGANISM: Artificial Sequence
<220> FEATURE:
<223> OTHER INFORMATION: Synthetic

<400> SEQUENCE: 233

```
Met Ala Glu Leu Gly Ile Glu Leu Thr Gln Ser Gln Lys Phe Met Ser
1               5                   10                  15

Thr Ser Val Gly Asp Arg Val Ser Ile Thr Cys Lys Ala Ser Gln Asn
            20                  25                  30

Val Gly Thr Ala Val Ala Trp Tyr Gln Gln Lys Pro Gly Gln Ser Pro
        35                  40                  45

Lys Leu Leu Ile Tyr Ser Ala Ser Asn Arg Tyr Thr Gly Val Pro Asp
    50                  55                  60

Arg Phe Thr Gly Ser Gly Ser Gly Thr Asp Phe Thr Leu Thr Ile Ser
65                  70                  75                  80

Asn Met Gln Ser Glu Asp Leu Ala Asp Tyr Phe Cys Gln Gln Tyr Ser
                85                  90                  95

Ser Tyr Pro Leu Ala Phe Gly Gly Gly Thr Lys Leu Glu Ile Lys Ser
            100                 105                 110

Ser Gly Gly Gly Gly Ser Gly Gly Gly Gly Ser Ser Arg Ser
        115                 120                 125

Ser Leu Glu Val Gln Leu Val Glu Ser Gly Ala Glu Leu Val Arg Pro
    130                 135                 140

Gly Ala Leu Val Lys Leu Ser Cys Lys Ala Ser Gly Phe Asn Ile Lys
145                 150                 155                 160

Asp Tyr Phe Met Tyr Trp Val Lys Gln Arg Pro Glu Gln Gly Leu Glu
```

```
              165                 170                 175
Trp Val Gly Trp Ile Asp Pro Glu Asn Gly Asn Thr Ile Tyr Asp Pro
            180                 185                 190

Lys Phe Gln Gly Lys Ala Ser Ile Thr Ala Asp Thr Ser Ser Asn Thr
        195                 200                 205

Ala Tyr Leu Gln Leu Ser Ser Leu Thr Ser Glu Asp Thr Ala Val Tyr
    210                 215                 220

Tyr Cys Thr Arg Gly Tyr Tyr Gly Ser Arg Val Leu Ala Met Asp Tyr
225                 230                 235                 240

Trp Gly Gln Gly Thr Ser Val Thr Val Ser Ser Ala Lys Thr Thr Pro
                245                 250                 255

Pro Ser Val Thr Ser Ala Ala Ala
            260

<210> SEQ ID NO 234
<211> LENGTH: 747
<212> TYPE: DNA
<213> ORGANISM: Artificial Sequence
<220> FEATURE:
<223> OTHER INFORMATION: Synthetic

<400> SEQUENCE: 234
gatattcaaa tgacccagag cccgagcagc ctgagcgcga gcgtgggaga tcgcgtgacc      60
attacctgca aggccagtca gaatgtgggt actgcggtcg catggtatca gcagaaacca     120
ggcaaagcgc cgaaacttct gatatactct gcatccaatc ggtacactgg cgtgccgtcg     180 cgttttcgg gcagtggcag cggcacggac tttacccctga cgatatcttc cttacaaccg     240 gaggatttg cgacctacta ctgtcaacag tatagcagct atcctctagc gttcggtcaa     300
ggcaccaaag tggaaatcaa acgcggaggg ggaggtagca tcgagggccg tagcggaggt     360
ggcgggagcg aagtgcagct ggtggaatcg ggaggcggtc tggtgcaacc tggcggcagc     420
cttcgtctga gctgtaaagc ttctggcttc aacattaaag actactttat gtactgggtg     480
cgtcaagctc ccggcaaggg gctggagtgg gtcgatggga ttgatcctga aatggtaat     540 actatatatg acccgaagtt ccagggtcgc tttacgatta gtgcggacac cagcaaaaat     600
accgcgtacc tgcagatgaa tagcctgcgt gcggaagaca cagcggtgta ttattgcact     660
agagggtact acggtagtag agtgcttgcg atggattatt ggggcaggg cacccttgtt     720 accgtgagct cggcgtcagc ggccgca                                        747

<210> SEQ ID NO 235
<211> LENGTH: 249
<212> TYPE: PRT
<213> ORGANISM: Artificial Sequence
<220> FEATURE:
<223> OTHER INFORMATION: Synthetic

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Ser Ser Tyr Pro Leu
                    85                  90                  95

Ala Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Lys Ala Ser Gly Phe Asn Ile Lys Asp Tyr Phe Met Tyr Trp Val
145                 150                 155                 160

Arg Gln Ala Pro Gly Lys Gly Leu Glu Trp Val Gly Trp Ile Asp Pro
                165                 170                 175

Glu Asn Gly Asn Thr Ile Tyr Asp Pro Lys Phe Gln Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Thr Arg Gly Tyr Tyr
    210                 215                 220

Gly Ser Arg Val Leu Ala Met Asp Tyr Trp Gly Gln Gly Thr Leu Val
225                 230                 235                 240

Thr Val Ser Ser Ala Ser Ala Ala Ala
            245

<210> SEQ ID NO 236
<211> LENGTH: 783
<212> TYPE: DNA
<213> ORGANISM: Artificial Sequence
<220> FEATURE:
<223> OTHER INFORMATION: Synthetic

<400> SEQUENCE: 236
atggccgagc tcgatattca gatgatacag tctcaaaaat tcatgtccac atcagtagga      60
gacagggtca gcgtcacctg caaggccagt cagaatgtgg gtactaatgt agcctggtat     120
caacagaaac cagggcaatc tcctaaagca ctgattcact cggcatccta ccggtacagt     180
ggagtccctg atcgcttcac aggcagtgga tccgggacag atttcactct caccatcagc     240
aatgtgcagt ctgaagactt ggcagagtat ttctgtcagc aatataacag ctatcctctc     300
acgttcggtg ctgggaccaa actggaaatc aaatcctctg gtggcggtgg ctcgggcggt     360 ggtggggtg gttcctctag atcttccctc gaggtccagc tgcaacagtc tggaactgaa     420
ctggcgaggc ccggggcttc agtgaagttg tcctgtaagg cttctggcta ccttcatt      480 gactactata taacctgggt gaaacagagg actggacagg ccttgagtg gattggagag     540 atttatcctg gaggtggtaa tccttactat aatgataact caagggcaa ggcctcgctg      600 actgcagaca atcctccaa cacagtctac atgcagctca gcagcctgac atctgaggac      660
tctgcagtct atttctgtgc aagatcctat aagtacgacg tttctgttta ctggggccaa     720
gggactctgg tcactgtctc tgcagccaaa acaacacccc catctgtcac tagtgcggcc     780
gca                                                                   783

<210> SEQ ID NO 237
<211> LENGTH: 276
<212> TYPE: PRT
<213> ORGANISM: Artificial Sequence
<220> FEATURE:
```

<223> OTHER INFORMATION: Synthetic

<400> SEQUENCE: 237

Met Ala Glu Leu Asp Ile Gln Met Ile Gln Ser Gln Lys Phe Met Ser
1               5                   10                  15

Thr Ser Val Gly Asp Arg Val Ser Val Thr Cys Lys Ala Ser Gln Asn
            20                  25                  30

Val Gly Thr Asn Val Ala Trp Tyr Gln Gln Lys Pro Gly Gln Ser Pro
        35                  40                  45

Lys Ala Leu Ile His Ser Ala Ser Tyr Arg Tyr Ser Gly Val Pro Asp
    50                  55                  60

Arg Phe Thr Gly Ser Gly Ser Gly Thr Asp Phe Thr Leu Thr Ile Ser
65                  70                  75                  80

Asn Val Gln Ser Glu Asp Leu Ala Glu Tyr Phe Cys Gln Gln Tyr Asn
                85                  90                  95

Ser Tyr Pro Leu Thr Phe Gly Ala Gly Thr Lys Leu Glu Ile Lys Ser
            100                 105                 110

Ser Gly Gly Gly Gly Ser Gly Gly Gly Gly Gly Ser Ser Arg Ser
        115                 120                 125

Ser Leu Glu Val Gln Leu Gln Gln Ser Gly Thr Glu Leu Ala Arg Pro
130                 135                 140

Gly Ala Ser Val Lys Leu Ser Cys Lys Ala Ser Gly Tyr Thr Phe Ile
145                 150                 155                 160

Asp Tyr Tyr Ile Thr Trp Val Lys Gln Arg Thr Gly Gln Gly Leu Glu
                165                 170                 175

Trp Ile Gly Glu Ile Tyr Pro Gly Gly Gly Asn Pro Tyr Tyr Asn Asp
            180                 185                 190

Asn Phe Lys Gly Lys Ala Ser Leu Thr Ala Asp Lys Ser Ser Asn Thr
        195                 200                 205

Val Tyr Met Gln Leu Ser Ser Leu Thr Ser Glu Asp Ser Ala Val Tyr
    210                 215                 220

Phe Cys Ala Arg Ser Tyr Lys Tyr Asp Val Ser Val Tyr Trp Gly Gln
225                 230                 235                 240

Gly Thr Leu Val Thr Val Ser Ala Ala Lys Thr Thr Pro Pro Ser Val
                245                 250                 255

Thr Ser Ala Ala Ala Gly Ala Pro Val Pro Tyr Pro Asp Pro Leu Glu
            260                 265                 270

Pro Arg Ala Ala
        275

<210> SEQ ID NO 238
<211> LENGTH: 747
<212> TYPE: DNA
<213> ORGANISM: Artificial Sequence
<220> FEATURE:
<223> OTHER INFORMATION: Synthetic

<400> SEQUENCE: 238
atggccgata ttcaaatgac ccagagcccg agcagcctga gcgcgagcgt gggagatcgc        60
gtgaccatta cctgccgtgc gagccaggat gttaatagta acgtcgcatg gtatcagcag       120
aaaccaggca aagcgccgaa acttctgata tactggacaa ccgggctgta tagcggcgtg       180
ccgtcgcgtt ttcgggcag tggcagcggc acggacttta ccctgacgat atcttcctta       240
caaccggagg attttgcgac ctactactgt caacagtacc ttagcgggcc gataaccttc       300
ggtcaaggca ccaaagtgga aatcaaacgc ggtggttcct ctagatctcc ctccggctcg       360

| | |
|---|---|
| ggcggtggtg gggaagtgca gctggtggaa tcgggaggcg gtctggtgca acctggcggc | 420 |
| agccttcgtc tgagctgtgc ggcgagcggg ttcaccatta gtaactgggg gattcattgg | 480 |
| gtgcgtcaag ctcccggcaa ggggctggag tgggtcgcgg ggatttggcc ctatgggggt | 540 |
| tacacatttt atgccgacag cgtgaaaggt cgctttacga ttagtgcgga caccagcaaa | 600 |
| ataccgcgt acctgcagat gaatagcctg cgtgcggaag acacagcggt gtattattgc | 660 |
| gcgcgtttca attatctcaa cctcgggggg atggattatt ggggcaggg caccttgtt | 720 |
| accgtgagct cggcgtcagc ggccgca | 747 |

<210> SEQ ID NO 239
<211> LENGTH: 753
<212> TYPE: DNA
<213> ORGANISM: Artificial Sequence
<220> FEATURE:
<223> OTHER INFORMATION: Synthetic

<400> SEQUENCE: 239

| | |
|---|---|
| atggccgata ttcaaatgac ccagagcccg agcagcctga gcgcgagcgt gggagatcgc | 60 |
| gtgaccatta cctgccgtgc gagccaggat gttagcagtg cgtcgcatg gtatcagcag | 120 |
| aaaccaggca agcgccgaa acttctgata tccgggccta ctgggctgta tagcggcgtg | 180 |
| ccgtcgcgtt tttcgggcag tggcagcggc acggacttta ccctgacgat atcttcctta | 240 |
| caaccggagg attttgcgac ctactactgt caacagtatt atgattggcc gttgaccttc | 300 |
| ggtcaaggca ccaaagtcaa acgcggtggt tcctctagat cttcctcctc tggtggcggt | 360 |
| ggctcgggcg gtggtgggga agtgcagctg gtggaatcgg gaggcggtct ggtgcaacct | 420 |
| ggcggcagcc ttcgtctgag ctgtgcggcg agcgggttca ccattagcaa ttggggggatt | 480 |
| cattgggtgc gtcaagctcc cggcaagggg ctggagtggg tcgcggggat tgggccctac | 540 |
| ggggggttata catcttatgc cgacagcgtg aaaggtcgct ttacgattag tgcggacacc | 600 |
| agcaaaaata ccgcgtacct gcagatgaat agcctgcgtg cggaagacac agcggtgtat | 660 |
| tattgcgcgc gtttcgggtt ttattttgac gggatcatgg attattgggg cagggcacc | 720 |
| cttgttaccg tgagctcggc gtcagcggcc gca | 753 |

<210> SEQ ID NO 240
<211> LENGTH: 735
<212> TYPE: DNA
<213> ORGANISM: Artificial Sequence
<220> FEATURE:
<223> OTHER INFORMATION: Synthetic

<400> SEQUENCE: 240

| | |
|---|---|
| atggccgata ttcaaatgac ccagagcccg agcagcctga gcgcgagcgt gggagatcgc | 60 |
| gtgatcatta cctgccgtgc gagccaggat gtttctgggt atgtcgcatg gtatcagcag | 120 |
| aaaccaggca agcgccgaa acttctgata tactctagcg gcgtgccgtc gcgttttcg | 180 |
| ggcagtggca gcggcacgga ctttaccctg acgatatctt ccttacaacc ggaggatttt | 240 |
| gcgacctact actgtcaaca gtactataat tggccggtaa ccttcggtca aggcaccaaa | 300 |
| gtggaaatca aacgcggagg gggaggtagc atcgagggcc gtagcggagg tggcgggagc | 360 |
| gaagtgcagc tggtggaatc gggaggcggt ctggtgcaac tggcggcag ccttcgtctg | 420 |
| agctgtgcgg cgagcgggtc caccattggc aactccggga ttcattgggt gcgtcaagct | 480 |
| cccggcaagg ggctggagtg gtcgcgtat attgggccct acggggggtta cacatcctat | 540 |

```
gccgacagcg tgaaaggtcg ctttacgatt agtgcggaca ccagcaaaaa taccgcgtac    600
ctgcagatga atagcctgcg tgcggaagac acagcggtgt attattgcgc gcgtttcgat    660
gattaccatt gggatgggat ggattattgg gggcagggca cccttgttac cgtgagctcg    720
gcgtcagcgg ccgca                                                      735
```

<210> SEQ ID NO 241
<211> LENGTH: 248
<212> TYPE: PRT
<213> ORGANISM: Artificial Sequence
<220> FEATURE:
<223> OTHER INFORMATION: Synthetic

<400> SEQUENCE: 241

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Asn
            20                  25                  30

Val Ala Trp Tyr Gln Gln Lys Pro Gly Lys Ala Pro Lys Leu Leu Ile
        35                  40                  45

Tyr Gly Ala Arg Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Gly Gly Gly Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Gly Gly Trp Ile His Trp Val
145                 150                 155                 160

Arg Gln Ala Pro Gly Lys Gly Leu Glu Trp Val Ala Gly Ile Trp Pro
                165                 170                 175

Ser Gly Gly Ser Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Phe
    210                 215                 220

Gly Phe Gly Asp Leu Met Asp Tyr Trp Gly Gln Gly Thr Leu Val Thr
225                 230                 235                 240

Val Ser Ser Ala Ser Ala Ala Ala
                245
```

<210> SEQ ID NO 242
<211> LENGTH: 248
<212> TYPE: PRT
<213> ORGANISM: Artificial Sequence
<220> FEATURE:
<223> OTHER INFORMATION: Synthetic

<400> SEQUENCE: 242

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asp Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Ser Gly Ser Ile His Trp Val
145                 150                 155                 160

Arg Gln Ala Pro Gly Lys Gly Leu Glu Trp Val Ala Phe Ile Gly Pro
            165                 170                 175

Phe Gly Gly Tyr Thr Ser Tyr Ala Asp Ser Val Lys Gly Arg Phe Thr
        180                 185                 190

Ile Ser Ala Asp Thr Ser Lys Asn Thr Ala Tyr Leu Gln Met Asn Ser
    195                 200                 205

Leu Arg Ala Glu Asp Thr Ala Val Tyr Tyr Cys Ala Arg Phe Gly Trp
210                 215                 220

Asn Asp Tyr Asp Phe Met Asp Tyr Trp Gly Gln Gly Thr Leu Val Thr
225                 230                 235                 240

Val Ser Ser Ala Ser Ala Ala Ala
            245

<210> SEQ ID NO 243
<211> LENGTH: 248
<212> TYPE: PRT
<213> ORGANISM: Artificial Sequence
<220> FEATURE:
<223> OTHER INFORMATION: Synthetic

<400> SEQUENCE: 243

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Ser Gly Ala Pro Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Gly Ser Glu Val Gln Leu Val
            115                 120                 125

```
Glu Ser Gly Gly Gly Leu Val Gln Pro Gly Gly Ser Leu Arg Leu Ser
            130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ala Arg Phe Gly Val
            210                 215                 220

Val Tyr Asp Gly Ile Met Asp Tyr Trp Gly Gln Gly Thr Leu Val Thr
225                 230                 235                 240

Val Ser Ser Ala Ser Ala Ala Ala
                245
```

<210> SEQ ID NO 244
<211> LENGTH: 248
<212> TYPE: PRT
<213> ORGANISM: Artificial Sequence
<220> FEATURE:
<223> OTHER INFORMATION: Synthetic
<400> SEQUENCE: 244

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Trp
                20                  25                  30

Val Ala Trp Tyr Gln Gln Lys Pro Gly Lys Ala Pro Lys Leu Leu Ile
                35                  40                  45

Ser Gly Thr Ala Gly Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Phe Pro Val
                85                  90                  95

Thr Phe Gly Gln Gly Thr Lys Val Glu Ile Lys Arg Gly Gly Ser Ser
                100                 105                 110

Arg Phe Pro Pro Leu Val Ala Gly Gly Gly Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Thr Ile Asp Asp Tyr Phe Ile His Trp Val
145                 150                 155                 160

Arg Gln Ala Pro Gly Lys Gly Leu Glu Trp Val Ala Gly Ile Gly Pro
                165                 170                 175

Ser Trp Gly Tyr Thr Phe Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ala Arg Phe Gly His
            210                 215                 220

Asn Phe Val Asn Gly Met Asp Tyr Trp Gly Gln Gly Thr Leu Val Thr
225                 230                 235                 240
```

-continued

Val Ser Ser Ala Ser Ala Ala Ala
                245

<210> SEQ ID NO 245
<211> LENGTH: 251
<212> TYPE: PRT
<213> ORGANISM: Artificial Sequence
<220> FEATURE:
<223> OTHER INFORMATION: Synthetic

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Trp Trp
            20                  25                  30

Val Ala Trp Tyr Gln Gln Lys Pro Gly Lys Ala Pro Lys Leu Leu Ile
        35                  40                  45

Ser Gly Ala Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Asp Ser Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Gly Gly Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Gly Ser Ser Gly Ile
145                 150                 155                 160

His Trp Val Arg Gln Ala Pro Gly Lys Gly Leu Glu Trp Val Ala Gly
                165                 170                 175

Ile Trp Pro Tyr Trp Gly Ser Thr Tyr Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Val Gly Tyr His Tyr Met Asp Tyr Trp Gly Gln Gly Thr
225                 230                 235                 240

Leu Val Thr Val Ser Ser Ala Ser Ala Ala Ala
                245                 250

<210> SEQ ID NO 246
<211> LENGTH: 251
<212> TYPE: PRT
<213> ORGANISM: Artificial Sequence
<220> FEATURE:
<223> OTHER INFORMATION: Synthetic

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Asp Gly
            20                  25                  30

Val Ala Trp Tyr Gln Gln Lys Pro Gly Lys Ala Pro Lys Leu Leu Ile
        35                  40                  45

Ser Gly Ser Ser Trp Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Gly Glu Val
            115                 120                 125

Gln Leu Val Glu Ser Gly Gly Leu Val Gln Pro Gly Gly Ser Leu
        130                 135                 140

Arg Leu Ser Cys Ala Ala Ser Glu Phe Thr Ile Gly Ser Trp Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
        210                 215                 220

Phe Asp Ile Trp Asn Tyr Phe Gly Met Asp Tyr Trp Gly Gln Gly Thr
225                 230                 235                 240

Leu Val Thr Val Ser Ser Ala Ser Ala Ala
                245                 250

<210> SEQ ID NO 247
<211> LENGTH: 251
<212> TYPE: PRT
<213> ORGANISM: Artificial Sequence
<220> FEATURE:
<223> OTHER INFORMATION: Synthetic

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Asp Gly
            20                  25                  30

Val Ala Trp Tyr Gln Gln Lys Pro Gly Lys Ala Pro Lys Leu Leu Ile
        35                  40                  45

Tyr Ser Ala Gly Trp Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
            115                 120                 125

Gln Leu Val Glu Ser Gly Gly Leu Val Gln Pro Gly Gly Ser Leu
        130                 135                 140

Arg Leu Ser Cys Ala Ala Ser Gly Phe Thr Ile Asn Asp Trp Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Ser Tyr Ala Asp Ser Val Arg Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Val Asn Trp Asp Phe Tyr Gly Met Asp Tyr Trp Gly Gln Gly Thr
225                 230                 235                 240

Leu Val Thr Val Ser Ser Ala Ser Ala Ala Ala
                245                 250

<210> SEQ ID NO 248
<211> LENGTH: 250
<212> TYPE: PRT
<213> ORGANISM: Artificial Sequence
<220> FEATURE:
<223> OTHER INFORMATION: Synthetic

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Asn
            20                  25                  30

Val Ala Trp Tyr Gln Gln Lys Pro Gly Lys Ala Pro Lys Leu Leu Ile
        35                  40                  45

Tyr Gly Pro Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Asp Trp Gly Ile
145                 150                 155                 160

His Trp Val Arg Gln Ala Pro Gly Lys Gly Leu Glu Trp Val Ala Gly
                165                 170                 175

Ile Trp Pro Tyr Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Tyr His Val Tyr Phe Trp Trp Met Asp Tyr Trp Gly Gln Gly Thr Leu
225                 230                 235                 240

Val Thr Val Ser Ser Ala Ser Ala Ala Ala
                245                 250

<210> SEQ ID NO 249

```
<211> LENGTH: 251
<212> TYPE: PRT
<213> ORGANISM: Artificial Sequence
<220> FEATURE:
<223> OTHER INFORMATION: Synthetic

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Phe Gly
            20                  25                  30

Val Ala Trp Tyr Gln Gln Lys Pro Gly Lys Ala Pro Lys Leu Leu Ile
        35                  40                  45

Ser Gly Thr Thr Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Gly Gly Ile
145                 150                 155                 160

His Trp Val Arg Gln Ala Pro Gly Lys Gly Leu Glu Trp Val Ala Gly
                165                 170                 175

Ile Trp Pro Tyr Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asp Asn Asn Trp Val Gly Asn Met Asp Tyr Trp Gly Gln Gly Thr
225                 230                 235                 240

Leu Val Thr Val Ser Ser Ala Ser Ala Ala Ala
                245                 250

<210> SEQ ID NO 250
<211> LENGTH: 251
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Gly Gly
            20                  25                  30

Val Ala Trp Tyr Gln Gln Lys Pro Gly Lys Ala Pro Lys Leu Leu Ile
        35                  40                  45

Ser Gly Pro Pro Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
        Glu Asp Phe Ala Thr Tyr Tyr Cys Gln Gln Tyr Phe Asn Tyr Pro Ile
                            85                  90                  95

Thr Phe Gly Gln Gly Thr Lys Val Glu Ile Lys Arg Gly Gly Ser Ser
                        100                 105                 110

Arg Ser Ser Ser Gly Gly Gly Ser Gly Gly Gly Gly Glu Val
                    115                 120                 125

Gln Leu Val Glu Ser Gly Gly Gly Leu Val Gln Pro Gly Gly Ser Leu
                130                 135                 140

Arg Leu Ser Cys Ala Ala Ser Gly Phe Thr Ile Asn Asp His Gly Ile
        145                 150                 155                 160

His Trp Val Arg Gln Ala Pro Gly Lys Gly Leu Glu Trp Val Ala Gly
                            165                 170                 175

Ile Gly Pro Phe Gly Gly Tyr Thr Ser Tyr Ala Asp Ser Val Lys Gly
                        180                 185                 190

Arg Phe Thr Ile Ser Ala Asp Thr Ser Lys Asn Thr Ala Tyr Leu Gln
                    195                 200                 205

Met Asn Ser Leu Arg Ala Glu Asp Thr Ala Val Tyr Tyr Cys Ala Arg
                210                 215                 220

Phe Asn Phe Asn Asp Val Gly Gly Met Asp Tyr Trp Gly Gln Gly Thr
        225                 230                 235                 240

Leu Val Thr Val Ser Ser Ala Ser Ala Ala Ala
                            245                 250

<210> SEQ ID NO 251
<211> LENGTH: 250
<212> TYPE: PRT
<213> ORGANISM: Artificial Sequence
<220> FEATURE:
<223> OTHER INFORMATION: Synthetic

<400> SEQUENCE: 251

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Asp Val Tyr Ser Ser
                    20                  25                  30

Val Ala Trp Tyr Gln Gln Lys Pro Gly Lys Ala Pro Lys Leu Leu Ile
                        35                  40                  45

Ser Tyr Thr Ser Tyr Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
        65                  70                  75                  80

Glu Asp Phe Ala Thr Tyr Tyr Cys Gln Gln Tyr Tyr Gly Gly Pro Met
                            85                  90                  95

Thr Phe Gly Gln Gly Thr Lys Val Glu Ile Lys Arg Gly Gly Ser Ser
                        100                 105                 110

Arg Ser Ser Ser Leu Trp Arg Gly Ser Gly Gly Gly Glu Val Gln
                    115                 120                 125

Leu Val Glu Ser Gly Gly Gly Leu Val Gln Pro Gly Gly Ser Leu Arg
                130                 135                 140

Leu Ser Cys Ala Ala Ser Gly Phe Thr Ile Asn Asn Trp Gly Ile His
        145                 150                 155                 160

Trp Val Arg Gln Ala Pro Gly Lys Gly Leu Glu Trp Val Ala Gly Ile
                            165                 170                 175

Trp Pro Phe Gly Gly Tyr Thr Tyr Tyr Ala Asp Ser Val Lys Gly Arg
```

```
                         180                 185                 190
Phe Thr Ile Ser Ala Asp Thr Ser Lys Asn Thr Ala Tyr Leu Gln Met
                195                 200                 205

Asn Ser Leu Arg Ala Glu Asp Thr Ala Val Tyr Tyr Cys Ala Arg Phe
        210                 215                 220

Asp Tyr Leu Asn Asn Gly Gly Met Asp Tyr Trp Gly Gln Gly Thr Leu
225                 230                 235                 240

Val Thr Val Ser Ser Ala Ser Ala Ala Ala
                245                 250

<210> SEQ ID NO 252
<211> LENGTH: 244
<212> TYPE: PRT
<213> ORGANISM: Artificial Sequence
<220> FEATURE:
<223> OTHER INFORMATION: Synthetic

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Ser Ser
            20                  25                  30

Val Ala Trp Tyr Gln Gln Lys Pro Gly Lys Ala Pro Lys Leu Leu Ile
        35                  40                  45

Ser Tyr Thr Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Gly Ser Pro Leu
                85                  90                  95

Thr Phe Gly Gln Gly Thr Lys Val Glu Ile Lys Arg Gly Gly Ser Ser
            100                 105                 110

Arg Ser Ser Ser Ser Gly Gly Gly Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Ile Asn Asn Ser Gly Ile His Trp Val Arg Gln Ala Pro
145                 150                 155                 160

Gly Lys Gly Leu Glu Trp Val Ala Gly Ile Trp Pro Tyr Gly Gly Tyr
                165                 170                 175

Thr Ser Tyr Ala Asp Ser Val Lys Gly Arg Phe Thr Ile Ser Ala Asp
            180                 185                 190

Thr Ser Lys Asn Thr Ala Tyr Leu Gln Met Asn Ser Leu Arg Ala Glu
        195                 200                 205

Asp Thr Ala Val Tyr Tyr Cys Ala Arg Phe Asp Tyr Phe Asn Ile Gly
    210                 215                 220

Gly Met Asp Tyr Trp Gly Gln Gly Thr Leu Val Thr Val Ser Ser Ala
225                 230                 235                 240

Ser Ala Ala Ala

<210> SEQ ID NO 253
<211> LENGTH: 247
<212> TYPE: PRT
<213> ORGANISM: Artificial Sequence
<220> FEATURE:
<223> OTHER INFORMATION: Synthetic
```

<400> SEQUENCE: 253

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Tyr Trp Thr Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Ser Gly Pro Ile
                85                  90                  95

Thr Phe Gly Gln Gly Thr Lys Val Glu Ile Lys Arg Gly Gly Ser Ser
            100                 105                 110

Arg Ser Pro Ser Gly Ser Gly Gly Gly Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Phe Thr Ile Ser Asn Trp Gly Ile His Trp Val Arg
145                 150                 155                 160

Gln Ala Pro Gly Lys Gly Leu Glu Trp Val Ala Gly Ile Trp Pro Tyr
                165                 170                 175

Gly Gly Tyr Thr Phe Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ala Arg Phe Asn Tyr Leu
    210                 215                 220

Asn Leu Gly Gly Met Asp Tyr Trp Gly Gln Gly Thr Leu Val Thr Val
225                 230                 235                 240

Ser Ser Ala Ser Ala Ala Ala
                245
```

<210> SEQ ID NO 254
<211> LENGTH: 251
<212> TYPE: PRT
<213> ORGANISM: Artificial Sequence
<220> FEATURE:
<223> OTHER INFORMATION: Synthetic

<400> SEQUENCE: 254

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Trp
            20                  25                  30

Val Ala Trp Tyr Gln Gln Lys Pro Gly Lys Ala Pro Lys Leu Leu Ile
        35                  40                  45

Tyr Tyr Thr Arg Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Tyr Pro Ile
                85                  90                  95

Thr Phe Gly Gln Gly Thr Lys Val Glu Ile Lys Arg Gly Gly Ser Ser
```

```
                    100                 105                 110
Arg Ser Ser Ser Gly Gly Gly Ser Gly Gly Gly Glu Val
            115                 120                 125

Gln Leu Val Glu Ser Gly Gly Leu Val Gln Pro Gly Gly Ser Leu
            130                 135                 140

Arg Leu Ser Cys Ala Ala Ser Gly Phe Thr Ile Asn Asp Phe Ile
145                 150                 155                 160

His Trp Val Arg Gln Ala Pro Gly Lys Gly Leu Glu Trp Val Ala Gly
                165                 170                 175

Ile Gly Pro Phe Gly Gly Phe Thr Ser Tyr Ala Asp Ser Val Lys Gly
                180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
            210                 215                 220

Phe Tyr Trp Gly Asp Asp Phe Asp Met Asp Tyr Trp Gly Gln Gly Thr
225                 230                 235                 240

Leu Val Thr Val Ser Ser Ala Ser Ala Ala Ala
            245                 250

<210> SEQ ID NO 255
<211> LENGTH: 251
<212> TYPE: PRT
<213> ORGANISM: Artificial Sequence
<220> FEATURE:
<223> OTHER INFORMATION: Synthetic

<400> SEQUENCE: 255

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Asn
            20                  25                  30

Val Ala Trp Tyr Gln Gln Lys Pro Gly Lys Ala Pro Lys Leu Leu Ile
        35                  40                  45

Tyr Trp Thr Thr Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Asn Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
            115                 120                 125

Gln Leu Val Glu Ser Gly Gly Leu Val Gln Pro Gly Gly Ser Leu
            130                 135                 140

Arg Leu Ser Cys Ala Ala Ser Gly Leu Thr Ile Asn Asp Tyr Gly Ile
145                 150                 155                 160

His Trp Val Arg Gln Ala Pro Gly Lys Gly Leu Glu Trp Val Ala Ser
                165                 170                 175

Ile Gly Pro Ser Gly Gly Phe Thr Ser Tyr Ala Asp Ser Val Lys Gly
                180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
```

Phe Val Ile Tyr Trp Gly Phe Phe Met Asp Tyr Trp Gly Gln Gly Thr
225                 230                 235                 240

Leu Val Thr Val Ser Ser Ala Ser Ala Ala Ala
                245                 250

<210> SEQ ID NO 256
<211> LENGTH: 251
<212> TYPE: PRT
<213> ORGANISM: Artificial Sequence
<220> FEATURE:
<223> OTHER INFORMATION: Synthetic

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Asn
            20                  25                  30

Val Ala Trp Tyr Gln Gln Lys Pro Gly Lys Ala Pro Lys Leu Leu Ile
        35                  40                  45

Tyr Trp Ala Thr Gly Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Phe Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Asn Asp Tyr Ser Ile
145                 150                 155                 160

His Trp Val Arg Gln Ala Pro Gly Lys Gly Leu Glu Trp Val Ala Ser
                165                 170                 175

Ile Trp Pro Phe Gly Gly Ser Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asn Tyr Trp Ile Gly Ile Ile Met Asp Tyr Trp Gly Gln Gly Thr
225                 230                 235                 240

Leu Val Thr Val Ser Ser Ala Ser Ala Ala Ala
                245                 250

<210> SEQ ID NO 257
<211> LENGTH: 249
<212> TYPE: PRT
<213> ORGANISM: Artificial Sequence
<220> FEATURE:
<223> OTHER INFORMATION: Synthetic

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Trp Gly
            20                  25                  30

Val Ala Trp Tyr Gln Gln Lys Pro Gly Lys Ala Pro Lys Leu Leu Ile
            35                  40                  45

Ser Trp Ser Ala Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Phe Pro Phe
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val Gln Leu
            115                 120                 125

Val Glu Ser Gly Gly Gly Leu Val Gln Pro Gly Gly Ser Leu Arg Leu
            130                 135                 140

Ser Cys Ala Ala Ser Gly Phe Thr Ile Asn Gly Gly Ile His Trp
145                 150                 155                 160

Val Arg Gln Ala Pro Gly Lys Gly Leu Glu Trp Val Ala Phe Ile Gly
                165                 170                 175

Pro Phe Gly Gly Ser Thr Phe Tyr Ala Asp Ser Val Lys Gly Arg Phe
            180                 185                 190

Thr Ile Ser Ala Asp Thr Ser Lys Asn Thr Ala Tyr Leu Gln Met Asn
            195                 200                 205

Ser Leu Arg Ala Glu Asp Thr Ala Val Tyr Tyr Cys Ala Arg Phe Phe
210                 215                 220

Gly Gly Asn Ile His Val Met Asp Tyr Trp Gly Gln Gly Thr Leu Val
225                 230                 235                 240

Thr Val Ser Ser Ala Ser Ala Ala Ala
            245

<210> SEQ ID NO 258
<211> LENGTH: 251
<212> TYPE: PRT
<213> ORGANISM: Artificial Sequence
<220> FEATURE:
<223> OTHER INFORMATION: Synthetic

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Trp Gly
            20                  25                  30

Val Ala Trp Tyr Gln Gln Lys Pro Gly Lys Ala Pro Lys Leu Leu Ile
            35                  40                  45

Ser Ser Thr Arg Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Glu Val
            115                 120                 125

```
Gln Leu Val Glu Ser Gly Gly Gly Leu Val Gln Pro Gly Gly Ser Leu
130                 135                 140

Arg Leu Ser Cys Ala Ala Ser Gly Phe Thr Ile Asp Asn Gly Ser Ile
145                 150                 155                 160

His Trp Val Arg Gln Ala Pro Gly Lys Gly Leu Glu Trp Val Ala Phe
                165                 170                 175

Ile Gly Pro Ser Gly Gly Tyr Thr Phe Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
    210                 215                 220

Phe Gly Trp His Asn Val Asp Asn Met Asp Tyr Trp Gly Gln Gly Thr
225                 230                 235                 240

Leu Val Thr Val Ser Ser Ala Ser Ala Ala Ala
                245                 250

<210> SEQ ID NO 259
<211> LENGTH: 251
<212> TYPE: PRT
<213> ORGANISM: Artificial Sequence
<220> FEATURE:
<223> OTHER INFORMATION: Synthetic

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
                20                  25                  30

Val Ala Trp Tyr Gln Gln Lys Pro Gly Lys Ala Pro Lys Leu Leu Ile
            35                  40                  45

Ser Tyr Thr Arg Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
            115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Ser Asn Tyr Phe Ile
145                 150                 155                 160

His Trp Val Arg Gln Ala Pro Gly Lys Gly Leu Glu Trp Val Ala Phe
                165                 170                 175

Ile Gly Pro Ser Gly Gly Ser Thr Tyr Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
    210                 215                 220

Phe Asp Leu Tyr Asn Tyr Gly Gly Met Asp Tyr Trp Gly Gln Gly Thr
225                 230                 235                 240
```

Leu Val Thr Val Ser Ser Ala Ser Ala Ala Ala
            245                 250

<210> SEQ ID NO 260
<211> LENGTH: 251
<212> TYPE: PRT
<213> ORGANISM: Artificial Sequence
<220> FEATURE:
<223> OTHER INFORMATION: Synthetic

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Gly
            20                  25                  30

Val Ala Trp Tyr Gln Gln Lys Pro Gly Lys Ala Pro Lys Leu Leu Ile
        35                  40                  45

Tyr Gly Thr Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Tyr Gly Ile
145                 150                 155                 160

His Trp Val Arg Gln Ala Pro Gly Lys Gly Leu Glu Trp Val Ala Phe
                165                 170                 175

Ile Gly Pro Tyr Trp Gly Tyr Thr Tyr Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Tyr Phe Phe Gly Asp Gly Leu Met Asp Tyr Trp Gly Gln Gly Thr
225                 230                 235                 240

Leu Val Thr Val Ser Ser Ala Ser Ala Ala Ala
            245                 250

<210> SEQ ID NO 261
<211> LENGTH: 251
<212> TYPE: PRT
<213> ORGANISM: Artificial Sequence
<220> FEATURE:
<223> OTHER INFORMATION: Synthetic

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Gly
            20                  25                  30

Val Ala Trp Tyr Gln Gln Lys Pro Gly Lys Ala Pro Lys Leu Leu Ile
        35                  40                  45

```
Phe Tyr Thr Arg Trp Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
        115                 120                 125

Gln Leu Val Glu Ser Gly Gly Leu Val Gln Pro Gly Gly Ser Leu
130                 135                 140

Arg Leu Ser Cys Ala Ala Ser Gly Phe Thr Ile Asn Asn Gly Gly Ile
145                 150                 155                 160

His Trp Val Arg Gln Ala Pro Gly Lys Gly Leu Glu Trp Val Ala Ser
                165                 170                 175

Ile Gly Pro Ser Trp Gly Ser Thr Val Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
210                 215                 220

Phe Gly Phe Asp Tyr Asp Gly Val Met Asp Tyr Trp Gly Gln Gly Thr
225                 230                 235                 240

Leu Val Thr Val Ser Ser Ala Ser Ala Ala
            245                 250

<210> SEQ ID NO 262
<211> LENGTH: 251
<212> TYPE: PRT
<213> ORGANISM: Artificial Sequence
<220> FEATURE:
<223> OTHER INFORMATION: Synthetic

<400> SEQUENCE: 262

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Ser Tyr Pro Gly Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Asn Asn Tyr Gly Ile
145                 150                 155                 160
```

His Trp Val Arg Gln Ala Pro Gly Lys Gly Leu Glu Trp Val Ala Phe
            165                 170                 175

Ile Gly Pro Ser Trp Gly Tyr Thr Tyr Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
210                 215                 220

Phe Gly Ile His Tyr Asp Gly Val Met Asp Tyr Trp Gly Gln Gly Thr
225                 230                 235                 240

Leu Val Thr Val Ser Ser Ala Ser Ala Ala Ala
            245                 250

<210> SEQ ID NO 263
<211> LENGTH: 251
<212> TYPE: PRT
<213> ORGANISM: Artificial Sequence
<220> FEATURE:
<223> OTHER INFORMATION: Synthetic

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
            35                  40                  45

Ser Gly Thr Ser Ser Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Phe Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
            115                 120                 125

Gln Leu Val Glu Ser Gly Gly Gly Leu Val Gln Pro Gly Gly Ser Arg
            130                 135                 140

Arg Leu Ser Cys Ala Ala Ser Gly Phe Thr Ile Asn Asn Phe Gly Ile
145                 150                 155                 160

His Trp Val Arg Gln Ala Pro Gly Lys Gly Leu Glu Trp Val Ala Ser
            165                 170                 175

Ile Gly Pro Phe Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
210                 215                 220

Phe Gly Asn Asp Tyr Asp Gly Val Met Asp Tyr Trp Gly Gln Gly Thr
225                 230                 235                 240

Leu Val Thr Val Ser Ser Ala Ser Ala Ala Ala
            245                 250

<210> SEQ ID NO 264

<211> LENGTH: 251
<212> TYPE: PRT
<213> ORGANISM: Artificial Sequence
<220> FEATURE:
<223> OTHER INFORMATION: Synthetic

<400> SEQUENCE: 264

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Trp Gly
            20                  25                  30

Val Ala Trp Tyr Gln Gln Lys Pro Gly Lys Ala Pro Lys Leu Leu Ile
        35                  40                  45

Tyr Ser Pro Pro Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Gly Glu Val
        115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Ile Asn Asn Phe Gly Ile
145                 150                 155                 160

His Trp Val Arg Gln Ala Pro Gly Lys Gly Leu Glu Trp Val Ala Ser
                165                 170                 175

Ile Gly Pro Phe Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Asn Asp Tyr Asp Gly Val Met Asp Tyr Trp Gly Gln Gly Thr
225                 230                 235                 240

Leu Val Thr Val Ser Ser Ala Ser Ala Ala Ala
                245                 250
```

<210> SEQ ID NO 265
<211> LENGTH: 251
<212> TYPE: PRT
<213> ORGANISM: Artificial Sequence
<220> FEATURE:
<223> OTHER INFORMATION: Synthetic

<400> SEQUENCE: 265

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Gly
            20                  25                  30

Val Ala Trp Tyr Gln Gln Lys Pro Gly Lys Ala Pro Lys Leu Leu Ile
        35                  40                  45

Ser Gly Pro Ser Ser Leu Tyr Ser Gly Val Pro Ser Arg Phe Ser Gly
    50                  55                  60

Ser Gly Gly Gly Thr Asp Phe Thr Leu Thr Ile Ser Ser Leu Gln Pro
```

```
             65                  70                  75                  80
Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Ser Ser
               100                 105                 110

Arg Ser Ser Ser Gly Gly Gly Ser Gly Gly Gly Glu Val
               115                 120                 125

Gln Leu Val Glu Ser Gly Gly Leu Val Gln Pro Gly Gly Ser Leu
   130                 135                 140

Arg Leu Ser Cys Ala Ala Ser Gly Phe Thr Ile Ser Asn Trp Gly Ile
145                 150                 155                 160

His Trp Val Arg Gln Ala Pro Gly Lys Gly Leu Glu Trp Val Ala Gly
               165                 170                 175

Ile Gly Pro Ser Trp Gly Tyr Thr Ser Tyr Ala Asp Ser Val Lys Gly
               180                 185                 190

Arg Phe Thr Ile Ser Ala Asp Thr Ser Lys Asn Thr Ala Tyr Leu Gln
               195                 200                 205

Met Asn Ser Leu Arg Ala Glu Asp Thr Ala Val Tyr Tyr Cys Ala Arg
   210                 215                 220

Phe Gly Asn Val Tyr Asp Gly Val Met Asp Tyr Trp Gly Gln Gly Thr
225                 230                 235                 240

Leu Val Thr Val Ser Ser Ala Ser Ala Ala Ala
               245                 250

<210> SEQ ID NO 266
<211> LENGTH: 251
<212> TYPE: PRT
<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Tyr Gly
               20                  25                  30

Val Ala Trp Tyr Gln Gln Lys Pro Gly Lys Ala Pro Lys Leu Leu Ile
               35                  40                  45

Tyr Gly Thr Thr Tyr Leu Tyr Ser Gly Val Pro Ser Arg Phe Ser Gly
   50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
               85                  90                  95

Thr Phe Gly Gln Gly Thr Lys Val Glu Ile Lys Arg Gly Gly Ser Ser
               100                 105                 110

Arg Ser Ser Ser Gly Gly Gly Gly Ser Gly Arg Gly Gly Glu Val
               115                 120                 125

Gln Leu Val Glu Ser Gly Gly Leu Val Gln Pro Gly Gly Ser Leu
   130                 135                 140

Arg Leu Ser Cys Ala Ala Ser Gly Phe Thr Ile Asn Asn Phe Gly Ile
145                 150                 155                 160

His Trp Val Arg Gln Ala Pro Gly Lys Gly Leu Glu Trp Val Ala Gly
               165                 170                 175

Ile Gly Pro Phe Trp Gly Tyr Thr Tyr Tyr Ala Asp Ser Val Lys Gly
```

```
                180              185             190
Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
            210                 215                 220

Phe Gly Asp Tyr Tyr Asp Gly Val Met Asp Tyr Trp Gly Gln Gly Thr
225                 230                 235                 240

Leu Val Thr Val Ser Ser Ala Ser Ala Ala Ala
            245                 250

<210> SEQ ID NO 267
<211> LENGTH: 251
<212> TYPE: PRT
<213> ORGANISM: Artificial Sequence
<220> FEATURE:
<223> OTHER INFORMATION: Synthetic

<400> SEQUENCE: 267

Asp Ile Gln Val Thr Gln Ser Pro Ser Ser Leu Ser Val Ser Val Gly
1               5                   10                  15

Asp Arg Val Thr Ile Thr Cys Arg Ala Ser Gln Asp Val Gly Ser Tyr
            20                  25                  30

Val Ala Trp Tyr Gln Gln Lys Pro Gly Lys Ala Pro Lys Leu Leu Ile
            35                  40                  45

Ser Ser Pro Ser Trp Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
            115                 120                 125

Gln Leu Val Glu Ser Gly Gly Gly Leu Val Gln Pro Gly Ser Ser Leu
        130                 135                 140

Arg Leu Ser Cys Ala Ala Ser Gly Phe Thr Ile Asn Asn Phe Gly Ile
145                 150                 155                 160

His Trp Val Arg Gln Ala Pro Gly Lys Gly Leu Glu Trp Val Ala Tyr
                165                 170                 175

Ile Trp Pro Phe Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
            210                 215                 220

Phe Asn Gly Asp Tyr Val Gly Leu Met Asp Tyr Trp Gly Gln Gly Thr
225                 230                 235                 240

Leu Val Thr Val Ser Ser Ala Ser Ala Ala Ala
            245                 250

<210> SEQ ID NO 268
<211> LENGTH: 251
<212> TYPE: PRT
<213> ORGANISM: Artificial Sequence
<220> FEATURE:
<223> OTHER INFORMATION: Synthetic
```

<400> SEQUENCE: 268

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Glu Pro Gly Lys Ala Pro Lys Leu Leu Ile
        35                  40                  45

Tyr Phe Ser Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Gly Glu Val
            115                 120                 125

Gln Leu Val Glu Ser Gly Gly Leu Val Gln Pro Gly Gly Ser Leu
130                 135                 140

Arg Leu Ser Cys Ala Ala Ser Gly Phe Thr Ile Gly Gly Gly Ile
145                 150                 155                 160

His Trp Val Arg Gln Ala Pro Gly Lys Gly Leu Glu Trp Val Ala Tyr
                165                 170                 175

Ile Gly Pro Tyr Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe His Asp His Ile Gly Gly Ile Met Asp Tyr Trp Gly Gln Gly Thr
225                 230                 235                 240

Leu Val Thr Val Ser Ser Ala Ser Ala Ala Ala
            245                 250

<210> SEQ ID NO 269
<211> LENGTH: 250
<212> TYPE: PRT
<213> ORGANISM: Artificial Sequence
<220> FEATURE:
<223> OTHER INFORMATION: Synthetic

<400> SEQUENCE: 269

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Ser Ser Pro Arg Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Leu
                85                  90                  95

```
Thr Phe Gly Gln Gly Thr Lys Val Glu Ile Lys Arg Gly Gly Ser Ser
            100                 105                 110

Arg Ser Ser Ser Ser Gly Gly Gly Gly Gly Gly Gly Gly Glu Val Gln
            115                 120                 125

Leu Val Glu Thr Gly Gly Gly Leu Val Gln Pro Gly Gly Ser Leu Arg
130                 135                 140

Leu Ser Cys Ala Ala Ser Gly Phe Thr Ile Gly Asn Phe Gly Ile His
145                 150                 155                 160

Trp Val Arg Gln Ala Pro Gly Lys Gly Leu Glu Trp Val Ala Tyr Ile
                165                 170                 175

Gly Pro Tyr Gly Gly Tyr Thr Phe Tyr Ala Asp Ser Val Lys Gly Arg
            180                 185                 190

Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ala Arg Phe
            210                 215                 220

Gly Asp His Phe Asp Gly Val Met Asp Tyr Trp Gly Gln Gly Thr Leu
225                 230                 235                 240

Val Thr Val Ser Ser Ala Ser Ala Ala Ala
                245                 250

<210> SEQ ID NO 270
<211> LENGTH: 251
<212> TYPE: PRT
<213> ORGANISM: Artificial Sequence
<220> FEATURE:
<223> OTHER INFORMATION: Synthetic

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Tyr Gly Pro Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Trp Pro Ile
                85                  90                  95

Thr Phe Gly Gln Gly Thr Lys Val Glu Ile Lys Arg Gly Gly Ser Ser
            100                 105                 110

Arg Ser Ser Ser Ser Gly Gly Gly Gly Ser Gly Gly Gly Gly Glu Val
            115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Ser Asp Gly Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
            195                 200                 205
```

```
Met Asn Ser Leu Arg Ala Glu Asp Thr Ala Val Tyr Tyr Cys Ala Arg
    210                 215                 220

Phe Gly Asp Asn Phe Ile Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 271
<211> LENGTH: 251
<212> TYPE: PRT
<213> ORGANISM: Artificial Sequence
<220> FEATURE:
<223> OTHER INFORMATION: Synthetic

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Asp Gly
                20                  25                  30

Val Ala Trp Tyr Gln Gln Lys Pro Gly Lys Ala Pro Lys Leu Leu Ile
            35                  40                  45

Tyr Tyr Pro Gly Tyr Leu Tyr Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Trp Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Ser Ala Val Tyr Tyr Cys Ala Arg
    210                 215                 220

Phe Gly Val Asn Tyr Asp Gly Asn Met Asp Tyr Trp Gly Gln Gly Thr
225                 230                 235                 240

Leu Val Thr Val Ser Ser Ala Ser Ala Ala Ala
                245                 250

<210> SEQ ID NO 272
<211> LENGTH: 251
<212> TYPE: PRT
<213> ORGANISM: Artificial Sequence
<220> FEATURE:
<223> OTHER INFORMATION: Synthetic

<400> SEQUENCE: 272

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asn Asn Gly
            20                  25                  30

Val Ala Trp Tyr Gln Gln Lys Pro Gly Lys Ala Pro Lys Leu Leu Ile
        35                  40                  45

Ser Gly Thr Pro Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asp Trp Pro Leu
                85                  90                  95

Thr Phe Gly Gln Gly Thr Lys Val Glu Ile Lys His Gly Gly Ser Ser
            100                 105                 110

Arg Ser Ser Ser Gly Gly Gly Ser Gly Gly Gly Gly Glu Val
        115                 120                 125

Gln Leu Val Glu Ser Gly Gly Leu Val Gln Pro Gly Gly Ser Leu
130                 135                 140

Arg Leu Ser Cys Ala Ala Ser Gly Phe Thr Ile Asn Ser Trp Gly Ile
145                 150                 155                 160

His Trp Val Arg Gln Ala Pro Gly Lys Gly Leu Glu Trp Val Ala Trp
                165                 170                 175

Ile Gly Pro Tyr Trp Gly Phe Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asp Gly His Phe Asp Gly Val Met Asp Tyr Trp Gly Gln Gly Thr
225                 230                 235                 240

Leu Val Thr Val Ser Ser Ala Ser Ala Ala Ala
            245                 250

<210> SEQ ID NO 273
<211> LENGTH: 251
<212> TYPE: PRT
<213> ORGANISM: Artificial Sequence
<220> FEATURE:
<223> OTHER INFORMATION: Synthetic

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Ser
            20                  25                  30

Val Ala Trp Tyr Gln Gln Lys Pro Gly Lys Ala Pro Lys Leu Leu Ile
        35                  40                  45

Ser Gly Ala Ala Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Asn Phe Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Gly Glu Val
        115                 120                 125
```

```
Gln Leu Val Glu Ser Gly Gly Leu Val Gln Pro Gly Gly Ser Leu
            130                 135                 140

Arg Leu Ser Cys Ala Ala Ser Gly Phe Thr Ile Ser Asn Trp Gly Ile
145                 150                 155                 160

His Trp Val Arg Gln Ala Pro Gly Lys Gly Leu Glu Trp Val Ala Ser
                165                 170                 175

Ile Gly Pro Ser Gly Gly Phe Thr Ser Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
    210                 215                 220

Phe Tyr Ile Tyr Gly Gly Val Ile Met Asp Tyr Trp Gly Gln Gly Thr
225                 230                 235                 240

Leu Val Thr Val Ser Ser Ala Ser Ala Ala Ala
                245                 250

<210> SEQ ID NO 274
<211> LENGTH: 249
<212> TYPE: PRT
<213> ORGANISM: Artificial Sequence
<220> FEATURE:
<223> OTHER INFORMATION: Synthetic

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Gly
            20                  25                  30

Val Ala Trp Tyr Gln Gln Lys Pro Gly Lys Ala Pro Lys Leu Leu Ile
        35                  40                  45

Ser Gly Pro Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Leu
                85                  90                  95

Thr Phe Gly Gln Gly Thr Lys Val Lys Arg Gly Gly Ser Ser Arg Ser
            100                 105                 110

Ser Ser Ser Gly Gly Gly Gly Ser Gly Gly Gly Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Thr Ile Ser Asn Trp Gly Ile His Trp
145                 150                 155                 160

Val Arg Gln Ala Pro Gly Lys Gly Leu Glu Trp Val Ala Gly Ile Gly
                165                 170                 175

Pro Tyr Gly Gly Tyr Thr Ser Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ala Arg Phe Gly
    210                 215                 220

Phe Tyr Phe Asp Gly Ile Met Asp Tyr Trp Gly Gln Gly Thr Leu Val
225                 230                 235                 240
```

Thr Val Ser Ser Ala Ser Ala Ala Ala
            245

<210> SEQ ID NO 275
<211> LENGTH: 251
<212> TYPE: PRT
<213> ORGANISM: Artificial Sequence
<220> FEATURE:
<223> OTHER INFORMATION: Synthetic

<400> SEQUENCE: 275

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Ser Gly
                20                  25                  30

Val Ala Trp Tyr Gln Gln Lys Pro Gly Lys Ala Pro Lys Leu Leu Ile
            35                  40                  45

Ser Gly Thr Pro Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
        115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Ile Ser Trp Gly Ile
145                 150                 155                 160

His Trp Val Arg Gln Ala Pro Gly Lys Gly Leu Glu Trp Val Ala Ser
                165                 170                 175

Ile Gly Pro Phe Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Val Asp Val Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 276
<211> LENGTH: 251
<212> TYPE: PRT
<213> ORGANISM: Artificial Sequence
<220> FEATURE:
<223> OTHER INFORMATION: Synthetic

<400> SEQUENCE: 276

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Gly Ser Gly
                20                  25                  30

Val Ala Trp Tyr Gln Gln Lys Pro Gly Lys Ala Pro Lys Leu Leu Ile

```
              35                  40                  45
Ser Trp Pro Gly Tyr Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Ile
                 85                  90                  95

Thr Phe Gly Gln Gly Thr Lys Val Glu Ile Lys Arg Gly Gly Ser Ser
                100                 105                 110

Arg Ser Ser Ser Gly Gly Gly Ser Gly Gly Gly Glu Val
                115                 120                 125

Gln Leu Val Glu Ser Gly Gly Leu Val Gln Pro Gly Gly Ser Leu
130                 135                 140

Arg Leu Ser Cys Ala Ala Ser Gly Phe Thr Ile Asp Asp Tyr Gly Ile
145                 150                 155                 160

His Trp Val Arg Gln Ala Pro Gly Lys Gly Leu Glu Trp Val Ala Phe
                165                 170                 175

Ile Gly Pro Phe Gly Gly Tyr Thr Tyr Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
                210                 215                 220

Phe Asp Asn Asn Asn Val Trp Gly Met Asp Tyr Trp Gly Gln Gly Thr
225                 230                 235                 240

Leu Val Thr Val Ser Ser Ala Ser Ala Ala Ala
                245                 250

<210> SEQ ID NO 277
<211> LENGTH: 251
<212> TYPE: PRT
<213> ORGANISM: Artificial Sequence
<220> FEATURE:
<223> OTHER INFORMATION: Synthetic

<400> SEQUENCE: 277

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Asn Ser
                 20                  25                  30

Val Ala Trp Tyr Gln Gln Lys Pro Gly Lys Ala Pro Lys Leu Leu Ile
                 35                  40                  45

Tyr Trp Ala Gly Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Gly Trp Pro Ile
                 85                  90                  95

Thr Phe Gly Gln Gly Thr Lys Val Glu Ile Lys Arg Gly Gly Ser Ser
                100                 105                 110

Arg Ser Ser Ser Gly Gly Gly Gly Leu Gly Gly Gly Glu Val
                115                 120                 125

Gln Leu Val Glu Ser Gly Gly Leu Val Gln Pro Gly Gly Ser Leu
130                 135                 140

Arg Leu Ser Cys Ala Ala Ser Gly Phe Thr Ile Gly Ser Tyr Gly Ile
```

```
            145                 150                 155                 160
His Trp Val Arg Gln Ala Pro Gly Lys Gly Leu Glu Trp Val Ala Gly
                165                 170                 175

Ile Gly Pro Tyr Gly Gly Tyr Thr Phe Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
                210                 215                 220

Phe Gly Tyr His Val Asp Gly Ile Met Asp Tyr Trp Gly Gln Gly Thr
225                 230                 235                 240

Leu Val Thr Val Ser Ser Ala Ser Ala Ala Ala
                245                 250

<210> SEQ ID NO 278
<211> LENGTH: 244
<212> TYPE: PRT
<213> ORGANISM: Artificial Sequence
<220> FEATURE:
<223> OTHER INFORMATION: Synthetic

<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Ser Phe
                20                  25                  30

Val Ala Trp Tyr Gln Gln Lys Pro Gly Lys Ala Pro Lys Leu Leu Ile
                35                  40                  45

Tyr Tyr Thr Ser Gly Leu Tyr Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Ser Ser
                100                 105                 110

Arg Ser Ser Ser Gly Gly Glu Val Gln Leu Val Glu Ser Gly Gly
                115                 120                 125

Gly Leu Val Gln Pro Gly Gly Ser Leu Arg Leu Ser Cys Ala Ala Ser
                130                 135                 140

Gly Phe Thr Ile Asn Asp Tyr Gly Ile His Trp Val Arg Gln Ala Pro
145                 150                 155                 160

Gly Lys Gly Leu Glu Trp Val Ala Gly Ile Gly Pro Phe Gly Tyr
                165                 170                 175

Thr Ser Tyr Ala Asp Ser Val Lys Gly Arg Phe Thr Ile Ser Ala Asp
                180                 185                 190

Thr Ser Lys Asn Thr Ala Tyr Leu Gln Met Asn Ser Leu Arg Ala Glu
                195                 200                 205

Asp Thr Ala Val Tyr Tyr Cys Ala Arg Phe Gly Val Leu Phe Asp Gly
                210                 215                 220

Val Met Asp Tyr Trp Gly Gln Gly Thr Leu Val Thr Val Ser Ser Ala
225                 230                 235                 240

Ser Ala Ala Ala

<210> SEQ ID NO 279
```

```
<211> LENGTH: 251
<212> TYPE: PRT
<213> ORGANISM: Artificial Sequence
<220> FEATURE:
<223> OTHER INFORMATION: Synthetic

<400> SEQUENCE: 279

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Trp Gly
            20                  25                  30

Val Ala Trp Tyr Gln Gln Lys Pro Gly Lys Ala Pro Lys Leu Leu Ile
        35                  40                  45

Ser Ser Thr Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Val
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Gly Gly Gly Ile
145                 150                 155                 160

His Trp Val Arg Gln Ala Pro Gly Lys Gly Leu Glu Trp Val Ala Phe
                165                 170                 175

Ile Trp Pro Tyr Gly Gly Phe Thr Phe Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asn Tyr Asn His Gly Trp Phe Met Asp Tyr Trp Gly Gln Gly Thr
225                 230                 235                 240

Leu Val Thr Val Ser Ser Ala Ser Ala Ala Ala
                245                 250

<210> SEQ ID NO 280
<211> LENGTH: 251
<212> TYPE: PRT
<213> ORGANISM: Artificial Sequence
<220> FEATURE:
<223> OTHER INFORMATION: Synthetic

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Ser Gly
            20                  25                  30

Val Ala Trp Tyr Gln Gln Lys Pro Gly Lys Ala Pro Lys Leu Leu Ile
        35                  40                  45

Ser Ser Ser Thr Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
```

Glu Asp Phe Ala Thr Tyr Tyr Cys Gln Gln Tyr Tyr Asp Tyr Pro Phe
65                  70                  75                  80

Thr Phe Gly Gln Gly Thr Lys Val Glu Ile Lys His Gly Gly Ser Ser
            85                  90                  95

Arg Ser Ser Ser Gly Gly Gly Ser Gly Gly Gly Glu Val
            100                 105                 110

Gln Leu Val Glu Ser Gly Gly Gly Leu Val Gln Pro Gly Gly Ser Leu
            115                 120                 125

Arg Leu Ser Cys Ala Ala Ser Gly Phe Thr Ile Asn Gly Phe Ser Ile
130                 135                 140

His Trp Val Arg Gln Ala Pro Gly Lys Gly Leu Glu Trp Val Ala Trp
145                 150                 155                 160

Ile Trp Pro Ser Gly Gly Tyr Thr Ser Tyr Ala Asp Ser Val Lys Gly
                165                 170                 175

Arg Phe Thr Ile Ser Ala Asp Thr Ser Lys Asn Thr Ala Tyr Leu Gln
        180                 185                 190

Met Asn Ser Leu Arg Ala Glu Asp Thr Ala Val Tyr Tyr Cys Ala Arg
            195                 200                 205

Phe Asn His His His His Trp Gly Met Asp Tyr Trp Gly Gln Gly Thr
210                 215                 220

Leu Val Thr Val Ser Ser Ala Ser Ala Ala Ala
225                 230                 235                 240

245                 250

<210> SEQ ID NO 281
<211> LENGTH: 251
<212> TYPE: PRT
<213> ORGANISM: Artificial Sequence
<220> FEATURE:
<223> OTHER INFORMATION: Synthetic

<400> SEQUENCE: 281

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Tyr Gly
            20                  25                  30

Val Ala Trp Tyr Gln Gln Lys Pro Gly Lys Ala Pro Lys Leu Leu Ile
        35                  40                  45

Phe Trp Thr Thr Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Glu Val
        115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Asn Asn Asp Gly Ile
145                 150                 155                 160

His Trp Val Arg Gln Ala Pro Gly Lys Gly Leu Glu Trp Val Ala Ala
                165                 170                 175

Ile Gly Pro Phe Trp Gly Ser Thr Asp Tyr Ala Asp Ser Val Lys Gly

```
                180              185                  190
Arg Phe Thr Ile Ser Ala Asp Thr Ser Thr Asn Thr Ala Tyr Leu His
            195                 200                 205

Met Asn Ser Leu Arg Ala Glu Asp Thr Ala Leu Tyr Tyr Cys Ala Arg
            210                 215                 220

Phe Gly Asn Tyr Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 282
<211> LENGTH: 251
<212> TYPE: PRT
<213> ORGANISM: Artificial Sequence
<220> FEATURE:
<223> OTHER INFORMATION: Synthetic

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Gly
            20                  25                  30

Val Ala Trp Tyr Gln Gln Lys Pro Gly Lys Ala Pro Lys Leu Leu Ile
        35                  40                  45

Ser Trp Thr Thr Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Trp Pro Leu
                85                  90                  95

Thr Phe Gly Gln Gly Thr Lys Val Glu Ile Lys Arg Gly Gly Pro Ser
            100                 105                 110

Arg Ser Ser Ser Ser Gly Gly Gly Ser Gly Gly Gly Gly Glu Val
        115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Asp Gly Tyr Gly Ile
145                 150                 155                 160

His Trp Val Arg Gln Ala Pro Gly Lys Gly Leu Glu Trp Val Ala Ser
                165                 170                 175

Ile Gly Pro Phe Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
            210                 215                 220

Phe Gly Asp Tyr Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 283
<211> LENGTH: 248
<212> TYPE: PRT
<213> ORGANISM: Artificial Sequence
<220> FEATURE:
<223> OTHER INFORMATION: Synthetic
```

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Asn Asn
            20                  25                  30

Val Ala Trp Tyr Gln Gln Lys Pro Gly Lys Ala Pro Lys Leu Leu Ile
        35                  40                  45

Phe Trp Ser Arg Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Tyr Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asp Tyr Trp Ile His Trp Val
145                 150                 155                 160

Arg Gln Ala Pro Gly Lys Gly Leu Glu Trp Val Ala Gly Ile Gly Pro
                165                 170                 175

Phe Gly Gly Phe Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe His Tyr
210                 215                 220

Tyr Trp Gly His Phe Met Asp Tyr Trp Gly Gln Gly Thr Leu Val Thr
225                 230                 235                 240

Val Ser Ser Ala Ser Ala Ala Ala
                245

<210> SEQ ID NO 284
<211> LENGTH: 248
<212> TYPE: PRT
<213> ORGANISM: Artificial Sequence
<220> FEATURE:
<223> OTHER INFORMATION: Synthetic

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Asn
            20                  25                  30

Val Ala Trp Tyr Gln Gln Lys Pro Gly Lys Ala Pro Lys Leu Leu Ile
        35                  40                  45

Phe Gly Ser Ser Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Asn Tyr Pro Phe
                85                  90                  95

Thr Phe Gly Gln Gly Thr Lys Val Glu Ile Lys Arg Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Ser Asp Gly Ser Ile His Trp Val
145                 150                 155                 160

Arg Gln Ala Pro Gly Lys Gly Leu Glu Trp Val Ala Phe Ile Gly Pro
                165                 170                 175

Tyr Trp Gly Phe Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Val Asn
    210                 215                 220

Trp Val His Tyr Gly Met Asp Tyr Trp Gly Gln Gly Thr Leu Val Thr
225                 230                 235                 240

Val Ser Ser Ala Ser Ala Ala Ala
                245

<210> SEQ ID NO 285
<211> LENGTH: 248
<212> TYPE: PRT
<213> ORGANISM: Artificial Sequence
<220> FEATURE:
<223> OTHER INFORMATION: Synthetic

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Gly Asn
            20                  25                  30

Val Ala Trp Tyr Gln Gln Lys Pro Gly Lys Ala Pro Lys Leu Leu Ile
        35                  40                  45

Ser Ser Ala Gly Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Ser Trp Pro Leu
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Asp Gly Phe Ser Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

```
Leu Arg Ala Glu Asp Thr Ala Val Tyr Tyr Cys Ala Arg Phe Asp Ile
        210                 215                 220

Trp His Asn Phe Gly Met Asp Tyr Trp Gly Gln Gly Thr Leu Val Thr
225                 230                 235                 240

Val Ser Ser Ala Ser Ala Ala Ala
                245

<210> SEQ ID NO 286
<211> LENGTH: 248
<212> TYPE: PRT
<213> ORGANISM: Artificial Sequence
<220> FEATURE:
<223> OTHER INFORMATION: Synthetic

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Asn Asn
            20                  25                  30

Val Ala Trp Tyr Gln Gln Lys Pro Gly Lys Ala Pro Lys Leu Leu Ile
        35                  40                  45

Tyr Gly Ala Ala Tyr Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gly Asn Phe Pro Val
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Gly Gly Ser Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Phe Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asn Ile
    210                 215                 220

Trp Tyr Gly Val Asn Met Asp Tyr Trp Gly Gln Gly Thr Leu Val Thr
225                 230                 235                 240

Val Ser Ser Ala Ser Ala Ala Ala
                245

<210> SEQ ID NO 287
<211> LENGTH: 248
<212> TYPE: PRT
<213> ORGANISM: Artificial Sequence
<220> FEATURE:
<223> OTHER INFORMATION: Synthetic

<400> SEQUENCE: 287

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Asn Asn Gly
            20                  25                  30

Val Ala Trp Tyr Gln Gln Lys Pro Gly Lys Ala Pro Lys Leu Leu Ile
        35                  40                  45

Tyr Tyr Thr Gly Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Ser Gly Ser Ile His Trp Val
145                 150                 155                 160

Arg Gln Ala Pro Gly Lys Gly Leu Glu Trp Val Ala Gly Ile Gly Pro
                165                 170                 175

Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Glu Tyr Tyr Cys Ala Arg Phe Leu His
    210                 215                 220

Gly Asp Ile Phe Gly Met Asp Tyr Trp Gly Gln Gly Thr Leu Val Thr
225                 230                 235                 240

Val Ser Ser Ala Ser Ala Ala Ala
                245

<210> SEQ ID NO 288
<211> LENGTH: 248
<212> TYPE: PRT
<213> ORGANISM: Artificial Sequence
<220> FEATURE:
<223> OTHER INFORMATION: Synthetic

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30

Val Ala Trp Tyr Gln Gln Lys Pro Gly Lys Ala Pro Lys Leu Leu Ile
        35                  40                  45

Ser Trp Thr Gly Ser Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Asp Phe Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

```
Glu Ser Gly Gly Gly Leu Val Arg Pro Gly Gly Ser Leu Arg Leu Ser
            130                 135                 140

Cys Ala Ala Ser Gly Phe Thr Ile Gly Asp Trp Tyr Ile His Trp Val
145                 150                 155                 160

Arg Gln Ala Pro Gly Lys Gly Leu Glu Trp Val Ala Gly Ile Gly Pro
                165                 170                 175

Tyr Trp Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Val Gly
            210                 215                 220

Asp Val Trp His Asp Met Asp Tyr Trp Gly Gln Gly Thr Leu Val Ala
225                 230                 235                 240

Val Ser Ser Ala Ser Ala Ala Ala
            245

<210> SEQ ID NO 289
<211> LENGTH: 248
<212> TYPE: PRT
<213> ORGANISM: Artificial Sequence
<220> FEATURE:
<223> OTHER INFORMATION: Synthetic

<400> SEQUENCE: 289

Asp Ile Gln Met Thr Gln Gly Pro Ser Ser Leu Ser Ala Ser Val Gly
1               5                   10                  15

Asp Arg Val Thr Ile Thr Cys Arg Ala Ser Gln Asp Val Gly Ser Trp
                20                  25                  30

Val Ala Trp Tyr Gln Gln Lys Pro Gly Lys Ala Pro Lys Leu Leu Ile
                35                  40                  45

Ser Ser Pro Pro Ser Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Asp Ser Pro Ile
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Thr Ile Ser Asp Phe Gly Ile His Trp Val
145                 150                 155                 160

Arg Gln Ala Pro Gly Lys Gly Leu Glu Trp Val Ala Gly Ile Trp Pro
                165                 170                 175

Tyr Trp Gly Tyr Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Trp Asn
            210                 215                 220

Ile Tyr Trp Asn Val Met Asp Tyr Trp Gly Gln Gly Thr Leu Val Thr
225                 230                 235                 240
```

```
Val Ser Ser Ala Ser Ala Ala Ala
            245
```

```
<210> SEQ ID NO 290
<211> LENGTH: 248
<212> TYPE: PRT
<213> ORGANISM: Artificial Sequence
<220> FEATURE:
<223> OTHER INFORMATION: Synthetic

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asn
            20                  25                  30

Val Ala Trp Tyr Gln Gln Lys Pro Gly Lys Ala Pro Lys Leu Leu Ile
        35                  40                  45

Ser Trp Ser Thr Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Trp Pro
                165                 170                 175

Tyr Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Asn
    210                 215                 220

His His Gly Gly Val Met Asp Tyr Trp Gly Gln Gly Thr Leu Val Thr
225                 230                 235                 240

Val Ser Ser Ala Ser Ala Ala Ala
            245
```

```
<210> SEQ ID NO 291
<211> LENGTH: 248
<212> TYPE: PRT
<213> ORGANISM: Artificial Sequence
<220> FEATURE:
<223> OTHER INFORMATION: Synthetic

<400> SEQUENCE: 291

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Gly Tyr
            20                  25                  30

Val Ala Trp Tyr Gln Gln Lys Pro Gly Lys Ala Pro Lys Leu Leu Ile
```

```
                35                  40                  45
Phe Gly Ala Ser Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Ser Ser Pro Leu
                 85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Trp Pro
                165                 170                 175

Phe Gly Gly Tyr Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Asp Tyr
210                 215                 220

Leu Asn Asn Gly Gly Met Asp Tyr Trp Gly Gln Gly Thr Leu Val Thr
225                 230                 235                 240

Val Ser Ser Ala Ser Ala Ala Ala
                245

<210> SEQ ID NO 292
<211> LENGTH: 248
<212> TYPE: PRT
<213> ORGANISM: Artificial Sequence
<220> FEATURE:
<223> OTHER INFORMATION: Synthetic

<400> SEQUENCE: 292

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asp Ser Asp
                 20                  25                  30

Val Ala Trp Tyr Gln Gln Lys Pro Gly Lys Ala Pro Lys Leu Leu Ile
             35                  40                  45

Ser Phe Thr Arg Ser Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Leu
                 85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Gly Asn Trp Ser Ile His Trp Val
```

```
                145                 150                 155                 160
Arg Gln Ala Pro Gly Lys Gly Leu Glu Trp Val Ala Gly Ile Trp Pro
                    165                 170                 175
Tyr Gly Gly Tyr Thr Tyr Tyr Ala Asp Ser Val Lys Gly Arg Phe Thr
                180                 185                 190
Ile Ser Ala Asp Thr Ser Lys Asn Thr Ala Tyr Leu Gln Met Asn Ser
            195                 200                 205
Leu Arg Ala Glu Asp Thr Ala Val Tyr Tyr Cys Ala Arg Phe His Tyr
        210                 215                 220
Trp Trp His Asn Ile Met Asp Tyr Trp Gly Gln Gly Thr Leu Val Thr
225                 230                 235                 240
Val Ser Ser Ala Ser Ala Ala Ala
                245

<210> SEQ ID NO 293
<211> LENGTH: 248
<212> TYPE: PRT
<213> ORGANISM: Artificial Sequence
<220> FEATURE:
<223> OTHER INFORMATION: Synthetic

<400> SEQUENCE: 293

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Gly Ser Asp
                20                  25                  30
Val Ala Trp Tyr Gln Gln Lys Pro Gly Lys Ala Pro Lys Leu Leu Ile
            35                  40                  45
Phe Phe Ser Ser Trp Leu Tyr Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Asn Tyr Pro Leu
                85                  90                  95
Thr Phe Gly Gln Gly Thr Lys Val Glu Ile Lys Arg Gly Gly Gly Gly
                100                 105                 110
Ser Ile Glu Gly Arg Ser Gly Gly Gly Gly Ser Glu Val Gln Leu Val
            115                 120                 125
Glu Ser Gly Gly Gly Leu Val Gln Pro Gly Gly Ser Leu Arg Leu Ser
        130                 135                 140
Cys Ala Ala Ser Gly Phe Thr Ile Gly Asp Trp Ser Ile His Trp Val
145                 150                 155                 160
Arg Gln Ala Pro Gly Lys Gly Leu Glu Trp Val Ala Gly Ile Trp Pro
                    165                 170                 175
Ser Gly Gly Ser Thr Tyr Tyr Ala Asp Ser Val Lys Gly Arg Phe Thr
                180                 185                 190
Ile Ser Ala Asp Thr Ser Lys Asn Thr Ala Tyr Leu Gln Met Asn Ser
            195                 200                 205
Leu Arg Ala Glu Asp Thr Ala Val Tyr Tyr Cys Ala Arg Phe Asn Tyr
        210                 215                 220
Trp Ile Asn Gly Ile Met Asp Tyr Trp Gly Gln Gly Thr Leu Val Thr
225                 230                 235                 240
Val Ser Ser Ala Ser Ala Ala Ala
                245
```

```
<210> SEQ ID NO 294
<211> LENGTH: 248
<212> TYPE: PRT
<213> ORGANISM: Artificial Sequence
<220> FEATURE:
<223> OTHER INFORMATION: Synthetic

<400> SEQUENCE: 294

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Trp
            20                  25                  30

Val Ala Trp Tyr Gln Gln Lys Pro Gly Lys Ala Pro Lys Leu Leu Ile
        35                  40                  45

Ser Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Phe Pro Val
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asp Asp Trp Gly Ile His Trp Val
145                 150                 155                 160

Arg Gln Ala Pro Gly Lys Gly Leu Glu Trp Val Ala Trp Ile Trp Pro
                165                 170                 175

Tyr Trp Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Leu Asp
    210                 215                 220

Trp Asn Asn Asn Trp Met Asp Tyr Trp Gly Gln Gly Thr Leu Val Thr
225                 230                 235                 240

Val Ser Ser Ala Ser Ala Ala Ala
                245

<210> SEQ ID NO 295
<211> LENGTH: 248
<212> TYPE: PRT
<213> ORGANISM: Artificial Sequence
<220> FEATURE:
<223> OTHER INFORMATION: Synthetic

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Ser Tyr
            20                  25                  30

Val Ala Trp Tyr Gln Gln Lys Pro Gly Lys Ala Pro Lys Leu Leu Ile
        35                  40                  45

Ser Tyr Ala Ser Gly Leu Tyr Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Ser Pro Ile
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Tyr Ile Trp Pro
                165                 170                 175

Tyr Trp Gly Phe Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Leu Asp
        210                 215                 220

Trp Asn Leu Leu Trp Met Asp Tyr Trp Gly Gln Gly Thr Leu Val Thr
225                 230                 235                 240

Val Ser Ser Ala Ser Ala Ala Ala
                245
```

<210> SEQ ID NO 296
<211> LENGTH: 248
<212> TYPE: PRT
<213> ORGANISM: Artificial Sequence
<220> FEATURE:
<223> OTHER INFORMATION: Synthetic

<400> SEQUENCE: 296

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Asn Ser
                 20                  25                  30

Val Ala Trp Tyr Gln Gln Lys Pro Gly Lys Ala Pro Lys Leu Leu Ile
             35                  40                  45

Phe Ser Pro Arg Tyr Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Trp Pro Ile
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Asn Asn Phe Gly Ile His Trp Val
145                 150                 155                 160

Arg Gln Ala Pro Gly Lys Gly Leu Glu Trp Val Ala Gly Ile Gly Pro
                165                 170                 175
```

Tyr Gly Gly Tyr Thr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Ile
210                 215                 220

His His Asp Gly Val Met Asp Tyr Trp Gly Gln Gly Thr Leu Val Thr
225                 230                 235                 240

Val Ser Ser Ala Ser Ala Ala Ala
            245

<210> SEQ ID NO 297
<211> LENGTH: 248
<212> TYPE: PRT
<213> ORGANISM: Artificial Sequence
<220> FEATURE:
<223> OTHER INFORMATION: Synthetic

<400> SEQUENCE: 297

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Tyr Ser
            20                  25                  30

Val Ala Trp Tyr Gln Gln Lys Pro Gly Lys Ala Pro Lys Leu Leu Ile
        35                  40                  45

Phe Gly Thr Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asn Ser Trp Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Asp
    210                 215                 220

Asp His Asp Gly Leu Met Asp Tyr Trp Gly Gln Gly Thr Leu Val Thr
225                 230                 235                 240

Val Ser Ser Ala Ser Ala Ala Ala
            245

<210> SEQ ID NO 298
<211> LENGTH: 248
<212> TYPE: PRT
<213> ORGANISM: Artificial Sequence
<220> FEATURE:

<223> OTHER INFORMATION: Synthetic

<400> SEQUENCE: 298

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Gly Ser Gly
            20                  25                  30
Val Ala Trp Tyr Gln Gln Lys Pro Gly Lys Ala Pro Lys Leu Leu Ile
        35                  40                  45
Phe Ser Thr Gly Gly Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Asn Trp Pro Leu
                85                  90                  95
Thr Phe Ser Gln Gly Thr Lys Val Glu Ile Lys Arg Gly Gly Gly Gly
            100                 105                 110
Ser Ile Glu Gly Arg Ser Gly Arg Gly Gly Ser Glu Val Gln Leu Val
        115                 120                 125
Glu Ser Gly Gly Gly Leu Val Gln Pro Gly Gly Ser Leu Arg Leu Ser
130                 135                 140
Cys Ala Ala Ser Gly Phe Thr Ile Ser Asn Phe Gly Ile His Trp Val
145                 150                 155                 160
Arg Gln Ala Pro Gly Lys Gly Leu Glu Trp Val Ala Gly Ile Gly Pro
                165                 170                 175
Ser Gly Gly Tyr Thr Ser Tyr Ala Asp Ser Val Lys Gly Arg Phe Thr
            180                 185                 190
Ile Ser Ala Asp Thr Ser Lys Asn Thr Ala Tyr Leu Gln Met Asn Ser
        195                 200                 205
Leu Arg Ala Glu Asp Thr Ala Val Tyr Tyr Cys Ala Arg Phe Asn Asn
    210                 215                 220
Trp Asp Ile Phe Gly Met Asp Tyr Trp Gly Gln Gly Thr Leu Val Thr
225                 230                 235                 240
Val Ser Ser Ala Ser Ala Ala Ala
                245
```

<210> SEQ ID NO 299
<211> LENGTH: 248
<212> TYPE: PRT
<213> ORGANISM: Artificial Sequence
<220> FEATURE:
<223> OTHER INFORMATION: Synthetic

<400> SEQUENCE: 299

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Gly Tyr Phe
            20                  25                  30
Val Ala Trp Tyr Gln Gln Lys Pro Gly Lys Ala Pro Lys Leu Leu Ile
        35                  40                  45
Ser Gly Thr Thr Trp Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Asn Trp Pro Leu
                85                  90                  95
```

```
Thr Phe Gly Gln Gly Thr Lys Val Glu Ile Lys Arg Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asn Gly Gly Ile His Trp Val
145                 150                 155                 160

Arg Gln Ala Pro Gly Lys Gly Leu Glu Trp Val Ala Tyr Ile Trp Pro
                165                 170                 175

Ser Gly Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Phe Asn
    210                 215                 220

Asn Asp Trp Ile Gly Met Asp Tyr Trp Gly Gln Gly Thr Leu Val Thr
225                 230                 235                 240

Val Ser Ser Ala Ser Ala Ala Ala
                245
```

```
<210> SEQ ID NO 300
<211> LENGTH: 248
<212> TYPE: PRT
<213> ORGANISM: Artificial Sequence
<220> FEATURE:
<223> OTHER INFORMATION: Synthetic

<400> SEQUENCE: 300
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Ser Ser Pro Thr Gly Leu Tyr Ser Gly Val Pro Ser Arg Phe Ser Gly
50                  55                  60

Ser Gly Ser Gly Thr Asp Phe Thr Leu Ala Ile Ser Ser Leu Gln Pro
65                  70                  75                  80

Glu Asp Phe Ala Thr Tyr Tyr Cys Gln Gln Tyr Ser Asn Trp Pro Phe
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Arg Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asn Trp Gly Ile His Trp Val
145                 150                 155                 160

Arg Gln Ala Pro Gly Lys Gly Leu Glu Trp Val Ala Gly Ile Trp Pro
                165                 170                 175

Phe Gly Gly Ser Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205
```

Leu Arg Ala Glu Asp Thr Ala Val Tyr Tyr Cys Ala Arg Phe His His
            210                 215                 220

Phe Val Trp Tyr Gly Met Asp Tyr Trp Gly Gln Gly Thr Leu Val Thr
225                 230                 235                 240

Val Ser Ser Ala Ser Ala Ala Ala
                245

<210> SEQ ID NO 301
<211> LENGTH: 243
<212> TYPE: PRT
<213> ORGANISM: Artificial Sequence
<220> FEATURE:
<223> OTHER INFORMATION: Synthetic

<400> SEQUENCE: 301

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Asp Val Ser Gly Tyr
            20                  25                  30

Val Ala Trp Tyr Gln Gln Lys Pro Gly Lys Ala Pro Lys Leu Leu Ile
        35                  40                  45

Tyr Ser Ser Gly Val Pro Ser Arg Phe Ser Gly Ser Gly Ser Gly Thr
    50                  55                  60

Asp Phe Thr Leu Thr Ile Ser Ser Leu Gln Pro Glu Asp Phe Ala Thr
65                  70                  75                  80

Tyr Tyr Cys Gln Gln Tyr Tyr Asn Trp Pro Val Thr Phe Gly Gln Gly
                85                  90                  95

Thr Lys Val Glu Ile Lys Arg Gly Gly Gly Ser Ile Glu Gly Arg
            100                 105                 110

Ser Gly Gly Gly Gly Ser Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Ser Thr Ile Gly Asn Ser Gly Ile His Trp Val Arg Gln Ala Pro Gly
145                 150                 155                 160

Lys Gly Leu Glu Trp Val Ala Tyr Ile Gly Pro Tyr Gly Gly Tyr Thr
                165                 170                 175

Ser Tyr Ala Asp Ser Val Lys Gly Arg Phe Thr Ile Ser Ala Asp Thr
            180                 185                 190

Ser Lys Asn Thr Ala Tyr Leu Gln Met Asn Ser Leu Arg Ala Glu Asp
        195                 200                 205

Thr Ala Val Tyr Tyr Cys Ala Arg Phe Asp Asp Tyr His Trp Asp Gly
    210                 215                 220

Met Asp Tyr Trp Gly Gln Gly Thr Leu Val Thr Val Ser Ser Ala Ser
225                 230                 235                 240

Ala Ala Ala

<210> SEQ ID NO 302
<211> LENGTH: 248
<212> TYPE: PRT
<213> ORGANISM: Artificial Sequence
<220> FEATURE:
<223> OTHER INFORMATION: Synthetic

<400> SEQUENCE: 302

Asp Ile Gln Met Thr Gln Ser Pro Ser Ser Leu Ser Ala Ser Val Gly
1               5                   10                  15

-continued

Asp Arg Val Thr Ile Thr Cys Arg Ala Ser Gln Asp Val Ser Asp Gly
            20                  25                  30

Val Ala Trp Tyr Gln Gln Lys Pro Gly Lys Ala Pro Lys Leu Leu Ile
        35                  40                  45

Phe Ser Thr Ser Trp Leu Tyr Ser Gly Val Pro Ser Arg Phe Ser Gly
50                  55                  60

Ser Gly Ser Gly Thr Asp Phe Thr Leu Ala Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Gly Asn Ser Gly Ile His Trp Val
145                 150                 155                 160

Arg Gln Ala Pro Gly Lys Gly Leu Glu Trp Val Ala Phe Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asn Leu
    210                 215                 220

Asp His Gly Tyr Gly Met Asp Tyr Trp Gly Gln Gly Thr Leu Val Thr
225                 230                 235                 240

Val Ser Ser Ala Ser Ala Ala Ala
                245

<210> SEQ ID NO 303
<211> LENGTH: 248
<212> TYPE: PRT
<213> ORGANISM: Artificial Sequence
<220> FEATURE:
<223> OTHER INFORMATION: Synthetic

<400> SEQUENCE: 303

Asp Ile Gln Met Ser Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30

Val Ala Trp Tyr Gln Gln Lys Pro Gly Lys Ala Pro Lys Leu Leu Ile
        35                  40                  45

Phe Ser Pro Ala Gly Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

```
Glu Ser Gly Gly Gly Leu Val Gln Pro Gly Gly Ser Leu Arg Leu Ser
            130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly His
            210                 215                 220

Asn Tyr Asp Gly Ile Met Asp Tyr Trp Gly Gln Gly Thr Leu Val Thr
225                 230                 235                 240

Val Ser Ser Ala Ser Ala Ala Ala
                245
```

<210> SEQ ID NO 304
<211> LENGTH: 248
<212> TYPE: PRT
<213> ORGANISM: Artificial Sequence
<220> FEATURE:
<223> OTHER INFORMATION: Synthetic

<400> SEQUENCE: 304

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Ser
                20                  25                  30

Val Ala Trp Tyr Gln Gln Lys Pro Gly Lys Ala Pro Lys Leu Leu Ile
            35                  40                  45

Ser Trp Pro Thr Gly Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Trp Pro Ile
                85                  90                  95

Thr Phe Gly Gln Gly Thr Lys Val Glu Ile Lys Arg Gly Gly Gly Gly
                100                 105                 110

Ser Ile Glu Gly Arg Ser Gly Ser Gly Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Val
            210                 215                 220

Ile Ile Asp Gly Ile Met Asp Tyr Trp Gly Gln Gly Thr Leu Val Thr
225                 230                 235                 240
```

```
Val Ser Ser Ala Ser Ala Ala Ala
            245
```

```
<210> SEQ ID NO 305
<211> LENGTH: 248
<212> TYPE: PRT
<213> ORGANISM: Artificial Sequence
<220> FEATURE:
<223> OTHER INFORMATION: Synthetic

<400> SEQUENCE: 305

Asp Ile Gln Met Thr Gln Ser Pro Ser Ser Leu Ser Ala Ser Val Gly
1               5                   10                  15

Asp Arg Ala Thr Ile Thr Cys Arg Ala Ser Gln Asp Val Ser Tyr Gly
            20                  25                  30

Val Ala Trp Tyr Gln Gln Lys Pro Gly Lys Ala Pro Lys Leu Leu Ile
        35                  40                  45

Ser Gly Pro Ala Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asn Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Ser Tyr Gly Ile His Trp Val
145                 150                 155                 160

Arg Gln Ala Pro Gly Lys Gly Leu Glu Trp Val Ala Phe Ile Gly Pro
                165                 170                 175

Phe Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe His Asp
    210                 215                 220

Asp Ile Asn Trp Gly Met Asp Tyr Trp Gly Gln Gly Thr Leu Val Thr
225                 230                 235                 240

Val Ser Ser Ala Ser Ala Ala Ala
            245
```

```
<210> SEQ ID NO 306
<211> LENGTH: 248
<212> TYPE: PRT
<213> ORGANISM: Artificial Sequence
<220> FEATURE:
<223> OTHER INFORMATION: Synthetic

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Gly
            20                  25                  30

Val Ala Trp Tyr Gln Gln Lys Pro Gly Lys Ala Pro Lys Leu Leu Ile
```

```
                35                  40                  45
Ser Phe Pro Thr Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Tyr Pro Ile
                 85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Trp Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Asn
210                 215                 220

His His Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 307
<211> LENGTH: 248
<212> TYPE: PRT
<213> ORGANISM: Artificial Sequence
<220> FEATURE:
<223> OTHER INFORMATION: Synthetic

<400> SEQUENCE: 307

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Asp Gly
                 20                  25                  30

Val Ala Trp Tyr Gln Gln Lys Pro Gly Lys Ala Pro Lys Leu Leu Ile
             35                  40                  45

Ser Phe Thr Thr Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Ile
                 85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asp Tyr Gly Ile His Trp Val
```

```
145                 150                 155                 160
Arg Gln Ala Pro Gly Lys Gly Leu Glu Trp Val Ala Gly Ile Gly Pro
                165                 170                 175

Phe Gly Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ala Arg Phe Gly Val
    210                 215                 220

Leu Phe Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 308
<211> LENGTH: 248
<212> TYPE: PRT
<213> ORGANISM: Artificial Sequence
<220> FEATURE:
<223> OTHER INFORMATION: Synthetic

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Gly
                20                  25                  30

Val Ala Trp Tyr Gln Gln Lys Pro Gly Lys Ala Pro Lys Leu Leu Ile
                35                  40                  45

Ser Gly Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
                100                 105                 110

Ser Ile Glu Gly Arg Ser Gly Ser Gly Gly Ser Glu Val Gln Leu Val
                115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Gly Tyr Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ala Arg Phe Gly Ile
    210                 215                 220

Asp Tyr Asp Gly Ile Met Asp Tyr Trp Gly Gln Gly Thr Leu Val Thr
225                 230                 235                 240

Val Ser Ser Ala Ser Ala Ala Ala
                245
```

```
<210> SEQ ID NO 309
<211> LENGTH: 248
<212> TYPE: PRT
<213> ORGANISM: Artificial Sequence
<220> FEATURE:
<223> OTHER INFORMATION: Synthetic

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Gly
            20                  25                  30

Val Ala Trp Tyr Gln Gln Lys Pro Gly Lys Ala Pro Lys Leu Leu Ile
        35                  40                  45

Ser Gly Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Gln Gly Arg Ser Gly Ser Gly Ser Glu Val Gln Leu Val
            115                 120                 125

Glu Ser Gly Gly Gly Leu Val Gln Pro Gly Gly Ser Leu Arg Leu Ile
130                 135                 140

Cys Ala Ala Ser Gly Phe Thr Ile Ser Gly Tyr Gly Ile His Trp Met
145                 150                 155                 160

Arg Arg Ala Pro Gly Lys Gly Leu Glu Trp Val Ala Gly Ile Gly Pro
                165                 170                 175

Tyr Gly Gly Tyr Thr Ser Tyr Ala Tyr Ser Val Lys Gly Arg Phe Thr
            180                 185                 190

Ile Ser Ala Asp Thr Thr Lys Asn Thr Ala Tyr Leu Gln Met Asn Ser
        195                 200                 205

Leu Arg Ala Glu His Thr Ala Val Tyr Tyr Cys Ala Arg Phe Ala Ile
    210                 215                 220

Asp Tyr Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 310
<211> LENGTH: 248
<212> TYPE: PRT
<213> ORGANISM: Artificial Sequence
<220> FEATURE:
<223> OTHER INFORMATION: Synthetic

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Phe Gly
            20                  25                  30

Val Ala Trp Tyr Gln Gln Lys Pro Gly Lys Ala Pro Lys Leu Leu Ile
        35                  40                  45

Ser Ser Thr Ser Trp Leu Tyr Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Asp Tyr Gly Ile His Trp Val
145                 150                 155                 160

Arg Gln Ala Pro Gly Lys Gly Leu Glu Trp Val Ala Gly Ile Gly Pro
                165                 170                 175

Ser Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Phe
    210                 215                 220

Asp Ile Ile Gly Val Met Asp Tyr Trp Gly Gln Gly Thr Leu Val Thr
225                 230                 235                 240

Val Ser Ser Ala Ser Ala Ala Ala
                245

<210> SEQ ID NO 311
<211> LENGTH: 248
<212> TYPE: PRT
<213> ORGANISM: Artificial Sequence
<220> FEATURE:
<223> OTHER INFORMATION: Synthetic

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Asp Gly
                20                  25                  30

Val Ala Trp Tyr Gln Gln Lys Pro Gly Lys Ala Pro Lys Leu Leu Ile
            35                  40                  45

Ser Gly Thr Ser Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asp Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Asn Tyr Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Val
    210                 215                 220

Asp Leu Gly Gly His Met Asp Tyr Trp Gly Gln Gly Thr Leu Val Thr
225                 230                 235                 240

Val Ser Ser Ala Ser Ala Ala Ala
                245

<210> SEQ ID NO 312
<211> LENGTH: 248
<212> TYPE: PRT
<213> ORGANISM: Artificial Sequence
<220> FEATURE:
<223> OTHER INFORMATION: Synthetic

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Ser
            20                  25                  30

Val Ala Trp Tyr Gln Gln Lys Pro Gly Lys Ala Pro Lys Leu Leu Ile
        35                  40                  45

Phe Gly Thr Arg Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Leu
                85                  90                  95

Thr Phe Gly Gln Gly Thr Lys Val Glu Ile Lys Arg Gly Gly Gly Gly
            100                 105                 110

Ser Val Glu Gly Arg Ser Gly Ser Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Ser Tyr Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Phe Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Leu Asn
    210                 215                 220

Ile His Leu Gly Trp Met Asp Tyr Trp Gly Gln Gly Thr Leu Val Thr
225                 230                 235                 240

Val Ser Ser Ala Ser Ala Ala Ala
                245

<210> SEQ ID NO 313
<211> LENGTH: 248
<212> TYPE: PRT
<213> ORGANISM: Artificial Sequence
<220> FEATURE:

<223> OTHER INFORMATION: Synthetic

<400> SEQUENCE: 313

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ser
            20                  25                  30

Val Ala Trp Tyr Gln Gln Lys Pro Gly Lys Ala Pro Lys Leu Leu Ile
        35                  40                  45

Phe Phe Ala Gly Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asp Trp Gly Ile His Trp Val
145                 150                 155                 160

Arg Gln Ala Pro Gly Lys Gly Leu Glu Trp Val Ala Ser Ile Gly Pro
                165                 170                 175

Phe Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Ala Tyr Tyr Cys Ala Arg Phe Gly Asn
    210                 215                 220

Tyr Val Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 314
<211> LENGTH: 248
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Tyr Gly
            20                  25                  30

Val Ala Trp Tyr Gln Gln Lys Pro Gly Glu Ala Pro Lys Leu Leu Ile
        35                  40                  45

Phe Phe Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Ser Ser Trp Pro Ile
                85                  90                  95

Thr Phe Gly Gln Gly Thr Lys Val Glu Val Lys Arg Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asp Trp Gly Ile His Trp Val
145                 150                 155                 160

Arg Gln Ala Pro Gly Lys Gly Leu Glu Trp Val Ala Ser Ile Gly Pro
                165                 170                 175

Phe Trp Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Phe
            210                 215                 220

Asp Val Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 315
<211> LENGTH: 248
<212> TYPE: PRT
<213> ORGANISM: Artificial Sequence
<220> FEATURE:
<223> OTHER INFORMATION: Synthetic

<400> SEQUENCE: 315

Asp Ile Gln Met Thr Gln Ser Pro Ser Ser Leu Ser Ala Ser Val Gly
1               5                   10                  15

Asp Arg Val Thr Ile Thr Cys Arg Ala Ser His Asp Val Gly Trp Gly
            20                  25                  30

Val Ala Trp Tyr Gln Gln Lys Pro Gly Lys Ala Pro Lys Leu Leu Ile
            35                  40                  45

Ser Trp Pro Thr Tyr Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Tyr Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Phe Gly Ile His Trp Val
145                 150                 155                 160

Arg Gln Ala Pro Gly Lys Gly Leu Glu Trp Val Ala Ser Ile Gly Pro
                165                 170                 175

Phe Trp Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Asn
            210                 215                 220

Asp Tyr Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 316
<211> LENGTH: 248
<212> TYPE: PRT
<213> ORGANISM: Artificial Sequence
<220> FEATURE:
<223> OTHER INFORMATION: Synthetic

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Gly
            20                  25                  30

Val Ala Trp Tyr Gln Gln Lys Pro Gly Lys Ala Pro Lys Leu Leu Ile
        35                  40                  45

Phe Gly Ser Pro Tyr Leu Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Trp Pro Ile
                85                  90                  95

Thr Phe Gly Gln Gly Thr Gln Val Gly Ile Lys Arg Gly Gly Gly Gly
            100                 105                 110

Ser Ile Glu Gly Arg Ser Gly Ser Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Ser Ile Gly Pro
            165                 170                 175

Phe Trp Gly Tyr Thr Phe Tyr Ala Asp Ser Val Lys Gly Arg Phe Thr
        180                 185                 190

Ile Ser Ala Asp Thr Ser Lys Asn Thr Ala Tyr Leu Gln Met Asn Ser
    195                 200                 205

Leu Arg Ala Glu Asp Thr Ala Val Tyr Tyr Cys Ala Arg Phe Gly Asn
            210                 215                 220

His Tyr Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 317
<211> LENGTH: 248
<212> TYPE: PRT
<213> ORGANISM: Artificial Sequence
<220> FEATURE:
<223> OTHER INFORMATION: Synthetic

<400> SEQUENCE: 317

Asp Ile Gln Met Thr Gln Ser Pro Ser Ser Leu Ser Ala Ser Val Gly

```
            1               5                  10                 15
Asp Arg Val Thr Ile Thr Cys Arg Ala Ser Gln Asp Val Trp Trp Gly
                20                  25                 30

Val Ala Trp Tyr Gln Gln Lys Pro Gly Lys Ala Pro Lys Leu Leu Ile
            35                  40                 45

Phe Gly Ala Ser Gly Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Trp Gly Ser Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Asn
210                 215                 220

Ile Val Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 318
<211> LENGTH: 248
<212> TYPE: PRT
<213> ORGANISM: Artificial Sequence
<220> FEATURE:
<223> OTHER INFORMATION: Synthetic

<400> SEQUENCE: 318

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
                20                  25                  30

Val Ala Trp Tyr Gln Gln Lys Pro Gly Lys Ala Pro Lys Leu Leu Ile
            35                  40                  45

Ser Gly Ser Gly Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Gly Ser Glu Val Gln Leu Val
```

```
            115                 120                 125
Glu Ser Gly Gly Gly Leu Val Gln Pro Gly Gly Ser Leu Arg Leu Ser
        130                 135                 140

Cys Ala Ala Ser Gly Phe Thr Ile Asp Asn Trp Gly Ile His Trp Val
145                 150                 155                 160

Arg Gln Ala Pro Gly Lys Gly Leu Glu Trp Val Ala Ser Ile Gly Pro
                165                 170                 175

Ser Trp Gly Phe Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Val
    210                 215                 220

Asp Ile Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 319
<211> LENGTH: 248
<212> TYPE: PRT
<213> ORGANISM: Artificial Sequence
<220> FEATURE:
<223> OTHER INFORMATION: Synthetic

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30

Val Ala Trp Tyr Gln Gln Lys Pro Gly Lys Ala Pro Lys Leu Leu Ile
        35                  40                  45

Phe Gly Ser Thr Trp Leu Tyr Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Asp Ser Trp Gly Ile His Trp Val
145                 150                 155                 160

Arg Gln Ala Pro Gly Lys Gly Leu Glu Trp Val Ala Gly Ile Gly Pro
                165                 170                 175

Phe Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Ile
    210                 215                 220

His Phe Asp Gly Ile Met Asp Tyr Trp Gly Gln Gly Thr Leu Val Thr
```

```
225                 230                 235                 240

Val Ser Ser Ala Ser Ala Ala Ala
                245

<210> SEQ ID NO 320
<211> LENGTH: 248
<212> TYPE: PRT
<213> ORGANISM: Artificial Sequence
<220> FEATURE:
<223> OTHER INFORMATION: Synthetic

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Gly Gly
            20                  25                  30

Val Ala Trp Tyr Gln Gln Lys Pro Gly Lys Ala Pro Lys Leu Leu Ile
        35                  40                  45

Tyr Gly Ser Ser Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asp Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Gly Tyr Gly Ile His Trp Val
145                 150                 155                 160

Arg Gln Ala Pro Gly Lys Gly Leu Glu Trp Val Ala Gly Ile Gly Pro
                165                 170                 175

Phe Trp Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly His
    210                 215                 220

Ile Val Asp Gly Leu Met Asp Tyr Trp Gly Gln Gly Thr Leu Val Thr
225                 230                 235                 240

Val Ser Ser Ala Ser Ala Ala Ala
                245

<210> SEQ ID NO 321
<211> LENGTH: 248
<212> TYPE: PRT
<213> ORGANISM: Artificial Sequence
<220> FEATURE:
<223> OTHER INFORMATION: Synthetic

<400> SEQUENCE: 321

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30
```

Val Ala Trp Tyr Gln Gln Lys Pro Gly Lys Ala Pro Lys Leu Leu Ile
            35                  40                  45

Tyr Ser Ser Thr Trp Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Ile
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Tyr Gly Ile His Trp Val
145                 150                 155                 160

Arg Gln Ala Pro Gly Lys Gly Leu Glu Trp Val Ala Gly Ile Gly Pro
                165                 170                 175

Tyr Trp Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Asp
        210                 215                 220

Val Ile Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 322
<211> LENGTH: 248
<212> TYPE: PRT
<213> ORGANISM: Artificial Sequence
<220> FEATURE:
<223> OTHER INFORMATION: Synthetic

<400> SEQUENCE: 322

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Gly Ser Gly
                20                  25                  30

Val Ala Trp Tyr Gln Gln Lys Pro Gly Lys Ala Pro Lys Leu Leu Ile
            35                  40                  45

Tyr Phe Ser Ala Ser Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Leu
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

```
Cys Ala Ala Ser Gly Phe Thr Ile Asn Asn Tyr Gly Ile His Trp Val
145                 150                 155                 160

Arg Gln Ala Pro Gly Lys Gly Leu Glu Trp Val Ala Gly Ile Gly Pro
                165                 170                 175

Ser Trp Gly Phe Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Phe
    210                 215                 220

Tyr Asn Asp Gly Phe Met Asp Tyr Trp Gly Gln Gly Thr Leu Val Thr
225                 230                 235                 240

Val Ser Ser Ala Ser Ala Ala Ala
                245
```

```
<210> SEQ ID NO 323
<211> LENGTH: 248
<212> TYPE: PRT
<213> ORGANISM: Artificial Sequence
<220> FEATURE:
<223> OTHER INFORMATION: Synthetic

<400> SEQUENCE: 323

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Ser Gly
            20                  25                  30

Val Ala Trp Tyr Gln Gln Lys Pro Gly Lys Thr Pro Lys Leu Leu Ile
        35                  40                  45

Tyr Gly Thr Thr Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Asn Phe Gly Ile His Trp Val
145                 150                 155                 160

Arg Gln Ala Pro Gly Lys Gly Leu Glu Trp Val Ala Tyr Ile Gly Pro
                165                 170                 175

Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe His Asn
    210                 215                 220

Asp Ile Gly Gly Ile Met Asp Tyr Trp Gly Gln Gly Thr Leu Val Thr
225                 230                 235                 240

Val Ser Ser Ala Ser Ala Ala Ala
                245
```

```
<210> SEQ ID NO 324
<211> LENGTH: 248
<212> TYPE: PRT
<213> ORGANISM: Artificial Sequence
<220> FEATURE:
<223> OTHER INFORMATION: Synthetic

<400> SEQUENCE: 324

Asp Ile Gln Met Ala Gln Ser Pro Ser Ser Leu Ser Ala Ser Val Gly
1               5                   10                  15

Asp Arg Val Thr Ile Thr Cys Arg Ala Ser Gln Asp Val Ser Asn Gly
            20                  25                  30

Val Ala Trp Tyr Gln Gln Lys Pro Gly Lys Ala Pro Lys Leu Leu Ile
        35                  40                  45

Tyr Gly Thr Thr Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Ser Tyr Gly Ile His Trp Val
145                 150                 155                 160

Arg Gln Ala Pro Gly Lys Gly Leu Glu Trp Val Ala Ser Ile Gly Pro
                165                 170                 175

Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Ile
    210                 215                 220

Trp Phe Asp Gly Leu Met Asp Tyr Trp Gly Gln Gly Thr Leu Val Thr
225                 230                 235                 240

Val Ser Ser Ala Ser Ala Ala Ala
                245

<210> SEQ ID NO 325
<211> LENGTH: 248
<212> TYPE: PRT
<213> ORGANISM: Artificial Sequence
<220> FEATURE:
<223> OTHER INFORMATION: Synthetic

<400> SEQUENCE: 325

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asn
            20                  25                  30

Val Ala Trp Tyr Gln Gln Lys Pro Gly Lys Ala Pro Lys Leu Leu Ile
        35                  40                  45

Tyr Gly Ala Pro Tyr Leu Tyr Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Gly Gly Ile His Trp Val
145                 150                 155                 160

Arg Gln Ala Pro Gly Lys Gly Leu Glu Trp Val Ala Ser Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Gly Asp Thr Ala Val Tyr Tyr Cys Ala Arg Phe Gly His
210                 215                 220

His Tyr Asp Gly His Met Asp Tyr Trp Gly Gln Gly Thr Leu Val Thr
225                 230                 235                 240

Val Ser Ser Ala Ser Ala Ala Ala
                245

<210> SEQ ID NO 326
<211> LENGTH: 248
<212> TYPE: PRT
<213> ORGANISM: Artificial Sequence
<220> FEATURE:
<223> OTHER INFORMATION: Synthetic

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Ser Gly
            20                  25                  30

Val Ala Trp Tyr Gln Gln Lys Pro Gly Lys Ala Pro Lys Leu Leu Ile
        35                  40                  45

Ser Gly Thr Pro Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asp Glu Tyr Gly Ile His Trp Val
145                 150                 155                 160

Arg Gln Ala Pro Gly Lys Gly Leu Glu Trp Val Ala Phe Ile Gly Pro
                165                 170                 175

```
Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly His
210                 215                 220

Leu His Asp Gly Leu Met Asp Tyr Trp Gly Gln Gly Thr Leu Val Thr
225                 230                 235                 240

Val Ser Ser Ala Ser Ala Ala Ala
                245
```

<210> SEQ ID NO 327
<211> LENGTH: 248
<212> TYPE: PRT
<213> ORGANISM: Artificial Sequence
<220> FEATURE:
<223> OTHER INFORMATION: Synthetic

<400> SEQUENCE: 327

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Tyr Gly Ser Pro Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Arg Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asp Ser Trp Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Asp
    210                 215                 220

Tyr Ile Asp Gly Val Met Asp Tyr Trp Gly Gln Gly Thr Leu Val Thr
225                 230                 235                 240

Val Ser Ser Ala Ser Ala Ala Ala
                245
```

<210> SEQ ID NO 328
<211> LENGTH: 248
<212> TYPE: PRT
<213> ORGANISM: Artificial Sequence
<220> FEATURE:
<223> OTHER INFORMATION: Synthetic

<400> SEQUENCE: 328

Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Asp Val Cys Ser Gly
            20                  25                  30

Val Ala Trp Tyr Gln Gln Lys Pro Gly Lys Ala Pro Lys Leu Leu Ile
        35                  40                  45

Ser Gly Ser Pro Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Trp Pro Met
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asp Asn Trp Trp Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asn Asn
    210                 215                 220

Cys Gly Ile Tyr Val Met Asp Tyr Trp Gly Gln Gly Thr Leu Val Thr
225                 230                 235                 240

Val Ser Ser Ala Ser Ala Ala Ala
                245

<210> SEQ ID NO 329
<211> LENGTH: 248
<212> TYPE: PRT
<213> ORGANISM: Artificial Sequence
<220> FEATURE:
<223> OTHER INFORMATION: Synthetic

<400> SEQUENCE: 329

Asp Ile Gln Met Thr Gln Ser Pro Ser Ser Leu Ser Ala Ser Val Gly
1               5                   10                  15

Asn Arg Val Thr Ile Thr Cys Arg Ala Ser Gln Asp Val Ser Tyr Gly
            20                  25                  30

Val Ala Trp Tyr Gln Gln Lys Pro Gly Lys Ala Pro Lys Leu Leu Ile
        35                  40                  45

Ser Gly Ala Gly Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Trp Pro Ile

```
                         85                  90                  95
Thr Phe Gly Gln Gly Thr Lys Val Glu Ile Lys Arg Gly Gly Gly
                100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Ser Tyr Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Trp
    210                 215                 220

His His Leu His Leu Met Asp Tyr Trp Gly Gln Gly Thr Leu Val Thr
225                 230                 235                 240

Val Ser Ser Ala Ser Ala Ala Ala
                245

<210> SEQ ID NO 330
<211> LENGTH: 248
<212> TYPE: PRT
<213> ORGANISM: Artificial Sequence
<220> FEATURE:
<223> OTHER INFORMATION: Synthetic

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Gly
            20                  25                  30

Val Ala Trp Tyr Gln Gln Lys Pro Gly Lys Ala Pro Lys Leu Leu Ile
        35                  40                  45

Ser Gly Ala Gly Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Trp Pro Ile
                85                  90                  95

Thr Phe Gly Gln Gly Thr Lys Val Glu Ile Lys Arg Gly Gly Gly Gly
                100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Asn Phe Gly Ile His Trp Val
145                 150                 155                 160

Arg Gln Ala Pro Gly Lys Gly Leu Glu Trp Val Ala Tyr Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
```

```
              195                 200                 205
Leu Arg Ala Glu Asp Ala Ala Val Tyr Tyr Cys Ala Arg Phe His Ile
    210                 215                 220

His Asn Leu Trp Gly Met Asp Tyr Trp Gly Gln Gly Thr Leu Val Thr
225                 230                 235                 240

Val Ser Ser Ala Ser Ala Ala Ala
                245

<210> SEQ ID NO 331
<211> LENGTH: 278
<212> TYPE: PRT
<213> ORGANISM: Artificial Sequence
<220> FEATURE:
<223> OTHER INFORMATION: Synthetic

<400> SEQUENCE: 331

Met Ala Glu Leu Asp Ile Gln Met Thr Gln Thr Thr Ser Ser Leu Ser
1               5                   10                  15

Ala Ser Leu Gly Asp Arg Val Thr Ile Ser Cys Arg Thr Ser Gln Asp
            20                  25                  30

Ile Ser Asn Tyr Leu Asn Trp Tyr Gln Gln Lys Pro Asn Gly Thr Ile
        35                  40                  45

Lys Leu Leu Ile Tyr Tyr Thr Ser Gly Leu Tyr Ser Gly Val Pro Ser
    50                  55                  60

Arg Phe Ser Gly Ser Gly Ser Gly Ala Asp Tyr Ser Leu Thr Ile Ser
65                  70                  75                  80

Asn Val Glu Gln Glu Asp Ile Ala Thr Tyr Phe Cys Gln Gln Val Asn
                85                  90                  95

Thr Leu Pro Tyr Thr Phe Gly Gly Gly Thr Lys Leu Glu Leu Lys Ser
            100                 105                 110

Ser Gly Gly Gly Gly Ser Gly Gly Gly Gly Ser Ser Arg Ser
        115                 120                 125

Ser Phe Glu Val Gln Leu Gln Gln Ser Gly Ala Glu Leu Val Lys Pro
    130                 135                 140

Gly Ala Ser Val Lys Met Ser Cys Lys Ala Phe Gly Tyr Thr Phe Thr
145                 150                 155                 160

Thr Tyr Pro Ile Glu Trp Met Lys Gln Asn His Gly Lys Ser Leu Glu
                165                 170                 175

Trp Ile Gly Asn Phe His Pro Tyr Asn Asp Tyr Thr Asn Tyr Asn Glu
            180                 185                 190

Lys Phe Lys Gly Lys Ala Lys Leu Thr Val Glu Lys Ser Ser Thr Thr
        195                 200                 205

Val Tyr Leu Glu Leu Ser Arg Leu Thr Ser Asp Asp Ser Ala Val Tyr
    210                 215                 220

Tyr Cys Ala Arg Arg His Asp Gly Tyr Tyr Gly Ala Met Asp Tyr Trp
225                 230                 235                 240

Gly Gln Gly Thr Ser Val Thr Val Ser Ser Ala Lys Thr Thr Ala Pro
                245                 250                 255

Ser Val Thr Ser Ala Ala Ala Gly Ala Pro Val Pro Tyr Pro Asp Pro
            260                 265                 270

Leu Glu Pro Arg Ala Ala
        275

<210> SEQ ID NO 332
<211> LENGTH: 278
<212> TYPE: PRT
```

<213> ORGANISM: Artificial Sequence
<220> FEATURE:
<223> OTHER INFORMATION: Synthetic

<400> SEQUENCE: 332

```
Met Ala Glu Leu Asp Ile Lys Ile Thr Gln Ser Pro Ala Ser Leu Ser
1               5                   10                  15

Ala Ser Val Gly Glu Thr Val Thr Ile Thr Cys Arg Ala Ser Glu Asn
            20                  25                  30

Ile Tyr Ser Tyr Leu Ala Trp Tyr Gln Gln Lys Gln Gly Lys Ser Pro
        35                  40                  45

Gln Leu Leu Val Tyr Asn Ala Lys Thr Leu Ala Glu Gly Val Pro Ser
    50                  55                  60

Arg Phe Ser Gly Ser Gly Ser Gly Thr Gln Phe Ser Leu Lys Ile Asn
65                  70                  75                  80

Ser Leu Gln Pro Glu Asp Phe Gly Ser Tyr Tyr Cys Gln His His Tyr
                85                  90                  95

Gly Thr Pro Tyr Thr Phe Gly Gly Gly Thr Lys Leu Glu Leu Lys Ser
            100                 105                 110

Ser Gly Gly Gly Gly Ser Gly Gly Gly Gly Ser Ser Arg Ser
            115                 120                 125

Ser Leu Glu Val Gln Leu Gln Gln Ser Gly Ala Glu Leu Val Lys Pro
    130                 135                 140

Gly Ala Ser Val Lys Met Ser Cys Lys Ala Phe Gly Tyr Thr Phe Thr
145                 150                 155                 160

Thr Tyr Pro Ile Glu Trp Met Lys Gln Asn His Gly Lys Ser Leu Glu
                165                 170                 175

Trp Ile Gly Asn Phe His Pro Tyr Asn Asp Asp Thr Lys Tyr Asn Glu
            180                 185                 190

Lys Phe Lys Gly Lys Ala Lys Leu Thr Val Glu Lys Ser Ser Ser Thr
        195                 200                 205

Val Tyr Leu Glu Leu Ser Arg Leu Thr Ser Asp Asp Ser Ala Val Tyr
    210                 215                 220

Tyr Cys Ala Arg Arg Asn Asp Gly Tyr Tyr Gly Ala Met Asp Tyr Trp
225                 230                 235                 240

Gly Gln Gly Thr Ser Val Thr Val Ser Ser Ala Lys Thr Thr Ala Pro
                245                 250                 255

Ser Val Thr Ser Ala Ala Ala Gly Ala Pro Val Pro Tyr Pro Asp Pro
            260                 265                 270

Leu Glu Pro Arg Ala Ala
        275
```

<210> SEQ ID NO 333
<211> LENGTH: 260
<212> TYPE: PRT
<213> ORGANISM: Artificial Sequence
<220> FEATURE:
<223> OTHER INFORMATION: Synthetic

<400> SEQUENCE: 333

```
Met Ala Glu Leu Asp Ala Val Val Thr Gln Glu Ser Ala Leu Thr Thr
1               5                   10                  15

Ser Pro Gly Glu Thr Val Thr Leu Thr Cys Arg Ser Ser Thr Gly Thr
            20                  25                  30

Val Thr Thr Ser Asn Tyr Ala Asn Trp Val Gln Glu Lys Pro Asp His
        35                  40                  45
```

```
Leu Phe Thr Gly Leu Ile Gly Gly Thr Lys Asn Arg Ala Pro Gly Val
 50                  55                  60

Pro Ala Arg Phe Ser Gly Ser Leu Ile Gly Asp Lys Ala Ala Leu Thr
 65                  70                  75                  80

Ile Thr Gly Ala Gln Thr Glu Asp Glu Ala Ile Tyr Phe Cys Ala Leu
                 85                  90                  95

Trp Tyr Ser Asn His Trp Val Phe Gly Gly Thr Lys Leu Thr Val
                100                 105                 110

Leu Gly Ser Ser Gly Gly Gly Ser Gly Gly Gly Gly Ser
            115                 120                 125

Ser Arg Ser Ser Leu Glu Val Gln Leu Gln Gln Ser Gly Pro Glu Leu
    130                 135                 140

Val Arg Pro Gly Asp Ser Val Lys Ile Ser Cys Lys Ala Ser Gly Tyr
145                 150                 155                 160

Thr Phe Ser Asp Tyr Ala Val His Trp Val Lys Arg Ser His Gly Lys
                165                 170                 175

Ser Leu Glu Trp Ile Gly Val Ile Ser Ile Tyr Tyr Asp Asn Ile Asn
            180                 185                 190

Tyr Asn Gln Asn Phe Lys Gly Lys Ala Thr Met Thr Val Asp Lys Ser
            195                 200                 205

Ser Ser Thr Ala Tyr Leu Glu Leu Ala Arg Leu Thr Ser Glu Asp Ser
    210                 215                 220

Ala Ile Tyr Tyr Cys Ala Arg Arg Gly Phe Asp Tyr Trp Gly Pro Gly
225                 230                 235                 240

Thr Thr Leu Thr Val Ser Ser Ala Lys Thr Thr Ala Pro Ser Val Thr
                245                 250                 255

Ser Ala Ala Ala
            260

<210> SEQ ID NO 334
<211> LENGTH: 275
<212> TYPE: PRT
<213> ORGANISM: Artificial Sequence
<220> FEATURE:
<223> OTHER INFORMATION: Synthetic

<400> SEQUENCE: 334

Met Ala Glu Leu Asp Ile Gln Met Asn Gln Ser His Lys Phe Met Ser
 1               5                  10                  15

Thr Ser Val Gly Asp Arg Val Ser Ile Thr Cys Lys Ala Ser Gln Asp
                20                  25                  30

Val Ser Thr Ala Val Ala Trp Tyr Gln Gln Lys Pro Gly Gln Ser Pro
             35                  40                  45

Lys Leu Leu Ile Tyr Trp Ala Ser Thr Arg His Thr Gly Val Pro Gly
 50                  55                  60

Arg Phe Thr Gly Ser Gly Ser Gly Ala Asp Tyr Thr Leu Thr Ile Ser
 65                  70                  75                  80

Ser Val Gln Ala Glu Asp Leu Ala Leu Tyr Tyr Cys Gln Gln His Tyr
                 85                  90                  95

Ser Thr Pro Tyr Thr Phe Gly Gly Gly Thr Lys Leu Glu Ile Lys Ser
                100                 105                 110

Ser Gly Gly Gly Gly Ser Gly Gly Gly Gly Ser Ser Arg Ser
            115                 120                 125

Ser Leu Glu Val Gln Leu Gln Gln Ser Gly Ala Glu Leu Val Lys Pro
    130                 135                 140
```

Gly Ala Ser Val Lys Leu Ser Cys Thr Ala Ser Gly Phe Asn Ile Lys
145                 150                 155                 160

Asn Thr Tyr Met His Trp Val Lys Gln Arg Pro Glu Gln Gly Leu Glu
            165                 170                 175

Trp Ile Gly Arg Ile Asp Pro Ala Asn Gly Asn Thr Lys Tyr Asp Pro
        180                 185                 190

Lys Leu Gln Gly Lys Ala Thr Ile Thr Ala Asp Thr Ser Ser Asn Thr
    195                 200                 205

Ala Tyr Leu His Leu Ser Ser Leu Thr Ser Glu Asp Thr Ala Val Tyr
210                 215                 220

Tyr Cys Val Pro Tyr Tyr Arg Gly Ala Met Asp Tyr Trp Gly Gln Gly
225                 230                 235                 240

Thr Ser Val Thr Val Ser Ser Glu Ser Gln Ser Phe Pro Asn Val Thr
            245                 250                 255

Ser Ala Ala Ala Gly Ala Pro Val Pro Tyr Pro Asp Pro Leu Glu Pro
            260                 265                 270

Arg Ala Ala
    275

<210> SEQ ID NO 335
<211> LENGTH: 21
<212> TYPE: DNA
<213> ORGANISM: Artificial Sequence
<220> FEATURE:
<223> OTHER INFORMATION: Synthetic

<400> SEQUENCE: 335
ggaagatcta gaggaaccac c                                         21

<210> SEQ ID NO 336
<211> LENGTH: 21
<212> TYPE: DNA
<213> ORGANISM: Artificial Sequence
<220> FEATURE:
<223> OTHER INFORMATION: Synthetic

<400> SEQUENCE: 336
ggtggttcct ctagatcttc c                                         21

<210> SEQ ID NO 337
<211> LENGTH: 30
<212> TYPE: DNA
<213> ORGANISM: Artificial Sequence
<220> FEATURE:
<223> OTHER INFORMATION: Synthetic

<400> SEQUENCE: 337
tgcagccacc gtacgtttga tttccacctt                                30

<210> SEQ ID NO 338
<211> LENGTH: 30
<212> TYPE: DNA
<213> ORGANISM: Artificial Sequence
<220> FEATURE:
<223> OTHER INFORMATION: Synthetic

<400> SEQUENCE: 338
aaggtggaaa tcaaacgtac ggtggctgca                                30

<210> SEQ ID NO 339
<211> LENGTH: 21
<212> TYPE: DNA

```
<213> ORGANISM: Artificial Sequence
<220> FEATURE:
<223> OTHER INFORMATION: Synthetic

<400> SEQUENCE: 339
ctgcacttca gatgcgacac g                                              21

<210> SEQ ID NO 340
<211> LENGTH: 21
<212> TYPE: DNA
<213> ORGANISM: Artificial Sequence
<220> FEATURE:
<223> OTHER INFORMATION: Synthetic

<400> SEQUENCE: 340
cgtgtcgcat ctgaagtgca g                                              21
```